United States Patent
Stone et al.

(10) Patent No.: US 6,593,104 B1
(45) Date of Patent: Jul. 15, 2003

(54) MACULAR DEGENERATION DIAGNOSTICS AND THERAPEUTICS

(75) Inventors: Edwin M. Stone, Iowa City, IA (US); Val C. Sheffield, Coralville, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 0 days.

(21) Appl. No.: 09/322,357

(22) Filed: May 28, 1999

Related U.S. Application Data

(63) Continuation-in-part of application No. 09/248,757, filed on Feb. 12, 1999, now Pat. No. 6,417,342.

(51) Int. Cl.$^7$ .......................... C12N 15/00; C12N 5/00; C12P 21/06; C07H 21/02; C07H 21/04
(52) U.S. Cl. .................... 435/69.1; 435/320.1; 435/325; 435/455; 536/23.1; 536/23.5
(58) Field of Search .............................. 536/23.1, 23.5; 435/320.1, 325, 455; 800/13

(56) References Cited

FOREIGN PATENT DOCUMENTS

| WO | WO97/26371 | 7/1997 |
| WO | WO 99/00410 | 1/1999 |
| WO | WO 99/47655 | 9/1999 |

OTHER PUBLICATIONS

Stone et al., A single EFEMP1 mutation associated with both Malattia Leventinese and Doyne honeycomb retinal dystrophy, 1999, Nature Genetics, vol. 22 pp. 199–202.*
R.J. Wall, Transgenic Livestock: Progress and Prospects for the Future, 1996, Theriogenology, 45:57–68.*
Kappel et al., Regulating gene expression in transgenic animals, 1992, Current Opinion in Biotechnology, 3:548–553.*
Stephanie Viville, Mouse Genetic Manipulation via Homologous Recombination, 1997, Houdebine (eds), Harwood academic publishers, France, pp. 307–321.*
Chang, J. G. et al., "Cloning of a Portion of the Chromosomal Gene and cDNA for Human β–Fodrin, the Noneryth-roid Form of β–Spectrin", Genomics 17: 287–293 (1993).
Evans, K. et al., "Clinical Characterization and Genetic Linkage analysis in Doyne's honeycomb Retinal degeneration", Investigative Ophthalmology and Visual Science, vol. 36 No. 4: 890 (1995), Database Biosis No. 98249743.
Graff, C. et al., "Fine Mapping of Best's Macular Dystrophy Localizes the Gene in Close Proximity to But Distinct From the D11S480/ROM1 Loci", Genomics 24:425–434 (1994).
Gregory, C. Y. et al., "The Gene Responsible for Autosomal Dominant Doyne's Honeycomb Retinal Dystrophy (DHRD) Maps to Chromosome 2p16", Human Molecular Genetics 5 (7): 1055–1059 (1996).
Héon, E. et al., "Linkage of Autosomal Dominant Radial Drusen (Malattia Leventinese) to Chromosome 2p16–21)", Archives of Ophthalmology 114 (2): 193–198 (Feb. 1996).

Munier, F. L. et al., "Malattia Levantinese: exclusion of Known Disease Causing Gene Associated with Macular Dystrophies", American Journal of Human Genetics, 57(4): 333 (1995).
Small, K. W. et al., "North Carolina macular dystrophy (MCDR1). A review and refined mapping to 6q14–q 16.2", Ophthalmic Paedriatics and Genetics 14(4): 143–150 (1993).
Weber, B. H. F., "Die Genetik der Makuladegenerationen", Klinische Monatsblatter fur Augenheilkunde, vol. 210 No. 1, pp. 9–17 (Jan. 1, 1997).
Zhang, K. et al., "Genetics and Molecular Studies of Macular Dystrophies: Recent Developments", Survey of Ophthalmology, 40 (1): 51–61 (1995).
Choo et al.; "Expression of Human Blood Clothing Factor IX In Transgenic Mice: Use of a cDNA with Complete mRNA Sequence", Nucleic Acids Research, 15(3): 871–884 (1987).
Colon et al.; "Notch 1 is Required for the Coordinate Segmentation of Somites", Development, 121: 1533–1545 (1995).
Ikegawa et al.; "Structure and Chromosomal Assignment of the Human S1–5 Gene (FBNL) That is Highly Homologous to Fibrillin", Genomics 35: 590–592 (1996).
Kilpatrick et al.; "Delivery of Hammerhead Ribozyme Specifically Down–regulates the Production of Fibrillin–1 by Cultured Dermal Fibroblasts", Human Molecular Genetics 5(12):1939–1944 (1996).
Lecka–Czernik et al.; "An Overexpressed Gene Transcript in Senescent and Quiescent Human Fibroblasts Encoding a Novel Protein in the Epidermal Growth Factor–like Repeat Family Stimulates DNA Synthesis", Molecular and Cellular Biology, 15 (1): 120–128 (1995).
Montgomery, R. A. and Dietz, C. H.; "Inhibition of Fibrillin 1 Expression Using U1 snRNA as a Vehicle for the Presentation of Antisense Targeting Sequence", Human Milecular Genetics 6(4): 519–525, (1997).
Moreadith, W. R. and Radford, B. N.; "Gene Targeting in Embryonic Stem Cells: the new Physiology and Metabolism", J. Mol. Med. 75: 208–216, (1977).
Mullins, J. L. and Mullins, J. J.; "Perspectives Series: Molecular Medicine in Genetically Engineered Animals", J. Clin. Invest., 98(11): S37–S40 (supplement 1996).
Rudinger, J.; "Characteristics of the Amino Acids as Components of Peptide Hormone Sequence", Peptide Hormones, Edited by I. A. Parsons, National Institute for Medical Research Mill Hill, London, University Park Press, Baltimore, London Tokyo, pp. 5–7, (Jun. 1976).
Seamark R. F.; "Progress and Emerging Problems in Livestock Transgenesis: a Summary Perspective", Reprod. Fertil. Dev. 6: 653–657).
GenBank Accession No. u 03877, Apr. 30, 1995.
Partial International Search Report received on Jan. 5, 2001.

* cited by examiner

*Primary Examiner*—Scott D. Priebe
*Assistant Examiner*—Sumesh Kaushaz
(74) *Attorney, Agent, or Firm*—Needle & Rosenberg, P.C.

(57) ABSTRACT

Therapeutics and diagnostics based on the identification of genetic mutations, which cause Macular Degeneration (MD) are disclosed.

9 Claims, 12 Drawing Sheets

Exon 1

Currently undetermined exon 2 partial transcript

Figure 1:
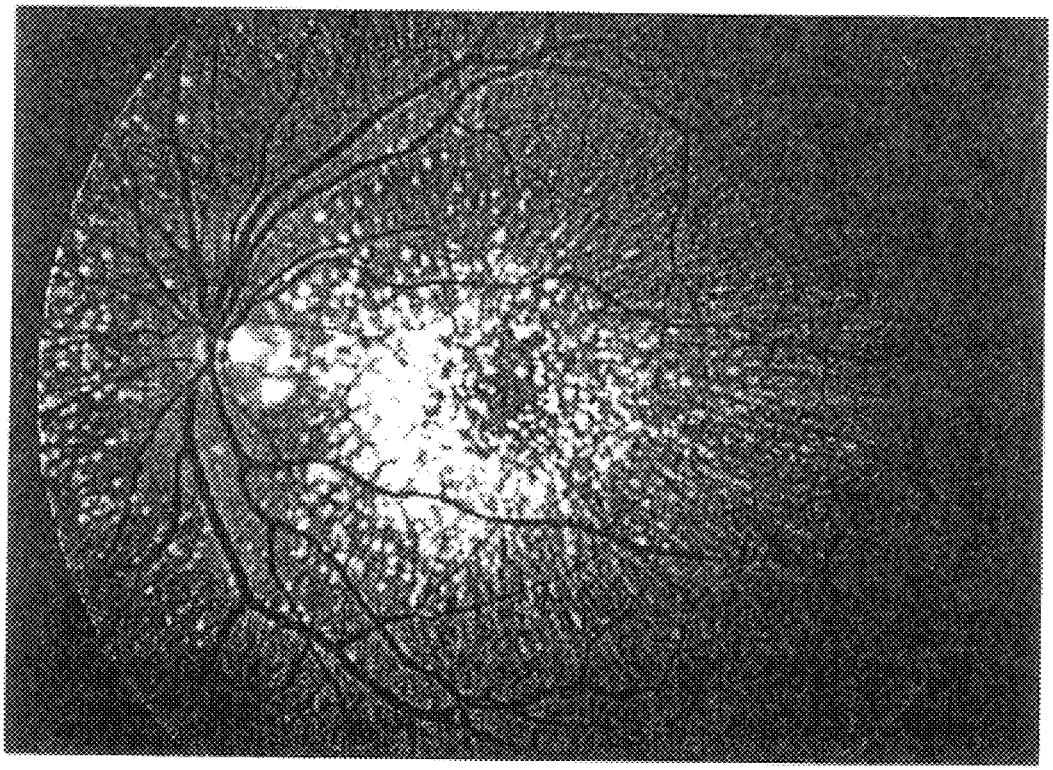

AGTGTGCGAGATTTAAGCCGCACCTGGATTCCATAGGAGCTGGTTAGAAGCTGGGACGCTGAGCAGCT
CCAGGGGACCGCCGCGTTAGCTTGCTGTTAAGAAAGGGGACCTCATCTCCCTGCCGGGCCAGGCCGCC
CGCCCGAAACTGGTACCTTGGGCTGCGGTGCGATCCCTGGTTCCGGTCCTAGGCAGCCTGAAACCGAA
GGTAGCGTGTCGGGGACCCAGACTGATAAGACAAAAGAGAATCAGTCGCTTTGGGCTGCCCCTCCACA
CAACCTGGGACTTTTAAACAAAGCTGTGCGCAGAGAAAGGCGTGGAAATGCCACTTTGAGAGTTTGTG
CTGGGGGATGTGAGAAGCTCTGAGACATGTGAGAAGGTCTAGTATTCTACTAGAACTGGAAGATTGCT
CTCCGAGTTTTGTTTTGTTATTTTGTTTAAAAAATAAAAAGCTTGAGGCCAAGGCAATTCATATTGGCT
CACAGGTATTTTTGCTGTGCTGTGCAAGGAACTCTGCTAGCTCAAG (SEQ ID No. 46)

Complete intron 2 gtgagtatac tgggaaagcc ttaacgttct agagaacaga gttttgcagccccacctcca
tcccccgggg tgtgggactg gggggcagga aatgcaccgtccccttttgaa atggattact
gttttttcct ttcgaccccc tctttctgcagcctgctttg taggtgcagt ataaaatgca
cgctgaatgt cttttgtatgtaaacagcgt agcaggatgg agtaacgtga aatgcaattc
tacagcagttttttacgtctt tgctgcctcg ttcgttggct accgagaagg ttcaggagggggaggggaga
tgagaaagca gattggaagt tgagtatggt ggtagcctcagcctctccca ccctcctttc
ctcgcttgtg ctcactgcta aagttttgttactttccccg cagcagatac taaacattag
tttgtcctgt attttctttgag (SEQ ID No. 47)

Exon 3

ATTCACAATG TTGAAAGCCC TTTTCCTAAC TATGCTGACT CTGGCGCTGG TCAAGTCACA
GGACACCGAA GAAACCATCA CGTACACG (SEQ ID No. 48)

Start intron 3 gtaagggtg atggaatttg aaataagtac ggttcagcgg gattctgtgacaaaaaaga ctttacacac
ccctgccagt gtatttgggc tatactctgctgagggtgat aaattaaaca acacttcatt catgcttcat
atctaagattcgttgtaaat tgccccttg atcctttcaa aagttcattg ggctcaccacctaagatagg
aaccaacatg taatcatttg tgcagggcta aaaatgggatccgttcaaaa actaaaacca aagaaagtta
catgtttcca aaacattcaacaaattaatg ggtgtaagga actggaaaac ctggactcct
accacatgcagataaaacca atacgtgcag aataagactc aagtcaagta agaacgttaaacaccataaa
gacacatggccttctttgtgtacatgacatgcattctcaagtaagtggcctttattgaatttataaaggctata
tattcattcttttgtataacttg ataattctaataaataaaggcagacaacagtttatgtgttaccaggatg
catattggctaaagtggttttaaaacgtaatgtgtgcaactccgttttgcattttctaattagcgtct
ctgatatttccaagtaatatttgattagttagttgcataggtgtaaccaatgtttaataaaatattaaaaagat
cacctgaccctcccactgctacaaatagttgtggtgagaac agagaaggacagtactgacttcacttctggt
gagtttgtttgcacctctgttctgtgttttcttgtctttaatcagtgttaggcaaatgacatttgtcctggatt
ggaatatgaaaa gcacattttttctactgctcccagtttaaaattaagtaatcctactcgaaagaatgtgaaa
aattttttgaaaagaaaactcttaaaaatgaactaatgtcaattactgataataaac attatctcacttttttgg
taccacattatccctagaatgttagtattcatctggcaaatgttccttttctgttgttcagatccactataaat
aaaatagcttaatacaaatattttgttaact tcatgttaaatgcagttgcttcctctgctgaagataaattaa
gcaagaaaaatgaaggcatgtgctgkttatcttaaaatgaaaatgktttgktattcagactaaacttactgcc
ttctcangggagctaaaattaaattcactacccacttttataatcatctcataaaagattttacttcttttcca
gttgc (SEQ ID No. 49)

FIG. 5A

End intron 3 aaaatgcctg gttttcagaa gggggtycc ataggctgtt tgttcagnggggngctaar gaggnnattt
gaagctgggg actgttnggg ggaaccccnctgttcctttg gagcttaant tanggagcng gtcagggggg
gaaanggaggggctttaatn ctgtnanagg ntttnaaaaa aaaaaaaaaa ntccngggctggttnggggt
gggggnggggg gaaagggcca agaaaaaaaa aaaaaatggtntttttttttt tttaacattt ccaatgtggg
aaaaaaggca aattaataaagagcagtcag agaagttgga gaagattagt ctcaaaacag
aaaagaagatggtactgggc anctgtacca aaaagaacag aagagtttag gcagctgatggttgagaatg
gaccccccgaa gctgtccaat gcacagactt gtcttttgaaaaaaaagcga tagaatgtta aaccacccat
ctcatcatat atctaggactttagcacaag gattgttgcc ataagaatga agcttttaga
gtgatttcttagggaatgga cacaccaatt aactgtctcc tggccccacc tttgatgttttcttcacag
(SEQ ID No. 50)

Exon 4

CAATGCACTG ACGGATATGA GTGGGATCCT GTGAGACAGC AATGCAAAG (SEQ ID No. 51)

complete intron 4 gtgagccagcttcaaagacttccatgtgatcattgccttctgtctccatctcttgtgtcactcttcctgtcctgt
ctgtgttataccaaaaaggcatgagcattatatttacatgtttgattttccctcttagaarattcctgacttat
tttattactgaccacag (SEQ ID No. 52)

Exon 5

ATATTGATGA ATGTGACATT GTCCCAGACG CTTGTAAAGG TGGAATGAAG TGTGTCAACC
ACTATGGAGG ATACCTCTGC CTTCCGAAAA CAGCCCAGAT TATTGTCAAT AATGAACAGC
CTCAGCAGGA AACACAACCA GCAGAAGGAA CCTCAGGGGC AACCACCGGG GTTGTAGCTG
CCAGCAGCAT GGCAACCAGT GGAGTGTTGC CCGGGGGTGG TTTTGTGGCC AGTGCTGCTG
CAGTCGCAGG CCCTGAAATG CAGACTGGCC GAAATAACTT TGTCATCCGG CGGAACCCAG
CTGACCCTCA GCGCATTCCC TCCAACCCTT CCCACCGTAT CCAGTGTGCA GCAGGCTACG
AGCAAAGTGA ACACAACGTG TGCCAAG (SEQ ID No. 53)

Start intron 5

Gtaggaataacttatttttcctaacccattgaaagctgcaggagaaccccccatgaagcttgaattcggatcca
cgttg (SEQ ID No. 54)

End intron 5

Ttttggcattctgaaattttgcaatgaaagatttatacawacatgttgccctgctgtttggcaaaaaacaaacagc
tacmggggraacggtataatattaaaggttgatwacacccagttattggttagatttttagaaatttgtcaatgga
aattatctcaaatacaatatattggatggaaaagcaagtatcatacaatctattaaaattttttaacatacaaaac
aataccatatgttctaatggatgcatccctgtctaacaaaagtacaaaaacatctcagggaaggattcattccta
ccgagacagtggtagctgatgggtcaagggatgaggatggtgtgaggctttagctgtatctgaaatgtttcttaa
caaaacaaaatgagccaagaccaacatgacaaaatgttagcatttgttaaatctgagcagtactcactggtatt
gcaaaattatttttctgaacacttgaaataatttataattttaaacattttccaatgcaagaacattataaacttt
aagaataaagtwaaaatttagcttaagaagtggcmaaatggargaaatatcaacatcttcacaactgacaatyyt
tytstgtgctwgyatgtctswgacag (SEQ ID No. 55)

Exon 6

ACATAGACGA GTGCACTGCA GGGACGCACA ACTGTAGAGC AGACCAAGTG TGCATCAATT
TACGGGGATC CTTTGCATGT CAGTGCCCTC CTGGATATCA GAAGCGAGGG GAGCAGTGCG TAG
(SEQ ID No. 56)

FIG.5B

Start intron 6

Gtaagtaccacagtgcagtgagcacggtcctgtcttgagtaccttaactgtttcaacctcaagcattccaatc
aaagcattcatgtttctttggagagtggtagccaataattccttattttttatagactaccaatccattttc
cacaataacaagaaacaaccttaaaggttgaggcaggagaaccccatgaagcttgaattc
(SEQ ID No. 57)

End intron 6

Aaactgacatcttatatatatatgcaatagtctcaattattttgttttctttaaatctcaatccacccaccaa
gtttatttaccactgaatggcatgaacattgagtctttgttcttaacttcttaactcagaatacaaagtatat
ttaaaatacatataccctaattttaacaaaataggaaattattacttttaaaaagagattttctctacatagg
ttttctagataatgcttttcagagaatgctaattcaataatttggttctctttgtgtgtgtgcctgataacctag
(SEQ ID No. 58)

Exon 7

ACATAGATGA ATGTACCATC CCTCCATATT GCCACCAAAG ATGCGTGAAT ACACCAGGCT
CATTTTATTG CCAGTGCAGT CCTGGGTTTC AATTGGCAGC AAACAACTAT ACCTGCGTAG
(SEQ ID No. 59)

Start intron 7

Gtaagccttttgagaacttgctgatttctgtcttcacaaaaggaaacccccatgccatgttgcagtatttccagt
tttctatgttcttgagtaaatagtttccatcgacttcccttcagcaatcataaagytgcaggagaaccccatga
agcttgaattcggatccacgtgg (SEQ ID No. 60)

End intron 7 aaactttcccactgaaagtgcattcttgattttacatgcctttttytcccctttcagaaatgcaatgtcacgg
:cacaacaattaaaagattggcatgacatgggaaaaaa:tctagtgtrggaaaaatgccttttcaacaatattt
t:cagtgctttagaagcattgcaaaactccgtatgggttctcaaaggcttatgttataattgtaatggaattta
acagaacccatttaaaaaagttaataa:atagccacagataaatcttccagtaccagcattgcctgaagaagac
catatccagtataagttgtcttatawcaattatttatagaaattggcattttgtwtcttgaaccaacaaaagaa
aaatccgaat:mccggaaktgttatatttwttagaagcattaaattcctttgganagattnatcacacatcnna
ctaactgtcattcctagaaaaaatatttcggtatttccnaaagaagtatatgacagacgtttgtagttgttccc
acaaatatganaccnaaatggatgttctccagtgagcttctgcagggcaaataattcagctagggaattactca
cttgtcagcagatgacgtaggtacaaaagagtaaggatatgtttaaagtstaymtatatmtgtgtgtataya
tatacatatacaymwmymtatayatamratttttttcwag (SEQ ID No. 61)

Exon 8

ATATAAATGA ATGTGATGCC AGCAATCAAT GTGCTCAGCA GTGCTACAAC ATTCTTGGTT
CATTCATCTG TCAGTGCAAT CAAGGATATG AGCTAAGCAG TGACAGGCTC AACTGTGAAG
(SEQ ID No. 62)

FIG.5C

Start intron 8 gtaaaactcttcccagatagtatggaataaagtccaattcctgtgactgctgttgttttatctgattatgta
cccatttatgaaaacaaacgcttacccatgggaattctgttctaaaatccagttaatgtagttcagttgtta
cattgccttttagtgtgttaccaagaaaaaggaaaagaaataaaaataactgaaatattaggtgcaggctg
gctctaataattagaaagggtgctctagcatgttgcgtctcagtgtgttatccagtgaccaggtatgtcagc
acctcctgggagcttatgagaaatgcagaatctcaggctgcaacccagacctcctgagtctgaatctacatt
caacaaaaactgcaggtgactggtgtgcacatttaagtttcagaatagccaagtgcatgtcaaaacattaaa
ataaaaatcaggagatctggtttctggttctattcctgctactgtgtgacttgggcacatttcttgagttgc
ctgggtttcactttccacatgaacaagaggagggccatttaactagattcatgaccttcagggtccattgca
tgtgcacatttcgttatataattcaaaaggcattagacatcctgaggggatgccacagacacttgatgtcc
ctgacctcctcacggttcactcagctttacacaaagctcaaaccccaccgagagaggcctcacatcatgcca
ttacactcaaaactgaaagaggctacctcaggacagctgcctctgcccttctgagtaaactgtagggacatc
actattcagaaatgcaaagcattcttcccctgaaagtcagatcctgccaagctgtcattctggaagcttgca
caggttaggggacttggcattcaaagctcaaatgaacttggcttcaaagtcacccaatttctgagaagacaa
acatgaactctacatcctggatgggtctgcagagtccaaaatgaaggccgtcaaccacaagccaattcattc
agtagtgtagttaggtccaggattagccaaattgtcagcaatgattcagtaaaagtcatgataagaaaaact
ttttgtgctatgaagtcatagagggaaataagctgatattgttagaatttgccttttagctgcttataaagt
tttgtatttctatttcagaatttgcaatatttttactctctttagctcacctcaaaagtgtattactt
cctctggactgttgagcagaaca (SEQ ID No. 63)

End intron 8

Aaaaaaatatatatgtgtgtgtgtgtgtgtgtgtgtgtgtatattaaacccagncaacttaaaaaatgt
gcccaagtcacacagtcgcaggaataggacaanaagccagatctctttatatatatataggta.gatataattt
ttcctccttanaatataaataa.ttttaattatatataattattttaatatagatattttaaatcttataattt
atatatatatataatttatatatatatatatatccaaagtagtggtgcacaaactttttcaactctgtgtccttt
tctcttgtctaattcaacag (SEQ ID No. 64)

Exon 9

ACATTGATGA ATGCAGAACC TCAAGCTACC TGTGTCAATA TCAATGTGTC AATGAACCTG GGAAATTCTC
ATGTATGTGC CCCCAGGGAT ACCAAGTGGT GAGAAGTAGA ACATGTCAAG
(SEQ ID No. 65)

Start intron 9 gtaagtttatttttttttcatatgttaggtatttagttttagccaggaagagacaagaggaagttataggatt
ctcctatagactttcattttcccactttcaatatacaatttaagctnttttttcccctgttcatcataaaata
tatacatctcataaagaggggattctatgctaangccgacntttttcgtccttaaaagataaataattttaata
aaatattgatatgtattctatgtaacctacatcatctnttgagatacatcttcaaatcatccactggaaaaga
ttcagttattaaaangtttcacctgtgagtttgagtttanagcataagctcaatatgggagttaaacatacctc
catccagtcttagccctctaaaacncanggattataaattgcgtaaaaatgtaggtgctgaaaaaagtcagcct
aatatgttgtaaaatatagttgaatattttagagaaaactactagccccaaaatagctaatgaccttgggtcca
gtttcaaaataaacattcagatgatcttcacacctatacgtaagkggaagaggcagctccccacaatggtatga
tttcagagtttctcaggaagatctaaaaaaaaaaaggaccctacctccaatgttgcatgtagttgaaaattttc
ttaacagggaaaggactgtcanataaaaccaaaaacgtaaaaaatcctggaaaagctagtncaaacncttaaat
ttacncaaagcaccaaaagaatgaaaaaatgaccaancttgacanaaaacctgtttgaatcccagctccactgt
nttcagtctgcncaatnttgaacaaattatcaaactactntgagcctcagnttcctcatttggaaaagggagtt
gggggaatttaggggaatancatncntaaaaatantttgtaaactataaagcttgtncaggtcaagggggttttt
atnaaatttac (SEQ ID No. 66)

FIG.5D

End of intron 9

Agcctcttccttaacttcctctttttccttacagtcctaaaattgctatgctctatgaggtggaacacttcata
gtttcacttcctgtgctgtgcttcctctggacagtataatccactcccagcatgcttcagcttactgaaaccag
atttctagcctttacctttctcccaagttcctgaaagagatgataagctgccctccatagtttatgcttcctga
tttctcagcttggaaagccttccctgccccagccatgaaaactccatctaaccaccacccttcaaggccacgtt
gagatgcctcttccttccttcagccttccctaatcccctggcaaaattacccaactctgctccacatgcccca
gtatacttatctatctcttacttaattccattttactttctaagtaatcatatacacattccctcaattataat
gtccctgatgacaagaactggtgtttaacttttatataggcagagtcagtggttaacattggggtttgaattca
acagatgaacaataggtgcttgataaaatatcatgaaatgacacatattaatctgcctagaatgtctcagctct
gtctgtcctgaattcaatacaatgaacacccagtcttgtgtctaaaagcaggttgaacacagtccagatgctct
cacacctccttccttgcaaacagaatctgccagttatatgatttaattagatcagttcattagtttagttagta
aactctttgaccctacatctctacag (SEQ ID No. 67)

Exon 10

ATATAAATGA GTGTGAGACC ACAAATGAAT GCCGGGAGGA TGAAATGTGT TGGAATTATC
ATGGCGGCTT CCGTTGTTAT CCACGAAATC CTTGTCAAGA TCCCTACATT CTAACACCAG AGAA
(SEQ ID No. 68)

intron 10 gtaagaaaaa tcagaactttt tgaaagtgag gattttctgg tcttaccaagccaaactgct gaatactttt
gtttgtctct gcag
(SEQ ID No. 69)

Exon 11

CCGATGTGTT TGCCCAGTCT CAAATGCCAT GTGCCGAGAA CTGCCCCAGT CAATAGTCTA
CAAATACATG AGCATCCGAT CTGATAGGTC TGTGCCATCA GACATCTTCC AGATACAGGC
CACAACTATT TATGCCAACA CCATCAATAC TTTTCGGATT AAATCTGGAA ATGAAAATGG
AGAGTTCTAC CTACGA (SEQ ID No. 70)

Start intron 11 gtaagtatcc tgaaggcagc cttaactatt gagaaagatg ggagtttgttgttgttgttg ttgttgttgt
tgttgtgtgg tatccacatg tggaaggaaagcaaacattt aaaagtgtcttnatgtgtaggcattgtgtaag
gccttccagctacattatttcatttattcctcttggtaacactgccagatagatattaatattcatctccatttt
ttacagaggagaaaagtgagatgcagaaagattaagtagcatccctgaaatcactcaaatattaagtttggcaga
ctctgatagagttgtgtgtgaccacgaaaatacaagcctcccatcccccgcctctgcccccacccaacatacc
cccaagtaggtatcactaatcattgatggttaattaattatacatagacatacatataattcaaacccaaaataa
ttcctggagctcctaaagagttttcagacatcatgaattcatcattgttacattcacaagacagtttgtgttca
caccgaaactaaaacctataagtatgtgagaagtgaccccacctccccgcacagtatgtgtcaagtagttgtacc
ttcttgccaacttctgggctggcagtatggagtcatctccctatctttcattgcctgtgtgaaatctactttctg
aattctgccatttccctcttcacactgtctcctgggttatctttgcttcctcacatccctatctctcttcctata
aactggctcccgtcacttccatgatcccttcagtggcttctgagctggtctccctgaccccaaagcctcagcctt
ccagtctccctacaaaatctcagcaagttcattttaaggttaaaatttggacatattttaaatacggctcaccac
ttcatgtgaaaatgatggcaccctaccaagcagtttgcagagttaccggtaactgtttcatgctaatgatgttay
tcatccagttac SEQ ID No. 71)

End intron 11

Tcccttttttttttcyttctaaaaaggnaaccnatggcccaagnttgnaaaaanaaaaagggccncttttgnttt
ccaggtttaaaaatttccnattttcccctwaagtttagkttttggaaaggcccccacttcnccannaaaaggaa
aaaaaatgnttacmaanaggggggggattcaaaacnaaaaacttttttaaaaaaaaaaaaaagcaagtccttgaa
acttggagctaatgactgtattagacaagggataagagccaagaagagttgaaaccaagaagggaccaagtagt
ggctcttttataccaccttcaaaattctcccccctaattcttataggaggtatactaacaaagcatagaaactcc
aatccaagaaaattattctcttcctttctctatttctctttttattttag (SEQ ID No. 72)

FIG.5E

Exon 12

CAAACAAGTC CTGTAAGTGC AATGCTTGTG CTCGTGAAGT CATTATCAGG ACCAAGAGAA
CATATCGTGG ACCTGGAGAT GCTGACAGTC AGCAGTATAG GGACCTTCCG CACAAGCTCT
GTGTTAAGAT TGACAATAAT AGTGGGGCCA TTTTCATTTT AG (SEQ ID No. 73)

3' utr tcttttctaa gagtcaacca caggcattta agtcagccaa agaatattgt taccttaaag
cactatttta tttatagata tatctagtgc atctacatct ctatactgta cactcaccca
taacaaacaa ttacaccatg gtataaagtg ggcatttaat atgtaaagat tcaaagtttg
tctttattac tatatgtaaattagacatta atccactaaa ctggtcttct tcaagagagc
taagtataca ctatctggtg aaacttggat tctttcctat aaaagtggga ccaagcaatg
atgatcttct gtggtgctta aggaaactta ctagagctcc actaacagtc tcataaggag
gcagccatca taaccattga atagcatgca agggtaagaatgagttttta actgctttgt
aagaaaatgg aaaaggtcaa taaagatatatttctttaga aaatggggat ctgccatatt
tgtgttggtt tttattttcatatccagcct aaaggtggtt gtttattata tagtaataaa
tcattgctgtacaacatgct ggtttctgta gggtattttt aattttgtca gaaatttttagattgtgaata
ttttgtaaaa aacagtaagc aaaattttcc agaattcccaaaatgaacca gatacccct agaaaattat
actattgaga aatctatggggaggatatga gaaaataaat tccttctaaa ccacattgga
actgacctgaagaagcaaac tcggaaaata taataacatc cctgaattca ggcattcacaagatgcagaa
caaatggat aaaaggtatt tcactggaga agttttaatttctaagtaaa atttaaatcc taacacttca
ctaatttata actaaaatttctcatcttcg tacttgatgc tcacagagga agaaaatgat
gatggtttttattcctggca tccagagtga cagtgaactt aagcaaatta ccctcctacccaattctatg
gaatatttta tacgtctcct tgtttaaaat ctgactgctttactttgatg tatcatattt ttaaataaaa
ataaatattc ctttagaagatcactctaaaa
(SEQ ID No. 74)

FIG.5F

```
            M LKALFLTMLTL ALVKSQDTE  ETITYTQCTD  GYEWDPVRQQ
CKDIDECDIV  PDACKGGMKC   VNHYGGYLCL  PKTAQIIVNN  EQPQQETQPA
EGTSGATTGV  VAASSMATSG   VLPGGGFVAS  AAAVAGPEMQ  TGRNNFVIRR
NPADPQRIPS  NPSHRIQCAA   GYEQSEHNVC  QDIDECTAGT  HNCRADQVCI
NLRGSFACQC  PPGYQKRGEQ   CVDIDECTIP  PYCHQRCVNT  PGSFYCQCSP
GFQLAANNYT  CVDINECDAS   NQCAQQCYNI  LGSFICQCNQ  GYELSSDRLN
CEDIDECRTS  SYLCQYQCVN   EPGKFSCMCP  QGYQVVRSRT  CQDINECETT
NECREDEMCW  NYHGGFRCYP   RNPCQDPYIL  TPENRCVCPV  SNAMCRELPQ
SIVYKYMSIR  SDRSVPSDIF   QIQATTIYAN  TINTFRIKSG  NENGEFYLRQ
TSPVSAMLVL  VKSLSGPREH   IVDLEMLTVS  SIGTFRTSSV  LRLTIIVGPF
SF (SEQ ID NO.: 2)
```

FIG.6

SEQUENCE LISTING

<160> NUMBER OF SEQ ID NOS: 74

<210> SEQ ID NO 1
<211> LENGTH: 493
<212> TYPE: PRT
<213> ORGANISM: Homo sapiens

<400> SEQUENCE: 1

```
Met Leu Lys Ala Leu Phe Leu Thr Met Leu Thr Leu Ala Leu Val Lys
 1               5                  10                  15

Ser Gln Asp Thr Glu Glu Thr Ile Thr Tyr Thr Gln Cys Thr Asp Gly
            20                  25                  30

Tyr Glu Trp Asp Pro Val Arg Gln Gln Cys Lys Asp Ile Asp Glu Cys
        35                  40                  45

Asp Ile Val Pro Asp Ala Cys Lys Gly Gly Met Lys Cys Val Asn His
    50                  55                  60

Tyr Gly Gly Tyr Leu Cys Leu Pro Lys Thr Ala Gln Ile Ile Val Asn
65                  70                  75                  80

Asn Glu Gln Pro Gln Gln Glu Thr Gln Pro Ala Glu Gly Thr Ser Gly
                85                  90                  95

Ala Thr Thr Gly Val Val Ala Ala Ser Ser Met Ala Thr Ser Gly Val
            100                 105                 110

Leu Pro Gly Gly Gly Phe Val Ala Ser Ala Ala Ala Val Ala Gly Pro
        115                 120                 125

Glu Met Gln Thr Gly Arg Asn Asn Phe Val Ile Arg Arg Asn Pro Ala
    130                 135                 140

Asp Pro Gln Arg Ile Pro Ser Asn Pro Ser His Arg Ile Gln Cys Ala
145                 150                 155                 160

Ala Gly Tyr Glu Gln Ser Glu His Asn Val Cys Gln Asp Ile Asp Glu
                165                 170                 175

Cys Thr Ala Gly Thr His Asn Cys Arg Ala Asp Gln Val Cys Ile Asn
            180                 185                 190

Leu Arg Gly Ser Phe Ala Cys Gln Cys Pro Pro Gly Tyr Gln Lys Arg
        195                 200                 205

Gly Glu Gln Cys Val Asp Ile Asp Glu Cys Thr Ile Pro Pro Tyr Cys
    210                 215                 220

His Gln Arg Cys Val Asn Thr Pro Gly Ser Phe Tyr Cys Gln Cys Ser
225                 230                 235                 240

Pro Gly Phe Gln Leu Ala Ala Asn Asn Tyr Thr Cys Val Asp Ile Asn
                245                 250                 255

Glu Cys Asp Ala Ser Asn Gln Cys Ala Gln Gln Cys Tyr Asn Ile Leu
            260                 265                 270
```

```
Gly Ser Phe Ile Cys Gln Cys Asn Gln Gly Tyr Glu Leu Ser Ser Asp
            275                 280                 285
Arg Leu Asn Cys Glu Asp Ile Asp Glu Cys Arg Thr Ser Ser Tyr Leu
        290                 295                 300
Cys Gln Tyr Gln Cys Val Asn Glu Pro Gly Lys Phe Ser Cys Met Cys
305                 310                 315                 320
Pro Gln Gly Tyr Gln Val Val Arg Ser Arg Thr Cys Gln Asp Ile Asn
                325                 330                 335
Glu Cys Glu Thr Thr Asn Glu Cys Arg Glu Asp Glu Met Cys Trp Asn
            340                 345                 350
Tyr His Gly Gly Phe Arg Cys Tyr Pro Arg Asn Pro Cys Gln Asp Pro
        355                 360                 365
Tyr Ile Leu Thr Pro Glu Asn Arg Cys Val Cys Pro Val Ser Asn Ala
    370                 375                 380
Met Cys Arg Glu Leu Pro Gln Ser Ile Val Tyr Lys Tyr Met Ser Ile
385                 390                 395                 400
Arg Ser Asp Arg Ser Val Pro Ser Asp Ile Phe Gln Ile Gln Ala Thr
                405                 410                 415
Thr Ile Tyr Ala Asn Thr Ile Asn Thr Phe Arg Ile Lys Ser Gly Asn
            420                 425                 430
Glu Asn Gly Glu Phe Tyr Leu Arg Gln Thr Ser Pro Val Ser Ala Met
        435                 440                 445
Leu Val Leu Val Lys Ser Leu Ser Gly Pro Arg Glu His Ile Val Asp
    450                 455                 460
Leu Glu Met Leu Thr Val Ser Ser Ile Gly Thr Phe Arg Thr Ser Ser
465                 470                 475                 480
Val Leu Arg Leu Thr Ile Ile Val Gly Pro Phe Ser Phe
                485                 490

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 2
gttttgttac tttccccgca                                              20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 3
actggcaggg gtgtgtaaag                                              20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 4
ccaattaact gtctcctggc                                              20
```

```
<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 5
aaggcaatga tcacatggaa g                                              21

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 6
catgtttgat ttttccctct tagaa                                          25

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 7
atgctgctgg cagctacaac c                                              21

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 8
aacctcaggg gcaaccac                                                  18

<210> SEQ ID NO 9
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 9
ttcaatggtt aggaaaagaa gttattc                                        27

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 10
tgacaattct ttctgtgttg cat                                            23

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Primer
```

<400> SEQUENCE: 11
ctcaagacag gaccgtgctc                          20

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 12
ttctctttgt gtgtgtgcct g                        21

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 13
tggggtttcc ttttgtgaag                          20

<210> SEQ ID NO 14
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 14
caaaagagta aggatatgtt taaagtc                  27

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 15
ggactttatt ccatactatc tggg                     24

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 16
tggtgcacaa acttttcaac tc                       22

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 17
tcctcttgtc tcttcctggc                          20

<210> SEQ ID NO 18
<211> LENGTH: 20

```
<212> TYPE: DNA
<213> ORGANISM: Artificial Sequence
<220> FEATURE:
<223> OTHER INFORMATION: Description of Artificial Sequence: Primer

<400> SEQUENCE: 18
cttgcaaaca gaatctgcca                                                 20

<210> SEQ ID NO 19
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 19
tcctcacttt caaaagttct gattt                                           25

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 20
accaagccaa actgctgaat                                                 20

<210> SEQ ID NO 21
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 21
aaaagtattg atggtgttgg ca                                              22

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 22
tgccatcaga catcttccag                                                 20

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 23
aatgtttgct ttccttccac a                                               21

<210> SEQ ID NO 24
<211> LENGTH: 23
<212> TYPE: DNA
<213> ORGANISM: Artificial Sequence
<220> FEATURE:
<223> OTHER INFORMATION: Description of Artificial Sequence: Primer
```

<400> SEQUENCE: 24
gcatagaaac tccaatccaa gaa                                          23

<210> SEQ ID NO 25
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 25
tgcctgtggt tgactcttag aa                                           22

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 26
ggaacaagca ggacctttca                                              20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 27
tgttatatcc tatttgagct                                              20

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 28
atcctagcaa aacataagag t                                            21

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 29
cttacattcc tgtggacttg a                                            21

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 30
cggggatctt tttcatgatg                                              20

<210> SEQ ID NO 31
<211> LENGTH: 19

```
<212> TYPE: DNA
<213> ORGANISM: Artificial Sequence
<220> FEATURE:
<223> OTHER INFORMATION: Description of Artificial Sequence: Primer

<400> SEQUENCE: 31
ggggcaaggc aagagtaag                                                19

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 32
ctgcagtgag ctgcgattat                                               20

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 33
ttttgctttg ggaattagca g                                             21

<210> SEQ ID NO 34
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 34
ggaggttgca gtgagctg                                                 18

<210> SEQ ID NO 35
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 35
ttgaattgtc gtgaatcttg tt                                            22

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 36
taccactgca ctgaagcctg                                               20

<210> SEQ ID NO 37
<211> LENGTH: 24
<212> TYPE: DNA
<213> ORGANISM: Artificial Sequence
<220> FEATURE:
<223> OTHER INFORMATION: Description of Artificial Sequence: Primer
```

-continued

```
<400> SEQUENCE: 37
aaatcttctg caaaaacaaa agtg                                              24

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 38
ccaattaact gtctcctggc                                                   20

<210> SEQ ID NO 39
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 39
tttgtgcacc actactttgg a                                                 21

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 40
aaatgtgccc aagtcacaca                                                   20

<210> SEQ ID NO 41
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 41
tttgaaactg gacccaagg                                                    19

<210> SEQ ID NO 42
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 42
agcataagct caatatggga gt                                                22

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 43
tggcagtgtt accaagagga                                                   20

<210> SEQ ID NO 44
<211> LENGTH: 22
```

<212> TYPE: DNA
<213> ORGANISM: Artificial Sequence
<220> FEATURE:
<223> OTHER INFORMATION: Description of Artificial Sequence: Primer

<400> SEQUENCE: 44
caacaccatc aatactttc gg                                             22

<210> SEQ ID NO 45
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 45
aaggcaatga tcacatggaa g                                             21

<210> SEQ ID NO 46
<211> LENGTH: 523
<212> TYPE: DNA
<213> ORGANISM: Homo sapiens

<400> SEQUENCE: 46
agtgtgcgag atttaagccg cacctggatt ccataggagc tggttagaag ctgggacgct    60
gagcagctcc aggggaccgc cgcgttagct tgctgttaag aaagggggacc tcatctccct  120 gccgggccag gccgcccgcc cgaaactggt accttgggct gcggtgcgat ccctggttcc  180
ggtcctaggc agcctgaaac cgaaggtagc gtgtcgggga cccagactga taagacaaaa  240
gagaatcagt cgctttgggc tgcccctcca cacaacctgg gactttttaaa caaagctgtg  300 cgcagagaaa ggcgtggaaa tgccactttg agagtttgtg ctgggggatg tgagaagctc  360
tgagacatgt gagaaggtct agtattctac tagaactgga agattgctct ccgagttttg  420
ttttgttatt ttgtttaaaa aataaaaagc ttgaggccaa ggcaattcat attggctcac  480 aggtatttt gctgtgctgt gcaaggaact ctgctagctc aag                     523

<210> SEQ ID NO 47
<211> LENGTH: 452
<212> TYPE: DNA
<213> ORGANISM: Homo sapiens

<400> SEQUENCE: 47
gtgagtatac tgggaaagcc ttaacgttct agagaacaga gttttgcagc cccacctcca    60
tcccccgggg tgtgggactg ggggggcagga atgcaccgt cccctttgaa atggattact  120
gttttttcct ttcgaccccc tctttctgca gcctgctttg taggtgcagt ataaaatgca  180
cgctgaatgt cttttgtatg taaacagcgt agcaggatgg agtaacgtga atgcaattc   240 tacagcagtt tttacgtctt tgctgcctcg ttcgttggct accgagaagg ttcaggaggg  300 ggagggggaga tgagaaagca gattggaagt tgagtatggt ggtagcctca gcctctccca  360
ccctcctttc ctcgcttgtg ctcactgcta aagttttgtt actttccccg cagcagatac  420
taaacattag tttgtcctgt attttctttg ag                                 452

<210> SEQ ID NO 48
<211> LENGTH: 88
<212> TYPE: DNA
<213> ORGANISM: Homo sapiens

<400> SEQUENCE: 48

```
attcacaatg ttgaaagccc ttttcctaac tatgctgact ctggcgctgg tcaagtcaca    60
ggacaccgaa gaaaccatca cgtacacg                                      88
```

<210> SEQ ID NO 49
<211> LENGTH: 1289
<212> TYPE: DNA
<213> ORGANISM: Homo sapiens
<220> FEATURE:
<223> OTHER INFORMATION: "n" bases at various positions throughout the
      sequence may be a, t, c, g, other or unknown

<400> SEQUENCE: 49

```
gtaagggggtg atggaatttg aaataagtac ggttcagcgg gattctgtga caaaaaaga    60
ctttacacac ccctgccagt gtatttgggc tatactctgc tgagggtgat aaattaaaca   120
acacttcatt catgcttcat atctaagatt cgttgtaaat tgccccttg atcctttcaa   180
aagttcattg ggctcaccac ctaagatagg aaccaacatg taatcatttg tgcagggcta   240
aaaatgggat ccgttcaaaa actaaaacca agaaagtta catgttttcca aaacattcaa   300
caaattaatg ggtgtaagga actggaaaac ctggactcct accacatgca gataaaacca   360
atacgtgcag aataagactc aagtcaagta agaacgttaa acaccataaa gacacatggc   420
cttcttttgtg tacatgacat gcattctcaa gtaagtggcc tttattgaat ttataaaggc   480
tatatattca ttcttttttgt ataacttgat aattctaata aataaaggca gacaacagtt   540
tatgtgttac caggatgcat attggctaaa gtggttttaa aacgtaatgt gtgcaactcc   600
gtttttgcatt ttctaattag cgtctctgat atttccaagt aatatttgat tagttagttg   660
cataggtgta accaatgttt aataaaatat taaaaagatc acctgacccc tcccactgct   720
acaaatagtt gtggtgagaa cagagaagga cagtactgac ttcacttctg gtgagttttgt   780
ttgcacctct gttctgtgtt ttcttgtctt taatcagtgt taggcaaatg acatttgtcc   840
tggattggaa tatgaaaagc cattttttct actgctccca gtttaaaatt aagtaatcct   900
actcgaaaga atgtgaaaaa ttttttgaaaa gaaaactctt aaaaatgaac taatgtcaat   960
tactgataat aaacattatc tcacttttttg gtaccacatt atccctagaa tgttagtatt  1020
catctggcaa atgttccttt ctgttgttca gatccactat aaataaaata gcttaataca  1080
aatatttttgt taacttcatg ttaaatgcag ttgcttcctc tgctgaagat aaattaagca  1140
agaaaaatga aggcatgtgc tgkttatctt aaaatgaaaa tgktttgkta ttcagactaa  1200
acttactgcc ttctcanggg agctaaaatt aaattcacta cccacttttta taatcatctc  1260
ataaaagatt ttacttcttt tccagttgc                                   1289
```

<210> SEQ ID NO 50
<211> LENGTH: 609
<212> TYPE: DNA
<213> ORGANISM: Homo sapiens
<220> FEATURE:
<223> OTHER INFORMATION: "n" bases at various positions throughout the
      sequence may be a, t, c, g, other or unknown

<400> SEQUENCE: 50

```
aaaatgcctg gttttcagaa ggggggtycc ataggctgtt tgttcagngg gggngctaar    60
gaggnnattt gaagctgggg actgttnggg ggaacccccnc tgttcctttg gagcttaant   120
tanggagcng gtcagggggg gaaanggagg ggctttaatn ctgtnanagg ntttnaaaaa   180
aaaaaaaaaa ntccngggct ggttngggggt ggggngggg gaaagggcca agaaaaaaaa   240
```

| | |
|---|---|
| aaaaaatggt ntttttttt tttaacattt ccaatgtggg aaaaaaggca aattaataaa | 300 |
| gagcagtcag agaagttgga gaagattagt ctcaaaacag aaagaagat ggtactgggc | 360 |
| anctgtacca aaaagaacag aagagtttag gcagctgatg gttgagaatg gaccccgaa | 420 |
| gctgtccaat gcacagactt gtcttttgaa aaaaagcga tagaatgtta aaccacccat | 480 |
| ctcatcatat atctaggact ttagcacaag gattgttgcc ataagaatga agctttaga | 540 |
| gtgatttctt agggaatgga cacaccaatt aactgtctcc tggcccacc tttgatgttt | 600 |
| tcttcacag | 609 |

<210> SEQ ID NO 51
<211> LENGTH: 49
<212> TYPE: DNA
<213> ORGANISM: Homo sapiens

<400> SEQUENCE: 51

| | |
|---|---|
| caatgcactg acggatatga gtgggatcct gtgagacagc aatgcaaag | 49 |

<210> SEQ ID NO 52
<211> LENGTH: 167
<212> TYPE: DNA
<213> ORGANISM: Homo sapiens

<400> SEQUENCE: 52

| | |
|---|---|
| gtgagccagc ttcaaagact tccatgtgat cattgccttc tgtctccatc tcttgtgtca | 60 |
| ctcttcctgt cctgtctgtg ttataccaaa aaggcatgag cattatattt acatgtttga | 120 |
| tttttccctc ttagaaratt cctgacttat tttattactg accacag | 167 |

<210> SEQ ID NO 53
<211> LENGTH: 387
<212> TYPE: DNA
<213> ORGANISM: Homo sapiens

<400> SEQUENCE: 53

| | |
|---|---|
| atattgatga atgtgacatt gtcccagacg cttgtaaagg tggaatgaag tgtgtcaacc | 60 |
| actatggagg atacctctgc ttccgaaaa cagcccagat tattgtcaat aatgaacagc | 120 |
| ctcagcagga aacacaacca gcagaaggaa cctcagggc aaccaccggg gttgtagctg | 180 |
| ccagcagcat ggcaaccagt ggagtgttgc ccggggtgg ttttgtggcc agtgctgctg | 240 |
| cagtcgcagg ccctgaaatg cagactggcc gaaataactt tgtcatccgg cggaacccag | 300 |
| ctgaccctca gcgcattccc tccaacccctt cccaccgtat ccagtgtgca gcaggctacg | 360 |
| agcaaagtga acacaacgtg tgccaag | 387 |

<210> SEQ ID NO 54
<211> LENGTH: 77
<212> TYPE: DNA
<213> ORGANISM: Homo sapiens

<400> SEQUENCE: 54

| | |
|---|---|
| gtaggaataa cttattttcc taacccattg aaagctgcag gagaaccccc atgaagcttg | 60 |
| aattcggatc cacgttg | 77 |

<210> SEQ ID NO 55
<211> LENGTH: 626
<212> TYPE: DNA
<213> ORGANISM: Homo sapiens

```
<400> SEQUENCE: 55
tttggcattc tgaaattttg caatgaaaga tttatacawa catgttgccc tgctgtttgg      60
caaaaaacaa acagctacmg ggraacggta taatattaaa ggttgatwac acccagttat    120
tggttagatt tttagaaatt tgtcaatgga aattatctca aatacaatat attggatgga    180
aaagcaagta tcatacaatc tattaaaatt tttaacatac aaaacaatac catatgttct    240
aatggatgca tccctgtcta acaaaagtac aaaaacatct cagggaagga ttcattccta    300
ccgagacagt ggtagctgat gggtcaaggg atgaggatgg tgtgaggctt tagctgtatc    360
tgaaatgttt cttaacaaaa caaatgagc caagaccaac atgacaaaat gttagcattt     420
gttaaatctg agcagtactc actggtattt gcaaaattat tttctgaaca cttgaaataa    480
tttataattt taaacatttc caatgcaaga acattataaa ctttttaagaa taaagtwaaa   540 atttagctta agaagtggcm aaatggarga aatatcaaca tcttcacaac tgacaatyyt    600
tytstgtgct wgyatgtcts wgacag                                         626

<210> SEQ ID NO 56
<211> LENGTH: 123
<212> TYPE: DNA
<213> ORGANISM: Homo sapiens

<400> SEQUENCE: 56
acatagacga gtgcactgca gggacgcaca actgtagagc agaccaagtg tgcatcaatt     60
tacggggatc ctttgcatgt cagtgccctc ctggatatca gaagcgaggg gagcagtgcg    120
tag                                                                  123

<210> SEQ ID NO 57
<211> LENGTH: 206
<212> TYPE: DNA
<213> ORGANISM: Homo sapiens

<400> SEQUENCE: 57
gtaagtacca cagtgcagtg agcacggtcc tgtcttgagt accttaactg tttcaacctc     60
aagcattcca atcaaagcat tcatgttcct ttggagagtg gtagccaata attccttatt    120
tttttataga ctaccaatcc attttccaca ataacaagaa acaaccttaa aggttgaggc    180
aggagaaccc catgaagctt gaattc                                         206

<210> SEQ ID NO 58
<211> LENGTH: 294
<212> TYPE: DNA
<213> ORGANISM: Homo sapiens

<400> SEQUENCE: 58
aaactgacat cttatatata tatgcaatag tctcaattat tttgtttttct ttaaatctca    60 atccacccac caagtttatt taccactgaa tggcatgaac attgagtctt tgttcttaac    120
ttcttaactc agaatacaaa gtatatttaa aatacatata ccctaatttt aacaaaatag    180
gaaattatta cttttaaaaa gagatttttct ctacataggt tttctagata atgcttttca    240
gagaatgcta attcaataat ttggttctct ttgtgtgtgt gcctgataac ctag           294

<210> SEQ ID NO 59
<211> LENGTH: 120
<212> TYPE: DNA
```

-continued

```
<400> SEQUENCE: 59
acatagatga atgtaccatc cctccatatt gccaccaaag atgcgtgaat acaccaggct      60
cattttattg ccagtgcagt cctgggtttc aattggcagc aaacaactat acctgcgtag    120

<210> SEQ ID NO 60
<211> LENGTH: 171
<212> TYPE: DNA
<213> ORGANISM: Homo sapiens

<400> SEQUENCE: 60
gtaagccttt tgagaacttg ctgatttctg tcttcacaaa aggaaacccc atgccatgtt     60
gcagtatttc cagttttcta tgttcttgag taaatagttt ccatcgactt cccttcagca   120
atcataaagy tgcaggagaa ccccatgaag cttgaattcg gatccacgtg g            171

<210> SEQ ID NO 61
<211> LENGTH: 701
<212> TYPE: DNA
<213> ORGANISM: Homo sapiens
<220> FEATURE:
<223> OTHER INFORMATION: "n" bases at various positions throughout the
      sequence may be a, t, c, g, other or unknown

<400> SEQUENCE: 61
aaactttccc actgaaagtg cattcttgat ttttacatgc cttttttytcc cctttcagaa     60 atgcaatgtc acggcacaac aattaaaaga ttggcatgac atgggaaaaa atctagtgtr    120
ggaaaaatgc ctttttcaaca atattttcag tgctttagaa gcattgcaaa actccgtatg   180
ggttctcaaa ggcttatgtt ataattgtaa tggaatttaa cagaacccat ttaaaaaagt    240
taataaatag ccacagataa atcttccagt accagcattg cctgaagaag accatatcca    300
gtataagttg tcttatawca attatttata gaaattggca ttttgtwtct tgaaccaaca    360
aaagaaaaat ccgaatmccg gaaktgttat atttwttaga agcattaaat tcctttggan    420
agattnatca cacatcnnac taactgtcat tcctagaaaa aatatttcgg tatttccnaa    480
agaagtatat gacagacgtt tgtagttgtt cccacaaata tganaccnaa atggatgttc    540
tccagtgagc ttctgcaggg caaataattc agctagggaa ttactcactt gtcagcagat    600
gacgtaggta caaaagagta aggatatgtt taaagtstay mtatatmtgt gtgtgtatay    660
atatacatat acaymwmymt atayatamra ttttttttcwa g                       701

<210> SEQ ID NO 62
<211> LENGTH: 120
<212> TYPE: DNA
<213> ORGANISM: Homo sapiens

<400> SEQUENCE: 62
atataaatga atgtgatgcc agcaatcaat gtgctcagca gtgctacaac attcttggtt     60
cattcatctg tcagtgcaat caaggatatg agctaagcag tgacaggctc aactgtgaag   120

<210> SEQ ID NO 63
<211> LENGTH: 1243
<212> TYPE: DNA
<213> ORGANISM: Homo sapiens

<400> SEQUENCE: 63
gtaaaactct tcccagatag tatggaataa agtccaattc ctgtgactgc tgttgtttta     60
tctgattatg tacccatttta tgaaaacaaa cgcttaccca tgggaattct gttctaaaat   120
```

-continued

| | |
|---|---|
| ccagttaatg tagttcagtt gttacattgc cttttagtg tgttaccaag aaaaaggaaa | 180 |
| agaaataaaa ataactgaaa tattaggtgc aggctggctc taataattag aaagggtgct | 240 |
| ctagcatgtt gcgtctcagt gtgttatcca gtgaccaggt atgtcagcac ctcctgggag | 300 |
| cttatgagaa atgcagaatc tcaggctgca acccagacct cctgagtctg aatctacatt | 360 |
| caacaaaaac tgcaggtgac tggtgtgcac atttaagttt cagaatagcc aagtgcatgt | 420 |
| caaaacatta aataaaaat caggagatct ggtttctggt tctattcctg ctactgtgtg | 480 |
| acttgggcac atttcttgag ttgcctgggt ttcactttcc acatgaacaa gaggagggcc | 540 |
| atttaactag attcatgacc ttcagggtcc attgcatgtg cacatttcgt tatataattc | 600 |
| aaaaggcatt agacatcctg aggggatgc cacagacact tgatgtccct gacctcctca | 660 |
| cggttcactc agctttacac aaagctcaaa ccccaccgag agaggcctca catcatgcca | 720 |
| ttacactcaa aactgaaaga ggctacctca ggacagctgc ctctgcccct ctgagtaaac | 780 |
| tgtagggaca tcactattca gaaatgcaaa gcattcttcc cctgaaagtc agatcctgcc | 840 |
| aagctgtcat tctggaagct tgcacaggtt aggggacttg gcattcaaag ctcaaatgaa | 900 |
| cttggcttca aagtcaccca atttctgaga agacaaacat gaactctaca tcctggatgg | 960 |
| gtctgcagag tccaaaatga aggccgtcaa ccacaagcca attcattcag tagtgtagtt | 1020 |
| aggtccagga ttagccaaat tgtcagcaat gattcagtaa aagtcatgat aagaaaaact | 1080 |
| ttttgtgcta tgaagtcata gagggaaata agctgatatt gttagaattt gccttttagc | 1140 |
| tgcttataaa gttttgtatt tctatttcag aatttgcaat attttactc tctttagctc | 1200 |
| acctcaaaag tgtattactt cctctggact gttgagcaga aca | 1243 |

<210> SEQ ID NO 64
<211> LENGTH: 312
<212> TYPE: DNA
<213> ORGANISM: Homo sapiens
<220> FEATURE:
<223> OTHER INFORMATION: "n" bases at various positions throughout the
     sequence may be a, t, c, g, other or unknown

<400> SEQUENCE: 64

| | |
|---|---|
| aaaaaaatat atatgtgtgt gtgtgtgtgt gtgtgtgtgt gtgtatatta aacccagnca | 60 |
| acttaaaaaa tgtgcccaag tcacacagtc gcaggaatag gacaanaagc cagatctctt | 120 |
| tatatatata taggtagata taattttcc tccttanaat ataaataatt ttaattatat | 180 |
| ataattattt taatatagat attttaaatc ttataattta tatatatata taatttatat | 240 |
| atatatatat atccaaagta gtggtgcaca aacttttcaa ctctgtgtcc tttctcttgt | 300 |
| ctaattcaac ag | 312 |

<210> SEQ ID NO 65
<211> LENGTH: 120
<212> TYPE: DNA
<213> ORGANISM: Homo sapiens

<400> SEQUENCE: 65

| | |
|---|---|
| acattgatga atgcagaacc tcaagctacc tgtgtcaata tcaatgtgtc aatgaacctg | 60 |
| ggaaattctc atgtatgtgc ccccagggat accaagtggt gagaagtaga acatgtcaag | 120 |

<210> SEQ ID NO 66
<211> LENGTH: 973
<212> TYPE: DNA

<213> ORGANISM: Homo sapiens
<220> FEATURE:
<223> OTHER INFORMATION: "n" bases at various positions throughout the
      sequence may be a, t, c, g, other or unknown

<400> SEQUENCE: 66

| | | | | | |
|---|---|---|---|---|---|
| gtaagtttat | ttttttttc | atatgttagg | tatttagttt | tagccaggaa | gagacaagag | 60 |
| gaagttatag | gattctccta | tagactttca | ttttcccac | tttcaatata | caatttaagc | 120 |
| tnttttttcc | cctgttcatc | ataaaatata | tacatctcat | aaagagggga | ttctatgcta | 180 |
| angccgacnt | ttttcgtcct | taaaagataa | ataatttaa | taaatattg | atatgtattc | 240 |
| tatgtaacct | acatcatctn | tttgagatac | atcttcaaat | catccactgg | aaaagattca | 300 |
| gttattaaaa | ngtttcacct | gtgagtttga | gtttanagca | taagctcaat | atgggagtta | 360 |
| aacatacctc | catccagtct | tagccctcta | aaacncangg | attataaatt | gcgtaaaaat | 420 |
| gtaggtgctg | aaaaaagtca | gcctaatatg | ttgtaaaata | tagttgaata | ttttagagaa | 480 |
| aactactagc | cccaaaatag | ctaatgacct | tgggtccagt | ttcaaaataa | acattcagat | 540 |
| gatcttcaca | cctatacgta | agkggaagag | gcagctcccc | acaatggtat | gatttcagag | 600 |
| tttctcagga | agatctaaaa | aaaaaagga | ccctacctcc | aatgttgcat | gtagttgaaa | 660 |
| attttcttaa | cagggaaagg | actgtcanat | aaaaccaaaa | acgtaaaaaa | tcctggaaaa | 720 |
| gctagtncaa | acncttaaat | ttacncaaag | caccaaaaga | atgaaaaaat | gaccaanctt | 780 |
| gacanaaaac | ctgtttgaat | cccagctcca | ctgtnttcag | tctgcncaat | nttgaacaaa | 840 |
| ttatcaaact | actntgagcc | tcagnttcct | catttggaaa | agggagttgg | gggaatttag | 900 |
| gggaatanca | tncntaaaaa | tantttgtaa | actataaagc | ttgtncaggt | caagggttt | 960 |
| ttatnaaatt | tac | | | | | 973 |

<210> SEQ ID NO 67
<211> LENGTH: 766
<212> TYPE: DNA
<213> ORGANISM: Homo sapiens

<400> SEQUENCE: 67

| | | | | | |
|---|---|---|---|---|---|
| agcctcttcc | ttaacttcct | cttttccctt | acagtcctaa | aattgctatg | ctctatgagg | 60 |
| tggaacactt | catagtttca | cttcctgtgc | tgtgcttcct | ctggacagta | taatccactc | 120 |
| ccagcatgct | tcagcttact | gaaaccagat | ttctagcctt | tacctttctc | ccaagttcct | 180 |
| gaaagagatg | ataagctgcc | ctccatagtt | tatgcttcct | gatttctcag | cttggaaagc | 240 |
| cttccctgcc | ccagccatga | aaactccatc | taaccaccac | ccttcaaggc | cacgttgaga | 300 |
| tgcctcttcc | ttccttcagc | cttccctaat | ccccctggca | aaattaccca | actctgctcc | 360 |
| acatgcccca | gtatacttat | ctatctctta | cttaattcca | ttttactttc | taagtaatca | 420 |
| tatacacatt | ccctcaatta | taatgtccct | gatgacaaga | actggtgttt | aactttata | 480 |
| taggcagagt | cagtggttaa | cattggggtt | tgaattcaac | agatgaacaa | taggtgcttg | 540 |
| ataaaatatc | atgaaatgac | acatattaat | ctgcctagaa | tgtctcagct | ctgtctgtcc | 600 |
| tgaattcaat | acaatgaaca | cccagtcttg | tgtctaaaag | caggttgaac | acagtccaga | 660 |
| tgctctcaca | cctccttcct | tgcaaacaga | atctgccagt | tatatgattt | aattagatca | 720 |
| gttcattagt | ttagttagta | aactctttga | ccctacatct | ctacag | | 766 |

<210> SEQ ID NO 68
<211> LENGTH: 124

```
<212> TYPE: DNA
<213> ORGANISM: Homo sapiens

<400> SEQUENCE: 68
atataaatga gtgtgagacc acaaatgaat gccgggagga tgaaatgtgt tggaattatc      60
atggcggctt ccgttgttat ccacgaaatc cttgtcaaga tccctacatt ctaacaccag     120
agaa                                                                 124

<210> SEQ ID NO 69
<211> LENGTH: 84
<212> TYPE: DNA
<213> ORGANISM: Homo sapiens

<400> SEQUENCE: 69
gtaagaaaaa tcagaacttt tgaaagtgag gattttctgg tcttaccaag ccaaactgct      60
gaatactttt gtttgtctct gcag                                            84

<210> SEQ ID NO 70
<211> LENGTH: 196
<212> TYPE: DNA
<213> ORGANISM: Homo sapiens

<400> SEQUENCE: 70
ccgatgtgtt tgcccagtct caaatgccat gtgccgagaa ctgccccagt caatagtcta      60
caaatacatg agcatccgat ctgataggtc tgtgccatca gacatcttcc agatacaggc     120
cacaactatt tatgccaaca ccatcaatac ttttcggatt aaatctggaa atgaaaatgg     180
agagttctac ctacga                                                    196

<210> SEQ ID NO 71
<211> LENGTH: 979
<212> TYPE: DNA
<213> ORGANISM: Homo sapiens
<220> FEATURE:
<223> OTHER INFORMATION: "n" bases at various positions throughout
      the sequence may be a, t, c, g, other or unknown

<400> SEQUENCE: 71
gtaagtatcc tgaaggcagc cttaactatt gagaaagatg ggagtttgtt gttgttgttg      60
ttgttgttgt tgttgtgtgg tatccacatg tggaaggaaa gcaaacattt aaaagtgtct     120
tnatgtgtag gcattgtgta aggccttcca gctacattat ttcatttatt cctcttggta     180
acactgccag atagatatta atattcatct ccattttta cagaggagaa aagtgagatg      240
cagaaagatt aagtagcatc cctgaaatca ctcaaatatt aagtttggca gactctgata     300
gagttgtgtg tgaccacgaa aatacaagcc tcccatcccc ccgcctctgc ccccacccaa     360
catacccccc aagtaggtat cactaatcat tgatggttaa ttaattatac atagacatac     420
atataattca aacccaaaat aattcctgga gctcctaaag agttttttcag acatcatgaa     480 ttcatcattg ttacattcac aagacagttt gtgttcacac cgaaactaaa acctataagt     540
atgtgagaag tgaccccacc tccccgcaca gtatgtgtca agtagttgta ccttcttgcc     600
aacttctggg ctggcagtat ggagtcatct ccctatcttt cattgcctgt gtgaaatcta     660
ctttctgaat tctgccattt ccctcttcac actgtctcct gggttatctt tgcttcctca     720
catccctatc tctcttccta taaactggct cccgtcactt ccatgatccc ttcagtggct     780
tctgagctgg tctccctgac cccaaagcct cagccttcca gtctccctac aaaatctcag     840
caagttcatt ttaaggttaa aatttggaca tattttaaat acggctcacc acttcatgtg     900
```

```
aaaatgatgg caccctacca agcagtttgc agagttaccg gtaactgttt catgctaatg    960
atgttaytca tccagttac                                                 979
```

<210> SEQ ID NO 72
<211> LENGTH: 418
<212> TYPE: DNA
<213> ORGANISM: Homo sapiens
<220> FEATURE:
<223> OTHER INFORMATION: "n" bases at various positions throughout the
      sequence may be a, t, c, g, other or unknown

<400> SEQUENCE: 72

```
tccctttttt ttttcyttct aaaaaggnaa ccnatggccc aagnttgnaa aaanaaaaag     60
ggccnctttg ntttccaggt ttaaaaattt ccnattttcc cctwaagttt agkttttgga    120
aaggccccca cttcnccann aaaaggaaaa aaaatgntta cmaanagggg gggattcaaa    180
acnaaaaact ttttttaaaaa aaaaaaaaag caagtccttg aaacttggag ctaatgactg    240
tattagacaa gggataagag ccaagaagag ttgaaaccaa gaagggacca agtagtggct    300
cttttatacc accttcaaaa ttctccccct aattcttata ggaggtatac taacaaagca    360
tagaaactcc aatccaagaa aattattctc ttcctttctc tattttcttt tattttag     418
```

<210> SEQ ID NO 73
<211> LENGTH: 162
<212> TYPE: DNA
<213> ORGANISM: Homo sapiens

<400> SEQUENCE: 73

```
caaacaagtc ctgtaagtgc aatgcttgtg ctcgtgaagt cattatcagg accaagagaa     60
catatcgtgg acctggagat gctgacagtc agcagtatag ggaccttccg cacaagctct    120
gtgttaagat tgacaataat agtggggcca ttttcatttt ag                       162
```

<210> SEQ ID NO 74
<211> LENGTH: 1111
<212> TYPE: DNA
<213> ORGANISM: Homo sapiens

<400> SEQUENCE: 74

```
tcttttctaa gagtcaacca caggcattta agtcagccaa agaatattgt taccttaaag     60
cactatttta tttatagata tatctagtgc atctacatct ctatactgta cactcaccca    120
taacaaacaa ttcaccatg gtataaagtg gcatttaat atgtaaagat tcaaagttg      180 tctttattac tatatgtaaa ttagacatta atccactaaa ctggtcttct tcaagagagc    240
taagtataca ctatctggtg aaacttggat tctttcctat aaaagtggga ccaagcaatg    300
atgatcttct gtggtgctta aggaaactta ctagagctcc actaacagtc tcataaggag    360
gcagccatca taaccattga atagcatgca agggtaagaa tgagttttta actgctttgt    420
aagaaaatgg aaaaggtcaa taaagatata tttctttaga aaatggggat ctgccatatt    480
tgtgttggtt tttattttca tatccagcct aaaggtggtt gtttattata tagtaataaa    540
tcattgctgt acaacatgct ggtttctgta gggtatttt aattttgtca gaaattttag    600
attgtgaata ttttgtaaaa aacagtaagc aaaattttcc agaattccca aaatgaacca    660
gataccccct agaaaattat actattgaga aatctatggg gaggatatga gaaataaat     720 tccttctaaa ccacattgga actgacctga gaaagcaaac tcggaaaata taataacatc    780
cctgaattca ggcattcaca agatgcagaa caaaatggat aaaaggtatt tcactggaga    840
```

```
agttttaatt tctaagtaaa atttaaatcc taacacttca ctaatttata actaaaattt      900
ctcatcttcg tacttgatgc tcacagagga agaaaatgat gatggttttt attcctggca      960
tccagagtga cagtgaactt aagcaaatta ccctcctacc caattctatg gaatatttta     1020
tacgtctcct tgtttaaaat ctgactgctt tactttgatg tatcatattt ttaaataaaa     1080
ataaatattc ctttagaaga tcactctaaa a                                    1111
```

MACULAR DEGENERATION DIAGNOSTICS AND THERAPEUTICS

This Application is a continuation-in-part of U.S. Ser. No. 09/248,757, filed Feb. 12, 1999 now U.S. Pat. No. 6,417,342, the contents of which are incorporated herein by reference.

1. BACKGROUND OF THE INVENTION

Macular degeneration is a clinical term that is used to describe a variety of diseases that are all characterized by a progressive loss of central vision associated with abnormalities of Bruch's membrane and the retinal pigment epithelium. These disorders include very common conditions that affect older patients (age related macular degeneration or AMD) as well as rarer, earlier-onset dystrophies that in some cases can be detected in the first decade of life[1-18]. The genes associated with some of these dystrophies have been mapped,[5-14] and in four cases, blue-cone monochromasy,[15] pattern dystrophy,[16,17] and Sorsby fundus dystrophy,[18] and Best Disease actually identified. However, none of the latter genes has been found to be responsible for a significant fraction of typical late-onset macular degeneration.

In developed countries, AMD is the most common cause of legal blindness in older patients.[19] The hallmark of this condition is the presence of drusen, which are ophthalmoscopically visible, yellow-white hyaline excrescences of Bruch's membrane. In some families, drusen are heritable in an autosomal dominant fashion.

In 1875, Hutchinson and Tay published a paper entitled "Symmetrical Central Choroido-Retinal Disease Occurring in Senile Persons".[20] This paper includes one of the first descriptions of the constellation of clinical findings now known as age related macular degeneration (AMD). Specifically, three of the ten patients in the report were sisters affected with whitish spots (now referred to as drusen) in the macula. In 1899, Doyne[21] reported a similar disorder in which the abnormal spots were nearly confluent such that the macula had a "honeycomb" appearance. Histopathologic examination of one of Doyne's patients[22] revealed the abnormalities to be hyaline thickenings of Bruch's membrane. In 1925, Vogt[23] published the first description of the ophthalmoscopic appearance of a form of familial drusen that had been observed in patients living in the Leventine valley in the Ticino canton of southern Switzerland. Klainguti[24] fully characterized this condition in 1932 and demonstrated its autosomal dominant inheritance. This disorder eventually became known as malattia leventinese, "ML" (i.e., Leventine disease). In 1948, Waardenburg[25] stated that there was little reason to make a distinction between malattia leventinese and the condition described by Doyne, referred to as Doyne's Honeycomb Retinal Dystrophy (DHRD). This position was strengthened when Forni and Babel[26] found that the histopathologic features of malattia leventinese were indistinguishable from those of Doyne's honeycomb choroiditis. Piguet, Haimovici and Bird[27] recently reviewed the history of these conditions and also pointed out that the drusen in families with malattia leventinese are frequently distributed in a radical pattern. Choroidal neovascularization is uncommon in patients with radial drusen but does occur.[27] Although originally recognized in Switzerland, families affected with autosomal dominant radial drusen have been identified in Czechoslovakia,[28,29] and the United States.[30]

In 1996, ML was mapped to chromosome 2p16–21[48]. Shortly thereafter, DHRD was mapped to the same locus[49] and the genetic interval was narrowed[48,49]. ML and DHRD are very similar phenotypically to AMD.

Currently, there is no therapy that is capable of significantly slowing the degenerative progression of macular degeneration, and treatment is limited to laser photocoagulation of the subretinal neovascular membranes that occur in 10–15% of affected patients.

2. SUMMARY OF THE INVENTION

The present invention is based, at least in part, on the discovery of a novel human gene encoding a novel human protein, which has sequence homologies with fibulin (1 and 2), fibrillin, nidogen, notch, protein S and Factor IX. The newly identified proteins and nucleic acids described herein are referred to as "EFEMPs". The human EFEMP1 gene (herein referred to as hEFEMP1) transcript is shown in FIG. 5 and includes 5' and 3' untranslated regions and a 1479 base pair open reading frame encoding a 493 amino acid polypeptide having SEQ ID NO. 1. Mouse EFEMP1 is expressed in eye, brain, heart, lung and kidney tissue.

In one aspect, the invention features isolated EFEMP1 nucleic acid molecules. In one embodiment, the EFEMP1 nucleic acid is from a vertebrate. In a preferred embodiment, the EFEMP1 nucleic acid is from a mammal, e.g. a human. In an even more preferred embodiment, the nucleic acid has the nucleic acid sequence set forth in FIG. 5 or a portion thereof. The disclosed molecules can be non-coding, (e.g. a probe, antisense, or ribozyme molecule) or can encode a functional EFEMP1 polypeptide (e.g. a polypeptide which specifically modulates biological activity, by acting as either an agonist or antagonist of at least one bioactivity of the human EFEMP1 polypeptide). In another embodiment, the nucleic acid of the present invention can hybridize to a vertebrate EFEMP1 gene or to the complement of a vertebrate EFEMP1 gene. In a further embodiment, the claimed nucleic acid can hybridize with a nucleic acid sequence shown in FIG. 5 or a complement thereof. In a preferred embodiment, the hybridization is conducted under mildly stringent or stringent conditions.

In further embodiments, the nucleic acid molecule is an EFEMP1 nucleic acid that is at least about 70%, preferably about 80%, more preferably about 85%, and even more preferably at least about 90% or 95% homologous to the nucleic acid shown as SEQ ID NO: 1 or to the complement of the nucleic acid shown as FIG. 5.

The invention also provides probes and primers comprising substantially purified oligonucleotides, which correspond to a region of nucleotide sequence which hybridizes to at least about 6, at least about 10, at least about 15, at least about 20, or preferably at least about 25 consecutive nucleotides of the sequence set forth as FIG. 5 or complements of the sequence set forth as FIG. 5 or naturally occurring mutants or allelic variants thereof. In preferred embodiments, the probe/primer further includes a label group attached thereto, which is capable of being detected.

For expression, the subject nucleic acids can be operably linked to a transcriptional regulatory sequence, e.g., at least one of a transcriptional promoter (e.g., for constitutive expression or inducible expression) or transcriptional enhancer sequence. Such regulatory sequences in conjunction with an EFEMP1 nucleic acid molecule can provide a useful vector for gene expression. This invention also describes host cells transfected with said expression vector whether prokaryotic or eukaryotic and in vitro (e.g. cell culture) and in vivo (e.g. transgenic) methods for producing EFEMP 1 proteins by employing said expression vectors.

In another aspect, the invention features isolated EFEMP1 polypeptides, preferably substantially pure preparations, e.g. of plasma purified or recombinantly produced polypeptides. The EFEMP1 polypeptide can comprise a full length protein or can comprise smaller fragments corresponding to one or more particular motifs/domains, or fragments comprising at least about 6, 10, 25, 50, 75, 100, 125, 150, 200, 225, 250, 300, 310, 320, 330, 340, 350, 360, 370, 380, 390, 400, 410, 420, 430, 440, 450, 460, 470 480 or 490 amino acids in length. In particularly preferred embodiments, the subject polypeptide has an EFEMP1 bioactivity.

In a preferred embodiment, the polypeptide is encoded by a nucleic acid which hybridizes with the nucleic acid sequence represented in FIG. 5. In a further preferred embodiment, the EFEMP1 polypeptide is comprised of the amino acid sequence set forth in SEQ ID NO. 1. The subject EFEMP1 protein also includes within its scope modified proteins, e.g. proteins which are resistant to post-translational modification, for example, due to mutations which alter modification sites (such as tyrosine, threonine, serine or aspargine residues), or which prevent glycosylation of the protein, or which prevent interaction of the protein with intracellular proteins involved in signal transduction.

The EFEMP1 polypeptides of the present invention can be glycosylated, or conversely, by choice of the expression system or by modification of the protein sequence to preclude glycosylation, reduced carbohydrate analogs can also be provided. Glycosylated forms can be obtained based on derivatization with glycosaminoglycan chains. Also, EFEMP1 polypeptides can be generated which lack an endogenous signal sequence (though this is typically cleaved off even if present in the pro-form of the protein).

In yet another preferred embodiment, the invention features a purified or recombinant polypeptide, which has the ability to modulate, e.g., mimic or antagonize, an activity of a wild-type EFEMP1 protein. Preferably, the polypeptide comprises an amino acid sequence identical or homologous to a sequence designated in SEQ ID NO. 1.

Another aspect of the invention features chimeric molecules (e.g., fusion proteins) comprising an EFEMP1 protein. For instance, the EFEMP1 protein can be provided as a recombinant fusion protein which includes a second polypeptide portion, e.g., a second polypeptide having an amino acid sequence unrelated (heterologous) to the EFEMP 1 polypeptide. A preferred EFEMP1 fusion protein is an immunoglobulin-EFEMP1 fusion protein, in which an immunoglobulin constant region is fused to an EFEMP1 polypeptide.

Yet another aspect of the present invention concerns an immunogen comprising an EFEMP1 polypeptide in an immunogenic preparation, the immunogen being capable of eliciting an immune response specific for an EFEMP1 polypeptide; e.g. a humoral response, an antibody response and/or cellular response. In a preferred embodiment, the immunogen comprises an antigenic determinant, e.g. a unique determinant of a protein encoded by the nucleic acid set forth in SEQ ID NO. 1 or as set forth in SEQ ID NO. 1.

A still further aspect of the present invention features antibodies and antibody preparations specifically reactive with an epitope of an EFEMP1 protein.

The invention also features transgenic non-human animals which include (and preferably express) a heterologous form of an EFEMP1 gene described herein, or which mis-express an endogenous EFEMP1 gene (e.g., an animal in which expression of one or more of the subject MFGF proteins is disrupted). Such transgenic animals can serve as animal models for studying cellular and/or tissue disorders comprising mutated or mis-expressed EFEMP1 alleles or for use in drug screening. Alternatively, such transgenic animals can be useful for expressing recombinant EFEMP1 polypeptides.

The invention further features assays and kits for determining whether an individual's EFEMP1 genes and/or proteins are defective or deficient (e.g in activity and/or level), and/or for determining the identity of EFEMP1 alleles. In one embodiment, the method comprises the step of determining the level of EFEMP1 protein, the level of EFEMP1 mRNA and/or the transcription rate of an EFEMP1 gene. In another preferred embodiment, the method comprises detecting, in a tissue of the subject, the presence or absence of a genetic alteration, which is characterized by at least one of the following: a deletion of one or more nucleotides from a gene; an addition of one or more nucleotides to the gene; a substitution of one or more nucleotides of the gene; a gross chromosomal rearrangement of the gene; an alteration in the level of a messenger RNA transcript of the gene; the presence of a non-wild type splicing pattern of a messenger RNA transcript of the gene; and/or a non-wild type level of the EFEMP1 protein. For example, detecting a genetic alteration or the presence of a specific polymorphic region can include (i) providing a probe/primer comprised of an oligonucleotide which hybridizes to a sense or antisense sequence of an EFEMP1 gene or naturally occurring mutants thereof, or 5' or 3' flanking sequences naturally associated with the EFEMP1 gene; (ii) contacting the probe/primer with an appropriate nucleic acid containing sample; and (iii) detecting, by hybridization of the probe/primer to the nucleic acid, the presence or absence of the genetic alteration. Particularly preferred embodiments comprise: 1) sequencing at least a portion of an EFEMP1 gene, 2) performing a single strand conformation polymorphism (SSCP) analysis to detect differences in electrophoretic mobility between mutant and wild-type nucleic acids; and 3) detecting or quantitating the level of an EFEMP1 protein in an immunoassay using an antibody which is specifically immunoreactive with a wild-type or mutated EFEMP1 protein.

Information obtained using the diagnostic assays described herein (alone or in conjunction with information on another genetic defect, which contributes to the same disease) is useful for diagnosing or confirming that a symptomatic subject has a genetic defect (e.g. in an EFEMP1 gene or in a gene that regulates the expression of an EFEMP1 gene), which causes or contributes to the particular disease or disorder. Alternatively, the information (alone or in conjunction with information on another genetic defect, which contributes to the same disease) can be used prognostically for predicting whether a non-symptomatic subject is likely to develop a disease or condition, which is caused by or contributed to by an abnormal EFEMP1 activity or protein level in a subject (e.g. a macular degeneration). In particular, the assays permit one to ascertain an individual's predilection to develop a condition associated with a mutation in EFEMP1, where the mutation is a single nucleotide polymorphism (SNP). Based on the prognostic information, a doctor can recommend a regimen (e.g. diet or exercise) or therapeutic protocol useful for preventing or prolonging onset of the particular disease or condition in the individual.

In addition, knowledge of the particular alteration or alterations, resulting in defective or deficient EFEMP1 genes or proteins in an individual, alone or in conjunction with information on other genetic defects contributing to the same disease (the genetic profile of the particular disease)

allows customization of therapy for a particular disease to the individual's genetic profile, the goal of pharmacogenomics. For example, an individual's EFEMP1 genetic profile or the genetic profile of a disease or condition to which EFEMP1 genetic alterations cause or contribute, can enable a doctor to: 1) more effectively prescribe a drug that will address the molecular basis of the disease or condition; and 2) better determine the appropriate dosage of a particular drug. For example, the expression level of EFEMP1 proteins, alone or in conjunction with the expression level of other genes known to contribute to the same disease, can be measured in many patients at various stages of the disease to generate a transcriptional or expression profile of the disease. Expression patterns of individual patients can then be compared to the expression profile of the disease to determine the appropriate drug and dose to administer to the patient.

The ability to target populations expected to show the highest clinical benefit, based on the EFEMP1 or disease genetic profile, can enable: 1) the repositioning of marketed drugs with disappointing market results; 2) the rescue of drug candidates whose clinical development has been discontinued as a result of safety or efficacy limitations, which are patient subgroup-specific; and 3) an accelerated and less costly development for drug candidates and more optimal drug labeling (e.g. since the use of EFEMP1 as a marker is useful for optimizing effective dose).

In another aspect, the invention provides methods for identifying a compound which modulates an EFEMP1 activity, e.g. the interaction between an EFEMP1 polypeptide and a target peptide. In a preferred embodiment, the method includes the steps of (a) forming a reaction mixture including: (i) an EFEMP1 polypeptide, (ii) an EFEMP1 binding partner, and (iii) a test compound; and (b) detecting interaction of the EFEMP1 polypeptide and the EFEMP1 binding protein. A statistically significant change (potentiation or inhibition) in the interaction of the EFEMP1 polypeptide and EFEMP1 binding protein in the presence of the test compound, relative to the interaction in the absence of the test compound, indicates a potential agonist (mimetic or potentiator) or antagonist (inhibitor) of EFEMP 1 bioactivity for the test compound. The reaction mixture can be a cell-free protein preparation, e.g., a reconstituted protein mixture or a cell lysate, or it can be a recombinant cell including a heterologous nucleic acid recombinantly expressing the EFEMP1 binding partner.

In preferred embodiments, the step of detecting interaction of the EFEMP1 and EFEMP1 binding partner is a competitive binding assay. In other preferred embodiments, at least one of the EFEMP1 polypeptide and the EFEMP1 binding partner comprises a detectable label, and interaction of the EFEMP1 and EFEMP1 binding partner is quantified by detecting the label in the complex. The detectable label can be, e.g., a radioisotope, a fluorescent compound, an enzyme, or an enzyme co-factor. In other embodiments, the complex is detected by an immunoassay.

Yet another exemplary embodiment provides an assay for screening test compounds to identify agents which modulate the amount of EFEMP1 produced by a cell. In one embodiment, the screening assay comprises contacting a cell transfected with a reporter gene operably linked to an EFEMP1 promoter with a test compound and determining the level of expression of the reporter gene. The reporter gene can encode, e.g., a gene product that gives rise to a detectable signal such as: color, fluorescence, luminescence, cell viability, relief of a cell nutritional requirement, cell growth, and drug resistance. For example, the reporter gene can encode a gene product selected from the group consisting of chloramphenicol acetyl transferase, luciferase, beta-galactosidase and alkaline phosphatase.

Also within the scope of the invention are methods for treating diseases or disorders which are associated with an aberrant EFEMP1 level or activity or which can benefit from modulation of the activity or level of EFEMP1 (e.g. a macular degeneration). The methods comprise administering, e.g., either locally or systemically to a subject, a pharmaceutically effective amount of a composition comprising an EFEMP1 therapeutic (e.g. an MD therapeutic).

Other features and advantages of the invention will be apparent from the following detailed description and claims.

3. BRIEF DESCRIPTION OF THE DRAWINGS

FIG. 1 is a fundus photograph of a patient affected with malattia leventinese (ML). The confluent yellow drusen in the center of the photograph are characteristic of both ML and Doyne honeycomb retinal dystrophy, while the streak-like radial drusen in the periphery of the photograph are the distinguishing feature of ML.

Figure 2A:
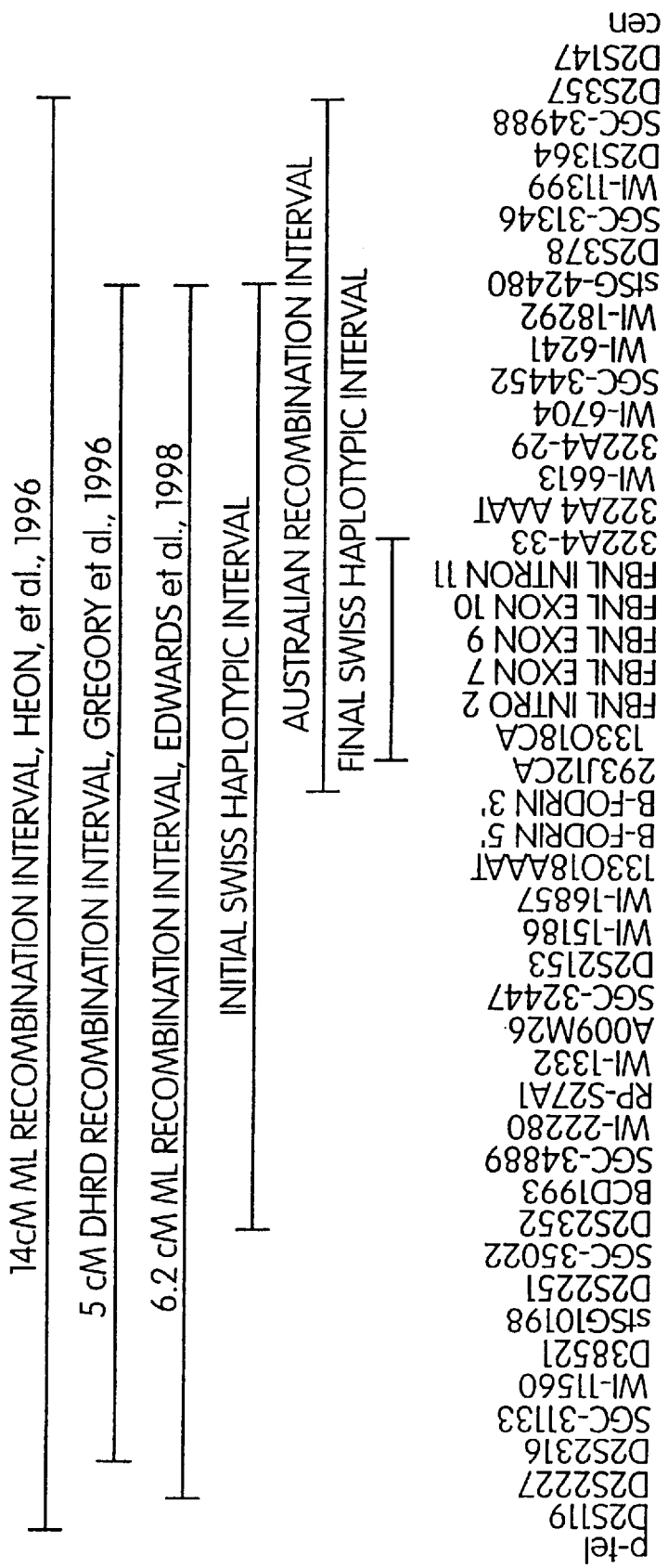
Figure 2B:
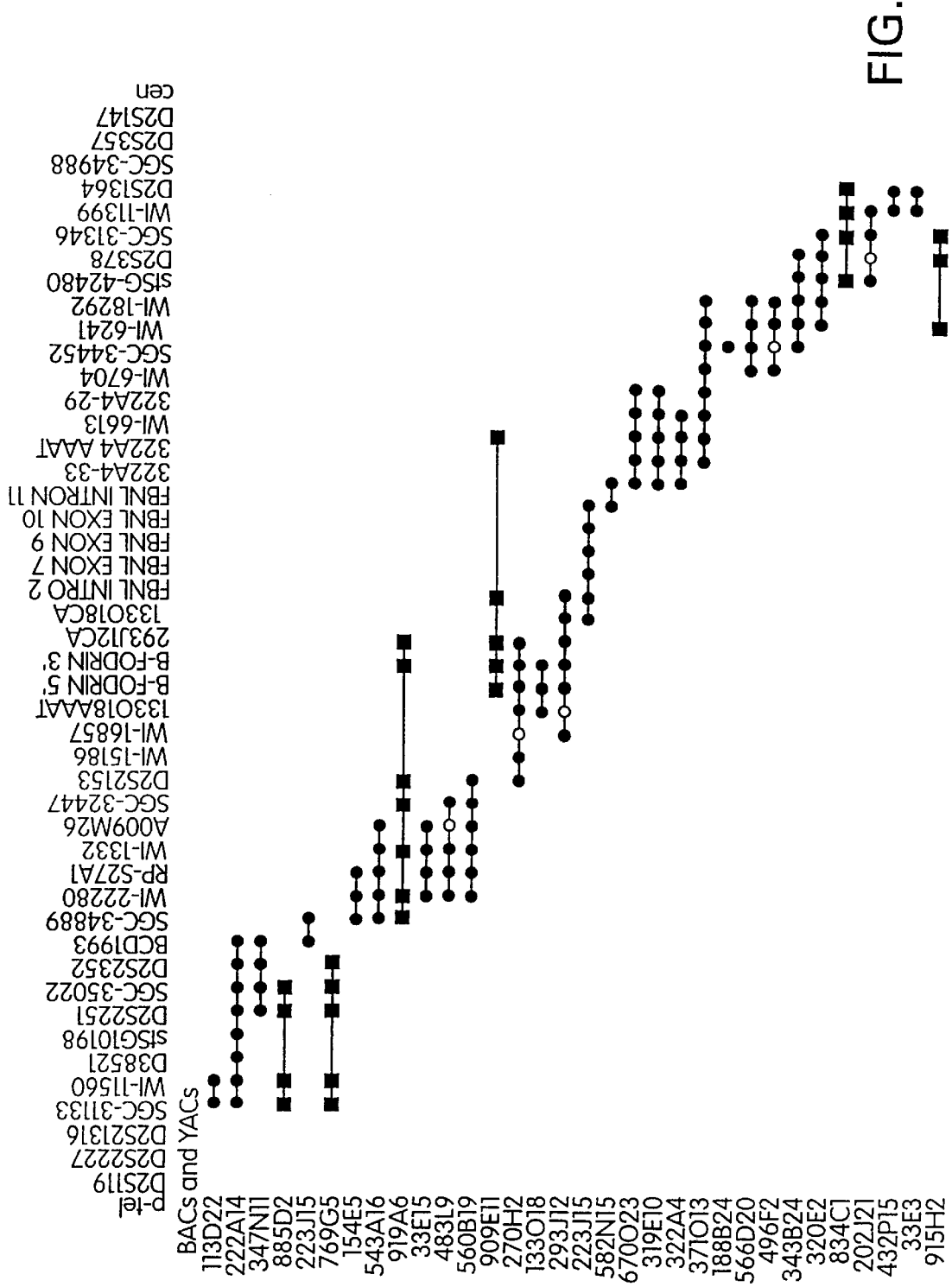

FIGS. 2A and 2B depict bacterial and yeast artificial chromosomes comprising the minimum tiling path of the EFEMP1 locus. The genetic markers and sequence tagged sites found to be present on each artificial chromosome are shown as solid squares (on the YACs) or circles (on the BACs). Open circles or squares indicate PCR failure. Disease intervals based on recombination within families and shared haplotypes between families are indicated with brackets. The names of genes and expressed sequence tagged sites that were screened for coding sequence mutations are shown in bold.

Figure 3:
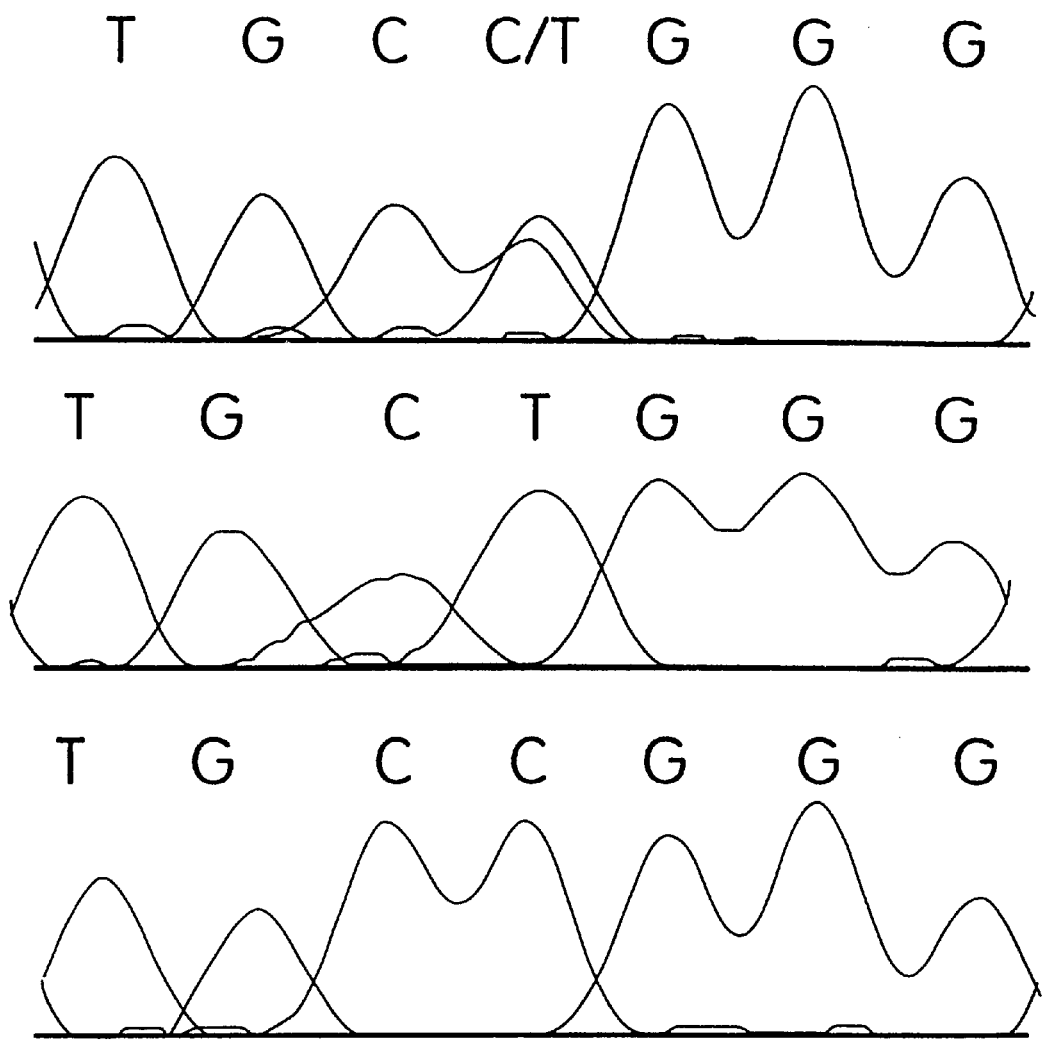

FIG. 3 consists of representative chromatograms generated by fluorescent dye-terminator sequencing of PCR products from two affected individuals, which reveal a C→T transition at the first nucleotide of codon 345, which would be expected to alter the amino acid at this position from an arginine to a tryptophan: a) heterozygous Arg345Trp mutation; b) homozygous Arg345Trp mutation; and c) normal control.

Figure 4A:
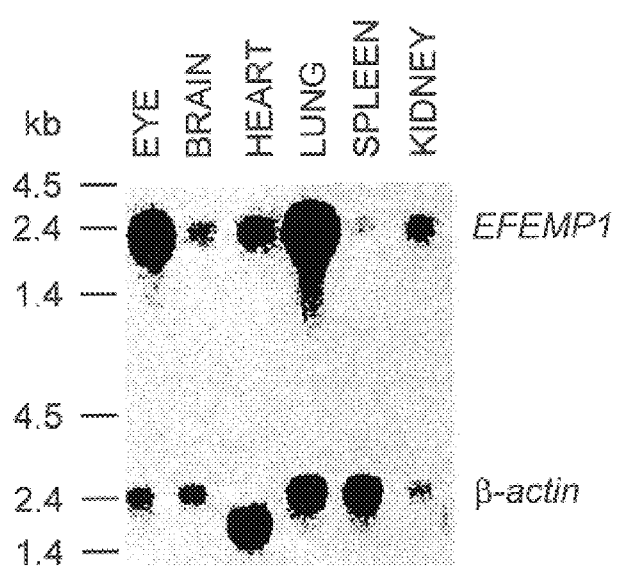

FIG. 4a) is a Northern blot analysis of mouse EFEMP1 and β-actin gene expression. One µg of mouse embryonic and adult tissue poly (A) mRNA were sequentially hybridized with $^{32}$P-labelled cDNA probes for EFEMP1 (upper pane) and β-actin (lower panel).

Figure 4B:
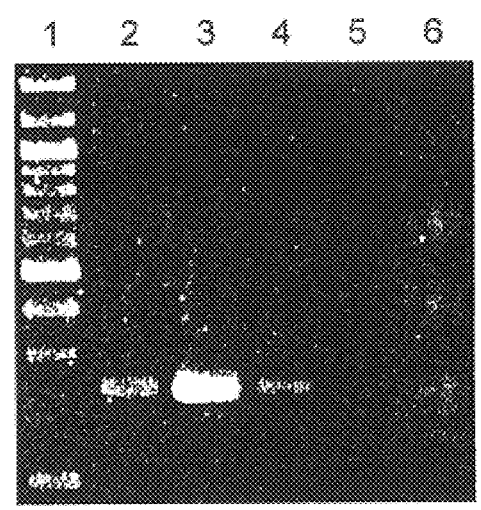

FIG. 4b) shows the results of an RT-PCR analysis of RNA extracted from the human eye. Primers were chosen from the EFEMP1 coding sequences such that the amplimer included portions of exons 11 and 12 and would be of expected size (236 bp) only if it was amplified from the cDNA. The PCR was performed with cDNA prepared from RNA extracted from: lane 2-human neurosensory retina; lane 3- a mixture of human RPE and choroid; and, lane 4- isolated (but non-cultured) human RPE cells from a human donor. For lane 5, the template for amplification was genomic DNA while for lane 6, no template was added. Lane 1 contains the 100 bp ladder.

FIG. 5A, 5B, 5C, 5D, 5E and 5F show human EFEMP1 genomic sequence including 5' and 3' untranslated regions (UTRs), complete with sequences of intron 2, 4 and 10 and partial sequences of introns 3, and 5–9.

FIG. 6 shows human EFEMP1 cDNA sequence and the amino acid sequence of the hEFEMP1 protein.

4. DETAILED DESCRIPTION

4.2 General

The instant invention is based on linkage studies that have mapped a macular degeneration causing gene to a region of human chromosome 2 and on sequencing studies that have identified a mutation in the EFEMP 1 gene within the mapped region, that is associated with ML and DHRD. The coding sequence of the EFEMP1 gene is comprised of 1617 base pairs FIG. 5 and encodes a 539 amino acid extracellular matrix protein (SEQ ID NO 1), which is likely to cause the accumulation of lipofuscin-like material under the retinal pigment epithelium in structures known as drusen (the hallmark of MD). The finding that mutations in EFEMP1 cause macular degeneration allows for diagnostic testing for macular degeneration on presymptomatic individuals, who are at risk of developing macular degeneration based on family history. In addition, tests can be performed on postsymptomatic individuals diagnosed with macular degeneration based on an ophthalmologic examination.

In addition to being used diagnostically, identification of the involvement of mutations in the EFEMP1 gene in the development of macular degeneration allows the production of cell-free and cell-based screening assays and transgenic animals for use in further studies of the disorder and to identify safe and effective MD therapeutics.

The identification of a single gene responsible for ML and DHRD can also improve understanding of the types and classes of genes that can cause related disorders. In addition, the identification of one gene product causing a disorder can make it possible to identify other genes which can cause a similar phenotype. For example, the identification of the dystrophin gene has led to the isolation of dystrophin related glycoproteins, at least one of which plays a role in other forms of muscular dystrophy. Also, a gene capable of causing a Mendelian disorder, may contribute to the inheritance of a multifactorial form of the disorder. A striking example of this has been the identification of genes involved in various forms of cancer (e.g. colon cancer) by studying familial forms of cancer (e.g. hereditary nonpolyposis colon cancer and familial adenomatous polyposis). Groden, J. A. et al.,(1991) *Cell* 66:589–600 ; Aaltonen, L. A. (1993) *Science* 260:812–816). For example, as shown herein, AMD appears to be allelic to Doyne's macular dystrophy

4.2 Definitions

For convenience, the meaning of certain terms and phrases employed in the specification, examples, and appended claims are provided below.

The term "an aberrant activity", as applied to an activity of a polypeptide such as, EFEMP1 refers to an activity which differs from the activity of the wild-type or native polypeptide or which differs from the activity of the polypeptide in a healthy subject. An activity of a polypeptide can be aberrant because it is stronger than the activity of its native counterpart. Alternatively, an activity can be aberrant because it is weaker or absent relative to the activity of its native counterpart. An aberrant activity can also be a change in an activity. For example an aberrant polypeptide can interact with a different target peptide or polypeptide. A cell can have an aberrant EFEMP1 activity due to overexpression or underexpression of a wild-type or mutant EFEMP1 polypeptide.

"Biological activity" or "bioactivity" or "activity" or "biological function", which are used interchangeably for the purposes herein, means an effector or antigenic function that is directly or indirectly performed by an EFEMP1 polypeptide (whether in its native or denatured conformation), or by any subsequence thereof. Biological activities include binding to a target peptide. An EFEMP 1 bioactivity can be modulated by directly affecting the binding between an EFEMP1 and an EFEMP1 binding partner. Alternatively, an EFEMP1 bioactivity can be modulated by modulating the level of an EFEMP1 polypeptide, such as by modulating expression of an EFEMP1 gene.

As used herein, the term "bioactive fragment of an EFEMP1 polypeptide" refers to a fragment of a full-length EFEMP1 polypeptide, wherein the fragment specifically mimics or antagonizes the activity of a wild-type EFEMP1 polypeptide. The bioactive fragment preferably is a fragment capable of interacting with an EFEMP 1 binding partner.

"Cells," "host cells" or "recombinant host cells" are terms used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A "chimeric protein" or "fusion protein" is a fusion of a first amino acid sequence encoding one of the subject polypeptides with a second amino acid sequence defining a domain (e.g. polypeptide portion) foreign to and not substantially homologous with any domain of one of the polypeptides. A chimeric protein may present a foreign domain which is found (albeit in a different protein) in an organism which also expresses the first protein, or it may be an "interspecies", "intergenic", etc. fusion of protein structures expressed by different kinds of organisms.

"Complementary" sequences as used herein refer to sequences which have sufficient complementarity to be able to hybridize, forming a stable duplex.

The terms "control" or "control sample" refer to any sample appropriate to the detection technique employed. The control sample may contain the products of the allele detection technique employed or the material to be tested. Further, the controls may be positive or negative controls. By way of example, where the allele detection technique is PCR amplification, followed by size fractionation, the control sample may comprise DNA fragments of an appropriate size. Likewise, where the allele detection technique involves detection of a mutated protein, the control sample may comprise a sample of a mutant protein. However, it is preferred that the control sample comprises the material to be tested.

The phrases "disruption of the gene" and "targeted disruption" or any similar phrase refers to the site specific interruption of a native DNA sequence so as to prevent expression of that gene in the cell as compared to the wild-type copy of the gene. The interruption may be caused by deletions, insertions or modifications to the gene, or any combination thereof.

A "delivery complex" shall mean a targeting means (e.g. a molecule that results in higher affinity binding of a gene, protein, polypeptide or peptide to a target cell surface and/or increased cellular uptake by a target cell). Examples of targeting means include: sterols (e.g. cholesterol), lipids (e.g. a cationic lipid, virosome or liposome), viruses (e.g. adenovirus, adeno-associated virus, and retrovirus) or target cell specific binding agents (e.g. ligands recognized by target cell specific receptors). Preferred complexes are sufficiently stable in vivo to prevent significant uncoupling prior to internalization by the target cell. However, the complex is cleavable under appropriate conditions within the cell so that the gene, protein, polypeptide or peptide is released in a functional form.

As is well known, genes for a particular polypeptide may exist in single or multiple copies within the genome of an individual. Such duplicate genes may be identical or may have certain modifications, including nucleotide substitutions, additions or deletions, which all still code for polypeptides having substantially the same activity. The term "DNA sequence encoding a polypeptide" may thus refer to one or more genes within a particular individual. Moreover, certain differences in nucleotide sequences may exist between individual organisms, which are called alleles. Such allelic differences may or may not result in differences in amino acid sequence of the encoded polypeptide yet still encode a protein with the same biological activity.

An "EFEMP1" gene or protein refers to an "EGF-containing fibrillin-like extracellular matrix protein 1 gene or protein. cDNA encoding a portion of the protein is posted in GenBank under accession number UO3877. The acronym "EFEMP1" includes genes, proteins and portions thereof, which are substantially homologous in structure and function, including fibulin (1 and 2), Fibrillin, nidogen, notch, protein S and Factor IX.

As used herein, the term "gene" or "recombinant gene" refers to a nucleic acid molecule comprising an open reading frame encoding one of the polypeptides of the present invention, including both exon and (optionally) intron sequences. A "recombinant gene" refers to nucleic acid molecule encoding a polypeptide and comprising protein-encoding exon sequences, though it may optionally include intron sequences which are derived from a chromosomal gene. Exemplary recombinant genes encoding the subject polypeptides are represented in the appended Sequence Listing. The term "intron" refers to a DNA sequence present in a given gene which is not translated into protein and is generally found between exons.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, though preferably less than 25% identity, with one of the sequences of the present invention.

"Increased risk" refers to a statistically higher frequency of occurrence of the disease or condition in an individual carrying a particular polymorphic allele in comparison to the frequency of occurrence of the disease or condition in a member of a population that does not carry the particular polymorphic allele.

The term "interact" as used herein is meant to include detectable interactions between molecules, such as can be detected using, for example, a yeast two hybrid assay. The term interact is also meant to include "binding" interactions between molecules. Interactions may be protein-protein or protein-nucleic acid in nature.

The term "isolated" as used herein with respect to nucleic acids, such as DNA or RNA, refers to molecules separated from other DNAs or RNAs, respectively, that are present in the natural source of the macromolecule. For example, an isolated nucleic acid encoding one of the subject polypeptides preferably includes no more than 10 kilobases (kb) of nucleic acid sequence which naturally immediately flanks the gene in genomic DNA, more preferably no more than 5 kb of such naturally occurring flanking sequences, and most preferably less than 1.5 kb of such naturally occurring flanking sequence. The term isolated as used herein also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to polypeptides which are isolated from other cellular proteins and is meant to encompass both purified and recombinant polypeptides. A "knock-in" transgenic animal refers to an animal that has had a modified gene introduced into its genome and the modified gene can be of exogenous or endogenous origin.

A "knock-out" transgenic animal refers to an animal in which there is partial or complete suppression of the expression of an endogenous gene (e.g, based on deletion of at least a portion of the gene, replacement of at least a portion of the gene with a second sequence, introduction of stop codons, the mutation of bases encoding critical amino acids, or the removal of an intron junction, etc.).

A "knock-out construct" refers to a nucleic acid sequence that can be used to decrease or suppress expression of a protein encoded by endogenous DNA sequences in a cell.

"Linkage disequilibrium" refers to co-inheritance of two alleles at frequencies greater than would be expected from the separate frequencies of occurrence of each allele in a given control population. The expected frequency of occurrence of two alleles that are inherited independently is the frequency of the first allele multiplied by the frequency of the second allele. As used herein, the term "linkage disequilibrium" also refers to linked sequences. Alleles that co-occur at expected frequencies are said to be in "linkage equilibrium" or "not linked." When referring to allelic patterns that are comprised of more than one allele, a first allelic pattern is in linkage disequilibrium with a second allelic pattern if all the alleles that comprise the first allelic pattern are in linkage disequilibrium with at least one of the alleles of the second allelic pattern.

"MD" or "Macular Degeneration" is a clinical term that is used to describe a variety of diseases that are all characterized by a progressive loss of central vision associated with abnormalities of Bruch's membrane and the retinal pigment epithelium. These disorders include very common conditions that affect older patients (age related macular degeneration or AMD) as well as rarer, earlier-onset dystrophies that in some cases can be detected in the first few decades of life. Examples include Malattia Leventinese (ML) and Doyne's Honeycomb Retinal Dystrophy (DHRD).

An "MD therapeutic" refers to an agent that is useful in treating or preventing the development of a Macular Degeneration. Examples include genes, proteins (e.g. glycosylated or unglycosylated protein, polypeptide or protein) or other organic or inorganic molecules (e.g. small molecules) that interfere with or compensate for the biochemical events that are causative of MD.

A "mutated gene" or "mutation" or "functional mutation" refers to an allelic form of a gene, which is capable of altering the phenotype of a subject having the mutated gene relative to a subject which does not have the mutated gene. The altered phenotype caused by a mutation can be corrected or compensated for by certain agents. If a subject must be homozygous for this mutation to have an altered phenotype, the mutation is said to be recessive. If one copy of the mutated gene is sufficient to alter the phenotype of the subject, the mutation is said to be dominant. If a subject has one copy of the mutated gene and has a phenotype that is intermediate between that of a homozygous and that of a heterozygous subject (for that gene), the mutation is said to be co-dominant.

The "non-human animals" of the invention include mammalians such as rodents, non-human primates, sheep, dog, cow, chickens, amphibians, reptiles, etc. Preferred non-human animals are selected from the rodent family including rat and mouse, most preferably mouse. The term "chimeric animal" is used herein to refer to animals in which the recombinant gene is found, or in which the recombinant gene is expressed in some but not all cells of the animal. The term "tissue-specific chimeric animal" indicates that one of the recombinant genes is present and/or expressed or disrupted in some tissues but not others.

As used herein, the term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides.

As used herein, the term "promoter" means a DNA sequence that regulates expression of a selected DNA sequence operably linked to the promoter, and which effects expression of the selected DNA sequence in cells. The term encompasses "tissue specific" promoters, i.e. promoters, which effect expression of the selected DNA sequence only in specific cells (e.g. cells of a specific tissue). The term also covers so-called "leaky" promoters, which regulate expression of a selected DNA primarily in one tissue, but cause expression in other tissues as well. The term also encompasses non-tissue specific promoters and promoters that constitutively express or that are inducible (i.e. expression levels can be controlled).

The terms "protein", "polypeptide" and "peptide" are used interchangeably herein when referring to a gene product.

The term "recombinant protein" refers to a polypeptide of the present invention which is produced by recombinant DNA techniques, wherein generally, DNA encoding a polypeptide is inserted into a suitable expression vector which is in turn used to transform a host cell to produce the heterologous protein. Moreover, the phrase "derived from", with respect to a recombinant gene, is meant to include within the meaning of "recombinant protein" those proteins having an amino acid sequence of a native protein, or an amino acid sequence similar thereto which is generated by mutations including substitutions and deletions (including truncation) of a naturally occurring form of the protein.

"Small molecule" as used herein, is meant to refer to a composition, which has a molecular weight of less than about 5 kD and most preferably less than about 4 kD. Small molecules can be nucleic acids, peptides, peptidomimetics, carbohydrates, lipids or other organic or inorganic molecules.

As used herein, the term "specifically hybridizes" or "specifically detects" refers to the ability of a nucleic acid molecule of the invention to hybridize to at least approximately 6, 12, 20, 30, 50, 100, 150, 200, 300, 350, 400 or 425 consecutive nucleotides.

"Transcriptional regulatory sequence" is a generic term used throughout the specification to refer to DNA sequences, such as initiation signals, enhancers, and promoters, which induce or control transcription of protein coding sequences with which they are operably linked. In preferred embodiments, transcription of one of the recombinant genes is under the control of a promoter sequence (or other transcriptional regulatory sequence) which controls the expression of the recombinant gene in a cell-type in which expression is intended. It will also be understood that the recombinant gene can be under the control of transcriptional regulatory sequences which are the same or which are different from those sequences which control transcription of the naturally-occurring forms of proteins.

As used herein, the term "transfection" means the introduction of a nucleic acid, e.g., an expression vector, into a recipient cell by nucleic acid-mediated gene transfer. "Transformation", as used herein, refers to a process in which a cell's genotype is changed as a result of the cellular uptake of exogenous DNA or RNA, and, for example, the transformed cell expresses a recombinant form of a polypeptide or, in the case of anti-sense expression from the transferred gene, the expression of a naturally-occurring form of the protein is disrupted.

As used herein, the term "transgene" means a nucleic acid sequence encoding, e.g., one of the polypeptides, or an antisense transcript thereto, which is partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). A transgene can include one or more transcriptional regulatory sequences and any other nucleic acid, (e.g. as intron), that may be necessary for optimal expression of a selected nucleic acid.

A "transgenic animal" refers to any animal, preferably a non-human mammal, bird or an amphibian, in which one or more of the cells of the animal contain heterologous nucleic acid introduced by way of human intervention, such as by transgenic techniques well known in the art. The nucleic acid is introduced into the cell, directly or indirectly by introduction into a precursor of the cell, by way of deliberate genetic manipulation, such as by microinjection or by infection with a recombinant virus. The term genetic manipulation does not include classical cross-breeding, or in vitro fertilization, but rather is directed to the introduction of a recombinant DNA molecule. This molecule may be integrated within a chromosome, or it may be extrachromosomally replicating DNA. In the typical transgenic animals described herein, the transgene causes cells to express a recombinant form of one of the proteins, e.g. either agonistic or antagonistic forms. However, transgenic animals in which the recombinant gene is silent are also contemplated, as for example, the FLP or CRE recombinase dependent constructs described below. Moreover, "transgenic animal" also includes those recombinant animals ("knockouts") in which gene disruption of one or more genes is caused by human intervention, including both recombination and antisense techniques.

As used herein, the term "vector" refers to a nucleic acid molecule capable of transporting another nucleic acid to which it has been linked. One type of preferred vector is an episome, i.e., a nucleic acid capable of extra-chromosomal replication. Preferred vectors are those capable of autonomous replication and/expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer generally to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

The term "treating" as used herein is intended to encompass curing as well as ameliorating at least one symptom of a condition or disease.

The term "wild-type allele" refers to an allele of a gene which, when present in two copies in a subject results in a wild-type phenotype. There can be several different wild-type alleles of a specific gene, since certain nucleotide changes in a gene may not affect the phenotype of a subject having two copies of the gene with the nucleotide changes.

4.3. Nucleic Acids of the Present Invention

The invention provides EFEMP1 nucleic acids, homologs thereof, and portions thereof. Preferred nucleic acids have a sequence at least about 60%, 61%, 62%, 63%, 64%, 65%, 66%, 67%, 68%, 69%, 70%, 71%, 72%, 73%, 74%, 75%, 76%, 77%, 78%, 79%, 80%, and more preferably 85%, 90%, 95% homologous and more preferably 98% and even more preferably at least 99% homologous with a nucleotide sequence of an EFEMP1 gene, e.g., such as a sequence shown in one of FIG. 5 or complement thereof. In preferred embodiments, the nucleic acid is mammalian and in particularly preferred embodiments, includes all or a portion of the nucleotide sequence corresponding to the coding region of one of FIG. 5.

The invention also pertains to isolated nucleic acids comprising a nucleotide sequence encoding EFEMP1 polypeptides, variants and/or equivalents of such nucleic acids. The term equivalent is understood to include nucleotide sequences encoding functionally equivalent EFEMP 1 polypeptides or functionally equivalent peptides having an activity of an EFEMP1 protein such as described herein. Equivalent nucleotide sequences will include sequences that differ by one or more nucleotide substitution, addition or deletion, such as allelic variants; and will, therefore, include sequences that differ from the nucleotide sequence of the EFEMP1 gene shown in FIG. 5 due to the degeneracy of the genetic code.

Preferred nucleic acids are vertebrate EFEMP1 nucleic acids. Particularly preferred vertebrate EFEMP1 nucleic acids are mammalian. Regardless of species, particularly preferred EFEMP1 nucleic acids encode polypeptides that are at least 60%, 65%, 70%, 72%, 74%, 76%, 78%, 80%, 90%, or 95% similar or identical to an amino acid sequence of a vertebrate EFEMP1 protein. In one embodiment, the nucleic acid is a cDNA encoding a polypeptide having at least one bioactivity of the subject EFEMP1 polypeptide. Preferably, the nucleic acid includes all or a portion of the nucleotide sequence corresponding to the nucleic acid of FIG. 5.

Still other preferred nucleic acids of the present invention encode an EFEMP1 polypeptide which is comprised of at least 2, 5, 10, 25, 50, 100, 150, 200, 250, 300, 350 or 400 amino acid residues. For example, such nucleic acids can comprise about 50, 60, 70, 80, 90, or 100 base pairs. Also within the scope of the invention are nucleic acid molecules for use as probes/primer or antisense molecules (i.e. non-coding nucleic acid molecules), which can comprise at least about 6, 12, 20, 30, 50, 60, 70, 80, 90 or 100 base pairs in length.

Another aspect of the invention provides a nucleic acid which hybridizes under stringent conditions to a nucleic acid represented by FIG. 5 or complement thereof. Appropriate stringency conditions which promote DNA hybridization, for example, 6.0×sodium chloride/sodium citrate (SSC) at about 45° C., followed by a wash of 2.0×SSC at 50° C., are known to those skilled in the art or can be found in Current Protocols in Molecular Biology, John Wiley & Sons, N.Y. (1989), 6.3.1–6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or temperature and salt concentration may be held constant while the other variable is changed. In a preferred embodiment, an MFGF nucleic acid of the present invention will bind to one of SEQ ID NO. 2, 3, or 5 or the sequence shown in FIG. 5 or complement thereof under moderately stringent conditions, for example at about 2.0×SSC and about 40° C. In a particularly preferred embodiment, an MFGF nucleic acid of the present invention will bind to one of SEQ ID NOS. 2, 3, or 5 or the sequence shown in FIG. 5 or complement thereof under high stringency conditions.

Nucleic acids having a sequence that differs from the nucleotide sequences shown FIG. 5 or complement thereof due to degeneracy in the genetic code are also within the scope of the invention. Such nucleic acids encode functionally equivalent peptides (i.e., peptides having a biological activity of an EFEMP1 polypeptide) but differ in sequence from the sequence shown in the sequence listing due to degeneracy in the genetic code. For example, a number of amino acids are designated by more than one triplet. Codons that specify the same amino acid, or synonyms (for example, CAU and CAC each encode histidine) may result in "silent" mutations which do not affect the amino acid sequence of an EFEMP1 polypeptide. However, it is expected that DNA sequence polymorphisms that do lead to changes in the amino acid sequences of the subject EFEMP1 polypeptides will exist among mammals. One skilled in the art will appreciate that these variations in one or more nucleotides (e.g., up to about 3–5% of the nucleotides) of the nucleic acids encoding polypeptides having an activity of an EFEMP1 polypeptide may exist among individuals of a given species due to natural allelic variation.

Nucleic acids of the invention can encode one or more domains of an EFEMP1 protein (e.g. the EGF domain). Other preferred nucleic acids of the invention include nucleic acids encoding derivatives of EFEMP1 polypeptides which lack one or more biological activities of EFEMP1 polypeptides. Such nucleic acids can be obtained, e.g., by a first round of screening of libraries for the presence or absence of a first activity and a second round of screening for the presence or absence of another activity.

Also within the scope of the invention are nucleic acids encoding splice variants or nucleic acids representing transcripts synthesized from an alternative transcriptional initiation site, such as those whose transcription was initiated from a site in an intron.

In preferred embodiments, the EFEMP1 nucleic acids can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids (see Hyrup B. et al. (1996) *Bioorganic & Medicinal Chemistry* 4 (1): 5–23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup B. et al. (1996) supra; Perry-O'Keefe et al. *PNAS* 93: 14670–675.

Such modified nucleic acids can be used as antisense or antigene agents for sequence-specific modulation of gene expression or in the analysis of single base pair mutations in a gene by, e.g., PNA directed PCR clamping or as probes or primers for DNA sequence and hybridization (Hyrup B. et al (1996) supra; Perry-O'Keefe supra).

PNAs can further be modified, e.g., to enhance their stability or cellular uptake, e.g., by attaching lipophilic or other helper groups to the PNA, by the formation of PNA-DNA chimeras, or by the use of liposomes or other techniques of drug delivery known in the art. MFGF PNAs can also be linked to DNA as described, e.g., in Hyrup B. (1996) supra and Finn P. J. et al. (1996) *Nucleic Acids Research* 24 (17): 3357–63. For example, a DNA chain can be synthesized on a solid support using standard phosphoramidite coupling chemistry and modified nucleoside analogs, e.g., 5'-(4-methoxytrityl)amino-5'-deoxy-thymidine phosphoramidite, can be used between the PNA and the 5' end of DNA (Mag, M. et al. (1989) *Nucleic Acid Res.* 17: 5973–88). PNA monomers are then coupled in a stepwise manner to produce a chimeric molecule with a 5'PNA segment and a 3' DNA segment (Finn P. J. et al. (1996) supra). Alternatively, chimeric molecules can be synthesized with a 5' DNA segment and a 3' PNA segment (Peterser, K. H. et al. (1 975) *Bioorganic Med Chem. Lett.* 5: 1119–11124).

In other embodiments, EFEMP 1 nucleic acids may include other appended groups such as peptides (e.g., for targeting host cell receptors in vivo), or agents that facilitate transport across the cell membrane.

4.3.1 Probes and Primers

The nucleotide sequences determined from the cloning of EFEMP1 genes from mammalian organisms will further allow for the generation of probes and primers designed for use in identifying and/or cloning EFEMP1 homologs in other cell types, e.g., from other tissues, as well as EFEMP1 homologs from other mammalian organisms. For instance, the present invention also provides a probe/primer comprising a substantially purified oligonucleotide, which oligonucleotide comprises a region of nucleotide sequence that hybridizes under stringent conditions to at least approximately 12, preferably 25, more preferably 40, 50 or 75 consecutive nucleotides of sense or anti-sense sequence selected from FIG. 5 or naturally occurring mutants thereof. For instance, primers based on the nucleic acid represented in FIG. 5 can be used in PCR reactions to clone EFEMP1 homologs.

Likewise, probes based on the subject EFEMP1 sequences can be used to detect transcripts or genomic sequences encoding the same or homologous proteins, for use, e.g., in prognostic or diagnostic assays (further described below). In preferred embodiments, the probe further comprises a label group attached thereto and able to be detected, e.g., the label group is selected from amongst radioisotopes, fluorescent compounds, enzymes, and enzyme co-factors.

Probes and primers can be prepared and modified, e.g., as previously described herein for other types of nucleic acids.

4.3.2 Antisense, Ribozyme and Triplex techniques

Another aspect of the invention relates to the use of the isolated nucleic acid in "antisense" therapy. As used herein, "antisense" therapy refers to administration or in situ generation of oligonucleotide molecules or their derivatives which specifically hybridize (e.g., bind) under cellular conditions, with the cellular mRNA and/or genomic DNA encoding one or more of the subject EFEMP1 proteins so as to inhibit expression of that protein, e.g., by inhibiting transcription and/or translation. The binding may be by conventional base pair complementarity, or, for example, in the case of binding to DNA duplexes, through specific interactions in the major groove of the double helix. In general, "antisense" therapy refers to the range of techniques generally employed in the art, and includes any therapy which relies on specific binding to oligonucleotide sequences.

An antisense construct of the present invention can be delivered, for example, as an expression plasmid which, when transcribed in the cell, produces RNA which is complementary to at least a unique portion of the cellular mRNA which encodes an EFEMP1 protein. Alternatively, the antisense construct is an oligonucleotide probe which is generated ex vivo and which, when introduced into the cell causes inhibition of expression by hybridizing with the mRNA and/or genomic sequences of an EFEMP1 gene. Such oligonucleotide probes are preferably modified oligonucleotides which are resistant to endogenous nucleases, e.g., exonucleases and/or endonucleases, and are therefore stable in vivo. Exemplary nucleic acid molecules for use as antisense oligonucleotides are phosphoramidate, phosphothioate and methylphosphonate analogs of DNA (see also U.S. Pat. Nos. 5,176,996; 5,264,564; and 5,256,775). Additionally, general approaches to constructing oligomers useful in antisense therapy have been reviewed, for example, by Van der Krol et al. (1988) BioTechniques 6:958–976; and Stein et al. (1988) Cancer Res 48:2659–2668. With respect to antisense DNA, oligodeoxyribonucleotides derived from the translation initiation site, e.g., between the −10 and +10 regions of the EFEMP1 nucleotide sequence of interest, are preferred.

Antisense approaches involve the design of oligonucleotides (either DNA or RNA) that are complementary to EFEMP1 mRNA. The antisense oligonucleotides will bind to the EFEMP1 mRNA transcripts and prevent translation. Absolute complementarity, although preferred, is not required. In the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

Oligonucleotides that are complementary to the 5' end of the mRNA, e.g., the 5' untranslated sequence up to and including the AUG initiation codon, should work most efficiently at inhibiting translation. However, sequences complementary to the 3' untranslated sequences of mRNAs have recently been shown to be effective at inhibiting translation of mRNAs as well. (Wagner, R. 1994. Nature 372:333). Therefore, oligonucleotides complementary to either the 5' or 3' untranslated, non-coding regions of an EFEMP1 gene could be used in an antisense approach to inhibit translation of endogenous EFEMP1 mRNA. Oligonucleotides complementary to the 5' untranslated region of the mRNA should include the complement of the AUG start codon. Antisense oligonucleotides complementary to mRNA coding regions are less efficient inhibitors of translation but could also be used in accordance with the invention. Whether designed to hybridize to the 5', 3' or coding region of EFEMP1 mRNA, antisense nucleic acids should be at least six nucleotides in length, and are preferably less than about 100 and more preferably less than about 50, 25, 17 or 10 nucleotides in length.

Regardless of the choice of target sequence, it is preferred that in vitro studies are first performed to quantitate the ability of the antisense oligonucleotide to inhibit gene expression. It is preferred that these studies utilize controls that distinguish between antisense gene inhibition and non-specific biological effects of oligonucleotides. It is also preferred that these studies compare levels of the target RNA or protein with that of an internal control RNA or protein. Additionally, it is envisioned that results obtained using the antisense oligonucleotide are compared with those obtained using a control oligonucleotide. It is preferred that the control oligonucleotide is of approximately the same length as the test oligonucleotide and that the nucleotide sequence of the oligonucleotide differs from the antisense sequence no more than is necessary to prevent specific hybridization to the target sequence.

The oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors), or agents facilitating transport across the cell membrane (see, e.g., Letsinger et al., 1989, Proc. Natl. Acad. Sci. U.S.A. 86:6553–6556; Lemaitre et al., 1987, Proc. Natl. Acad. Sci. 84:648–652; PCT Publication No. WO88/09810, published Dec. 15, 1988) or the blood-brain barrier (see, e.g., PCT Publication No. WO89/10134, published Apr. 25, 1988), hybridization-triggered cleavage agents. (See, e.g., Krol et al., 1988, BioTechniques 6:958–976) or intercalating agents. (See, e.g., Zon, 1988, Pharm. Res. 5:539–549). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including but not limited to 5-fluorouracil, 5-bromouracil, 5-chlorouracil, 5-iodouracil, hypoxanthine, xantine, 4-acetylcytosine, 5-(carboxyhydroxytiethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5- oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

The antisense oligonucleotide may also comprise at least one modified sugar moiety selected from the group including but not limited to arabinose, 2-fluoroarabinose, xylulose, and hexose.

The antisense oligonucleotide can also contain a neutral peptide-like backbone. Such molecules are termed peptide nucleic acid (PNA)-oligomers and are described, e.g., in Perry-O'Keefe et al. (1996) Proc. Natl. Acad. Sci. U.S.A. 93:14670 and in Eglom et al. (1993) Nature 365:566. One advantage of PNA oligomers is their ability to bind to complementary DNA essentially independently from the ionic strength of the medium due to the neutral backbone of the DNA. In yet another embodiment, the antisense oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet a further embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier et al., 1987, Nucl. Acids Res. 15:6625–6641). The oligonucleotide is a 2'-0-methylribonucleotide (Inoue et al., 1987, Nucl. Acids Res. 15:6131–6148), or a chimeric RNA-DNA analogue (Inoue et al., 1987, FEBS Lett. 215:327–330).

Oligonucleotides of the invention may be synthesized by standard methods known in the art, e.g., by use of an automated DNA synthesizer (such as are commercially available from Biosearch, Applied Biosystems, etc.). As examples, phosphorothioate oligonucleotides may be synthesized by the method of Stein et al. (1988, Nucl. Acids Res. 16:3209), methylphosphonate olgonucleotides can be prepared by use of controlled pore glass polymer supports (Sarin et al., 1988, Proc. Natl. Acad. Sci. U.S.A. 85:7448–7451), etc.

While antisense nucleotides complementary to the EFEMP1 coding region sequence can be used, those complementary to the transcribed untranslated region and to the region comprising the initiating methionine are most preferred.

The antisense molecules can be delivered to cells which express EFEMP1 in vivo. A number of methods have been developed for delivering antisense DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systematically.

However, it may be difficult to achieve intracellular concentrations of the antisense sufficient to suppress translation on endogenous mRNAs in certain instances. Therefore a preferred approach utilizes a recombinant DNA construct in which the antisense oligonucleotide is placed under the control of a strong pol III or pol II promoter. The use of such a construct to transfect target cells in the patient will result in the transcription of sufficient amounts of single stranded RNAs that will form complementary base pairs with the endogenous EFEMP1 transcripts and thereby prevent translation of the EFEMP1 mRNA. For example, a vector can be introduced in vivo such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the antisense RNA can be by any promoter known in the art to act in mammalian, preferably human cells. Such promoters can be inducible or constitutive and can include but not be limited to: the SV40 early promoter region (Bernoist and Chambon, 1981, Nature 290:304–310), the promoter contained in the 3' long terminal repeat of Rous sarcoma virus (Yamamoto et al., 1980, Cell 22:787–797), the herpes thymidine kinase promoter (Wagner et al., 1981, Proc. Natl. Acad. Sci. U.S.A. 78:1441–1445), the regulatory sequences of the metallothionein gene (Brinster et al, 1982, Nature 296:39–42), etc. Any type of plasmid, cosmid, YAC or viral vector can be used to prepare the recombinant DNA construct which can be introduced directly into the tissue site. Alternatively, viral vectors can be used which selectively infect the desired tissue, in which case administration may be accomplished by another route (e.g., systematically).

Ribozyme molecules designed to catalytically cleave EFEMP1 mRNA transcripts can also be used to prevent translation of EFEMP1 mRNA and expression of EFEMP1 (See, e.g., PCT International Publication WO90/11364, published Oct. 4, 1990; Sarver et al., 1990, Science 247:1222–1225 and U.S. Pat. No. 5,093,246). While ribozymes that cleave mRNA at site specific recognition sequences can be used to destroy EFEMP1 mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, 1988, Nature, 334:585–591. There are a number of potential hammerhead ribozyme cleavage sites within the nucleotide sequence of human EFEMP1 cDNA. Preferably the ribozyme is engineered so that the cleavage recognition site is located near the 5' end of the EFEMP1 mRNA; i.e., to increase efficiency and minimize the intracellular accumulation of non-functional mRNA transcripts.

The ribozymes of the present invention also include RNA endoribonucleases (hereinafter "Cech-type ribozymes") such as the one which occurs naturally in *Tetrahymena thermophila* (known as the IVS, or L-19 IVS RNA) and which has been extensively described by Thomas Cech and collaborators (Zaug, et al., 1984, Science, 224:574–578; Zaug and Cech, 1986, Science, 231:470–475; Zaug, et al., 1986, Nature, 324:429–433; published International patent application No. WO88/04300 by University Patents Inc.; Been and Cech, 1986, Cell, 47:207–216). The Cech-type ribozymes have an eight base pair active site which hybridizes to a target RNA sequence whereafter cleavage of the target RNA takes place. The invention encompasses those Cech-type ribozymes which target eight base-pair active site sequences that are present in an EFEMP1 gene.

As in the antisense approach, the ribozymes can be composed of modified oligonucleotides (e.g., for improved stability, targeting, etc.) and should be delivered to cells which express the EFEMP1 gene in vivo. A preferred method of delivery involves using a DNA construct "encoding" the ribozyme under the control of a strong constitutive pol III or pol II promoter, so that transfected cells will produce sufficient quantities of the ribozyme to destroy endogenous EFEMP1 messages and inhibit translation. Because ribozymes unlike antisense molecules, are catalytic, a lower intracellular concentration is required for efficiency.

Endogenous EFEMP1 gene expression can also be reduced by inactivating or "knocking out" the EFEMP1 gene or its promoter using targeted homologous recombination. (E.g., see Smithies et al., 1985, Nature 317:230–234; Thomas & Capecchi, 1987, Cell 51:503–512; Thompson et al., 1989 Cell 5:313–321; each of which is incorporated by reference herein in its entirety). For example, a mutant, non-functional EFEMP1 (or a completely unrelated DNA sequence) flanked by DNA homologous to the endogenous EFEMP1 gene (either the coding regions or regulatory regions of the EFEMP1 gene) can be used, with or without a selectable marker and/or a negative selectable marker, to transfect cells that express EFEMP1 in vivo. Insertion of the DNA construct, via targeted homologous recombination, results in inactivation of the EFEMP1 gene. Such approaches are particularly suited in the agricultural field where modifications to ES (embryonic stem) cells can be used to generate animal offspring with an inactive EFEMP1 (e.g., see Thomas & Capecchi 1987 and Thompson 1989, supra). However this approach can be adapted for use in humans provided the recombinant DNA constructs are directly administered or targeted to the required site in vivo using appropriate viral vectors.

Alternatively, endogenous EFEMP1 gene expression can be reduced by targeting deoxyribonucleotide sequences complementary to the regulatory region of the EFEMP1 gene (i.e., the EFEMP1 promoter and/or enhancers) to form triple helical structures that prevent transcription of the EFEMP1 gene in target cells in the body. (See generally, Helene, C. 1991, Anticancer Drug Des., 6(6):569–84; Helene, C., et al., 1992, Ann. N.Y. Acad. Sci., 660:27–36; and Maher, L. J., 1992, Bioassays 14(12):807–15).

Nucleic acid molecules to be used in triple helix formation for the inhibition of transcription are preferably single stranded and composed of deoxyribonucleotides. The base composition of these oligonucleotides should promote triple helix formation via Hoogsteen base pairing rules, which generally require sizable stretches of either purines or pyrimidines to be present on one strand of a duplex. Nucleotide sequences may be pyrimidine-based, which will result in TAT and CGC triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, for example, containing a stretch of G residues. These molecules will form a triple helix with a DNA duplex that is rich in GC pairs, in which the majority of the purine residues are located on a single strand of the targeted duplex, resulting in CGC triplets across the three strands in the triplex.

Alternatively, the potential sequences that can be targeted for triple helix formation may be increased by creating a so called "switchback" nucleic acid molecule. Switchback molecules are synthesized in an alternating 5'-3', 3'-5' manner, such that they base pair with first one strand of a duplex and then the other, eliminating the necessity for a sizable stretch of either purines or pyrimidines to be present on one strand of a duplex.

Antisense RNA and DNA, ribozyme, and triple helix molecules of the invention may be prepared by any method known in the art for the synthesis of DNA and RNA molecules. These include techniques for chemically synthesizing oligodeoxyribonucleotides and oligoribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Moreover, various well-known modifications to nucleic acid molecules may be introduced as a means of increasing intracellular stability and half-life. Possible modifications include but are not limited to the addition of flanking sequences of ribonucleotides or deoxyribonucleotides to the 5' and/or 3' ends of the molecule or the use of phosphorothioate or 2' O-methyl rather than phosphodiesterase linkages within the oligodeoxyribonucleotide backbone.

4.3.3. Vectors Encoding MFGF Proteins and MFGF Expressing Cells

The invention further provides plasmids and vectors encoding an EFEMP1 protein, which can be used to express an EFEMP1 protein in a host cell. The host cell may be any prokaryotic or eukaryotic cell. Thus, a nucleotide sequence derived from the cloning of mammalian EFEMP1 proteins, encoding all or a selected portion of the full-length protein, can be used to produce a recombinant form of an EFEMP1 polypeptide via microbial or eukaryotic cellular processes. Ligating the polynucleotide sequence into a gene construct, such as an expression vector, and transforming or transfecting into hosts, either eukaryotic (yeast, avian, insect or mammalian) or prokaryotic (bacterial) cells, are standard procedures well known in the art.

Vectors that allow expression of a nucleic acid in a cell are referred to as expression vectors. Typically, expression vectors used for expressing an EFEMP1 protein contain a nucleic acid encoding an EFEMP1 polypeptide, operably linked to at least one transcriptional regulatory sequence. Regulatory sequences are art-recognized and are selected to direct expression of the subject EFEMP1 proteins. Transcriptional regulatory sequences are described in Goeddel; Gene Expression Technology: Methods in Enzymology 185, Academic Press, San Diego, Cailf. (1990). In one embodiment, the expression vector includes a recombinant gene encoding a peptide having an agonistic activity of a subject EFEMP1 polypeptide, or alternatively, encoding a peptide which is an antagonistic form of an EFEMP1 protein.

Suitable vectors for the expression of an EFEMP1 polypeptide include plasmids of the types: pBR322-derived plasmids, pEMBL-derived plasmids, pEX-derived plasmids, pBTac-derived plasmids and pUC-derived plasmids for expression in prokaryotic cells, such as $E.\ coli$.

A number of vectors exist for the expression of recombinant proteins in yeast. For instance, YEP24, YIP5, YEP51, YEP52, pYES2, and YRP17 are cloning and expression vehicles useful in the introduction of genetic constructs into $S.\ cerevisiae$ (see, for example, Broach et al. (1983) in Experimental Manipulation of Gene Expression, ed. M. Inouye Academic Press, p.83, incorporated by reference herein). These vectors can replicate in $E.\ coli$ due the presence of the pBR322 ori, and in $S.\ cerevisiae$ due to the replication determinant of the yeast 2 micron plasmid. In addition, drug resistance markers such as ampicillin can be used. In an illustrative embodiment, an MFGF polypeptide is produced recombinantly utilizing an expression vector generated by sub-cloning the coding sequence of one of the EFEMP1 genes represented FIG. 5.

The preferred mammalian expression vectors contain both prokaryotic sequences, to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papillomavirus (BPV-1), or Epstein-Barr virus (pHEBo, pREP-derived and p205) can be used for transient expression of proteins in eukaryotic cells. The various methods employed in the preparation of the plasmids and transformation of host organisms are well known in the art. For other suitable expression systems for both prokaryotic and eukaryotic cells, as well as general recombinant procedures, see Molecular Cloning A Laboratory Manual, $2^{nd}$ Ed., ed. by Sambrook, Fritsch and Maniatis (Cold Spring Harbor Laboratory Press: 1989) Chapters 16 and 17.

In some instances, it may be desirable to express the recombinant EFEMP1 polypeptide by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III)

When it is desirable to express only a portion of an EFEMP1 protein, such as a form lacking a portion of the N-terminus, i.e. a truncation mutant which lacks the signal peptide, it may be necessary to add a start codon (ATG) to the oligonucleotide fragment containing the desired sequence to be expressed. It is well known in the art that a methionine at the N-terminal position can be enzymatically cleaved by the use of the enzyme methionine aminopeptidase (MAP). MAP has been cloned from $E.\ coli$ (Ben-Bassat et al. (1987) J. Bacteriol. 169:751–757) and $Salmonella$ $typhimurium$ and its in vitro activity has been demonstrated on recombinant proteins (Miller et al. (1987) PNAS 84:2718–1722). Therefore, removal of an N-terminal methionine, if desired, can be achieved either in vivo by expressing MFGF derived polypeptides in a host which produces MAP (e.g., $E.\ coli$ or CM89 or $S.\ cerevisiae$), or in vitro by use of purified MAP (e.g., procedure of Miller et al., supra).

Moreover, the gene constructs of the present invention can also be used as part of a gene therapy protocol to deliver nucleic acids encoding either an agonistic or antagonistic form of one of the subject EFEMP1 proteins. Thus, another aspect of the invention features expression vectors for in vivo or in vitro transfection and expression of an EFEMP 1 polypeptide in particular cell types so as to reconstitute the function of, or alternatively, abrogate the function of EFEMP 1 in a tissue. This could be desirable, for example, when the naturally-occurring form of the protein is misexpressed or the natural protein is mutated and less active.

In addition to viral transfer methods, non-viral methods can also be employed to cause expression of a subject EFEMP1 polypeptide in the tissue of an animal. Most nonviral methods of gene transfer rely on normal mechanisms used by mammalian cells for the uptake and intracellular transport of macromolecules. In preferred embodiments, non-viral targeting means of the present invention rely on endocytic pathways for the uptake of the subject EFEMP1 polypeptide gene by the targeted cell. Exemplary targeting means of this type include liposomal derived systems, poly-lysine conjugates, and artificial viral envelopes.

In other embodiments transgenic animals, described in more detail below could be used to produce recombinant proteins.

4.4. Polypeptides of the Present Invention

The present invention makes available isolated EFEMP1 polypeptides which are isolated from, or otherwise substantially free of other cellular proteins. The term "substantially free of other cellular proteins" (also referred to herein as "contaminating proteins") or "substantially pure or purified preparations" are defined as encompassing preparations of EFEMP1 polypeptides having less than about 20% (by dry weight) contaminating protein, and preferably having less than about 5% contaminating protein. Functional forms of the subject polypeptides can be prepared, for the first time, as purified preparations by using a cloned gene as described herein.

Preferred EFEMP1 proteins of the invention have an amino acid sequence which is at least about 60%, 65%, 66%, 67%, 68%, 69%, 70%, 71%, 72%, 73%, 74%, 75%, 76%, 77%, 78%, 79%, 80%, 85%, 90%, or 95% identical or homologous to an amino acid sequence of SEQ ID NO. 1. Even more preferred EFEMP1 proteins comprise an amino acid sequence which is at least about 97, 98, or 99% homologous or identical to an amino acid sequence of SEQ ID NOS. 1. Such proteins can be recombinant proteins, and can be, e.g., produced in vitro from nucleic acids comprising a nucleotide sequence set forth in FIG. 5 or homologs thereof. For example, recombinant polypeptides preferred by the present invention can be encoded by a nucleic acid, which is at least 85% homologous and more preferably 90% homologous and most preferably 95% homologous with a nucleotide sequence set forth in FIG. 5. Polypeptides which are encoded by a nucleic acid that is at least about 98–99% homologous with the sequence of FIG. 5 are also within the scope of the invention.

In a preferred embodiment, an EFEMP1 protein of the present invention is a mammalian EFEMP1 protein. In a particularly preferred embodiment an EFEMP1 protein is set forth as SEQ ID NO. 1. In particularly preferred embodiments, an EFEMP1 protein has an EFEMP1 bioactivity. It will be understood that certain post-translational modifications, e.g., phosphorylation and the like, can increase the apparent molecular weight of the EFEMP1 protein relative to the unmodified polypeptide chain.

The invention also features protein isoforms encoded by splice variants of the present invention. Such isoforms may have biological activities identical to or different from those possessed by the EFEMP1 protein specified by SEQ ID NO. 1.

EFEMP1 polypeptides preferably are capable of functioning as either an agonist or antagonist of at least one biological activity of a wild-type ("authentic") EFEMP1 protein of the appended sequence listing.

Full length proteins or fragments corresponding to one or more particular motifs and/or domains or to arbitrary sizes, for example, at least 5, 10, 25, 50, 75 and 100, amino acids in length are within the scope of the present invention.

For example, isolated EFEMP1 polypeptides can be encoded by all or a portion of a nucleic acid sequence shown in any of SEQ ID NO. 1. Isolated peptidyl portions of EFEMP1 proteins can be obtained by screening peptides recombinantly produced from the corresponding fragment of the nucleic acid encoding such peptides. In addition, fragments can be chemically synthesized using techniques known in the art such as conventional Merrifield solid phase f-Moc or t-Boc chemistry. For example, an EFEMP1 polypeptide of the present invention may be arbitrarily divided into fragments of desired length with no overlap of the fragments, or preferably divided into overlapping fragments of a desired length. The fragments can be produced (recombinantly or by chemical synthesis) and tested to identify those peptidyl fragments which can function as either agonists or antagonists of a wild-type (e.g., "authentic") EFEMP1 protein. Assays for determining whether a compound, e.g, a protein, such as an EFEMP1 protein or variant thereof, has one or more of the above biological activities are well known in the art.

Other preferred proteins of the invention are fusion proteins, e.g., EFEMP1-immunoglobulin fusion proteins. Such fusion proteins can provide, e.g., enhanced stability and solubility of EFEMP 1 proteins and may thus be useful in therapy. Fusion proteins can also be used to produce an immunogenic fragment of an EFEMP1 protein. For example, the VP6 capsid protein of rotavirus can be used as an immunologic carrier protein for portions of the EFEMP1 polypeptide, either in the monomeric form or in the form of a viral particle. The nucleic acid sequences corresponding to the portion of a subject EFEMP1 protein to which antibodies are to be raised can be incorporated into a fusion gene construct which includes coding sequences for a late vaccinia virus structural protein to produce a set of recombinant viruses expressing fusion proteins comprising MFGF epitopes as part of the virion. It has been demonstrated with the use of immunogenic fusion proteins utilizing the Hepatitis B surface antigen fusion proteins that recombinant Hepatitis B virions can be utilized in this role as well. Similarly, chimeric constructs coding for fusion proteins containing a portion of an EFEMP1 protein and the poliovirus capsid protein can be created to enhance immunogenicity of the set of polypeptide antigens (see, for example, EP Publication No: 0259149; and Evans et al. (1989) Nature 339:385; Huang et al. (1988) J. Virol. 62:3855; and Schlienger et al. (1992) J. Virol. 66:2).

The Multiple antigen peptide system for peptide-based immunization can also be utilized to generate an immunogen, wherein a desired portion of an EFEMP1 polypeptide is obtained directly from organo-chemical synthesis of the peptide onto an oligomeric branching lysine core (see, for example, Posnett et al. (1988) JBC 263:1719 and Nardelli et al. (1992) J. Immunol. 148:914). Antigenic determinants of EFEMP1 proteins can also be expressed and presented by bacterial cells.

In addition to utilizing fusion proteins to enhance immunogenicity, it is widely appreciated that fusion proteins can also facilitate the expression of proteins, and accordingly, can be used in the expression of the EFEMP1 polypeptides of the present invention. For example, EFEMP1 polypeptides can be generated as glutathione-S-transferase (GST-fusion) proteins. Such GST-fusion proteins can enable easy purification of the EFEMP1 polypeptide, as for example by the use of glutathione-derivatized matrices (see, for example, Current Protocols in Molecular Biology, eds. Ausubel et al. (N.Y.: John Wiley & Sons, 1991)).

The present invention further pertains to methods of producing the subject EFEMP1 polypeptides. For example, a host cell transfected with a nucleic acid vector directing expression of a nucleotide sequence encoding the subject polypeptides can be cultured under appropriate conditions to allow expression of the peptide to occur. Suitable media for cell culture are well known in the art. The recombinant EFEMP1 polypeptide can be isolated from cell culture medium, host cells, or both using techniques known in the art for purifying proteins including ion-exchange chromatography, gel filtration chromatography, ultrafiltration, electrophoresis, and immunoaffinity purification with antibodies specific for such peptide. In a preferred embodiment, the recombinant EFEMP1 polypeptide is a fusion protein containing a domain which facilitates its purification, such as GST fusion protein.

Moreover, it will be generally appreciated that, under certain circumstances, it may be advantageous to provide homologs of one of the subject EFEMP1 polypeptides which function in a limited capacity as one of either an EFEMP1 agonist (mimetic) or an EFEMP1 antagonist, in order to promote or inhibit only a subset of the biological activities of the naturally-occurring form of the protein. Thus, specific biological effects can be elicited by treatment with a homolog of limited function, and with fewer side effects relative to treatment with agonists or antagonists which are directed to all of the biological activities of naturally occurring forms of EFEMP1 proteins.

Homologs of each of the subject EFEMP1 proteins can be generated by mutagenesis, such as by discrete point mutation(s), or by truncation. For instance, mutation can give rise to homologs which retain substantially the same, or merely a subset, of the biological activity of the EFEMP1 polypeptide from which it was derived. Alternatively, antagonistic forms of the protein can be generated which are able to inhibit the function of the naturally occurring form of the protein, such as by competitively binding to an EFEMP1 receptor.

The recombinant EFEMP1 polypeptides of the present invention also include homologs of the wild type EFEMP1 proteins, such as versions of those protein which are resistant to proteolytic cleavage, as for example, due to mutations which alter ubiquitination or other enzymatic targeting associated with the protein.

EFEMP1 polypeptides may also be chemically modified to create EFEMP1 derivatives by forming covalent or aggregate conjugates with other chemical moieties, such as glycosyl groups, lipids, phosphate, acetyl groups and the like. Covalent derivatives of EFEMP1 proteins can be prepared by linking the chemical moieties to functional groups on amino acid sidechains of the protein or at the N-terminus or at the C-terminus of the polypeptide.

Modification of the structure of the subject EFEMP1 polypeptides can be for such purposes as enhancing therapeutic or prophylactic efficacy, stability (e.g., ex vivo shelf life and resistance to proteolytic degradation), or post-translational modifications (e.g., to alter phosphorylation pattern of protein). Such modified peptides, when designed to retain at least one activity of the naturally-occurring form of the protein, or to produce specific antagonists thereof, are considered functional equivalents of the EFEMP1 polypeptides described in more detail herein. Such modified peptides can be produced, for instance, by amino acid substitution, deletion, or addition. The substitutional variant may be a substituted conserved amino acid or a substituted non-conserved amino acid.

For example, it is reasonable to expect that an isolated replacement of a leucine with an isoleucine or valine, an aspartate with a glutamate, a threonine with a serine, or a similar replacement of an amino acid with a structurally related amino acid (i.e. isosteric and/or isoelectric mutations) will not have a major effect on the biological activity of the resulting molecule. Conservative replacements are those that take place within a family of amino acids that are related in their side chains. Genetically encoded amino acids can be divided into four families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. In similar fashion, the amino acid repertoire can be grouped as (1) acidic=aspartate, glutamate; (2) basic=lysine, arginine histidine, (3) aliphatic=glycine, alanine, valine, leucine, isoleucine, serine, threonine, with serine and threonine optionally be grouped separately as aliphatic-hydroxyl; (4) aromatic=phenylalanine, tyrosine, tryptophan; (5) amide=asparagine, glutamine; and (6) sulfur-containing=cysteine and methionine. (see, for example, Biochemistry, $2^{nd}$ ed., Ed. by L. Stryer, WH Freeman and Co.: 1981). Whether a change in the amino acid sequence of a peptide results in a functional MFGF homolog (e.g., functional in the sense that the resulting polypeptide mimics or antagonizes the wild-type form) can be readily determined by assessing the ability of the variant peptide to produce a response in cells in a fashion similar to the wild-type protein, or competitively inhibit such a response. Polypeptides in which more than one replacement has taken place can readily be tested in the same manner.

This invention further contemplates a method for generating sets of combinatorial mutants of the subject EFEMP1 proteins as well as truncation mutants, and is especially useful for identifying potential variant sequences (e.g., homologs). The purpose of screening such combinatorial libraries is to generate, for example, novel EFEMP1 homologs which can act as either agonists or antagonist, or alternatively, possess novel activities all together. Thus, combinatorially-derived homologs can be generated to have an increased potency relative to a naturally occurring form of the protein.

In one embodiment, the variegated library of EFEMP1 variants is generated by combinatorial mutagenesis at the nucleic acid level, and is encoded by a variegated gene library. For instance, a mixture of synthetic oligonucleotides can be enzymatically ligated into gene sequences such that the degenerate set of potential EFEMP1 sequences are expressible as individual polypeptides, or alternatively, as a set of larger fusion proteins (e.g., for phage display) containing the set of EFEMP1 sequences therein.

There are many ways by which such libraries of potential EFEMP1 homologs can be generated from a degenerate oligonucleotide sequence. Chemical synthesis of a degenerate gene sequence can be carried out in an automatic DNA synthesizer, and the synthetic genes then ligated into an appropriate expression vector. The purpose of a degenerate set of genes is to provide, in one mixture, all of the sequences encoding the desired set of potential EFEMP1 sequences. The synthesis of degenerate oligonucleotides is well known in the art (see for example, Narang, S A (1983) Tetrahedron 39:3; Itakura et al. (1981) Recombinant DNA, Proc 3rd Cleveland Sympos. Macromolecules, ed. A G Walton, Amsterdam: Elsevier pp 273–289; Itakura et al. (1984) Annu. Rev. Biochem. 53:323; Itakura et al. (1984) Science 198:1056; Ike et al. (1983) Nucleic Acid Res. 11:477. Such techniques have been employed in the directed evolution of other proteins (see, for example, Scott et al. (1990) Science 249:386–390; Roberts et al. (1992) PNAS 89:2429–2433; Devlin et al. (1990) Science 249: 404–406; Cwirla et al. (1990) PNAS 87: 6378–6382; as well as U.S. Pat. Nos. 5,223,409, 5,198,346, and 5,096,815).

Likewise, a library of coding sequence fragments can be provided for an EFEMP1 clone in order to generate a variegated population of EFEMP1 fragments for screening and subsequent selection of bioactive fragments. A variety of techniques are known in the art for generating such libraries, including chemical synthesis. In one embodiment, a library of coding sequence fragments can be generated by (i) treating a double stranded PCR fragment of an EFEMP1 coding sequence with a nuclease under conditions wherein nicking occurs only about once per molecule; (ii) denaturing the double stranded DNA; (iii) renaturing the DNA to form double stranded DNA which can include sense/antisense pairs from different nicked products; (iv) removing single stranded portions from reformed duplexes by treatment with S1 nuclease; and (v) ligating the resulting fragment library into an expression vector. By this exemplary method, an expression library can be derived which codes for N-terminal, C-terminal and internal fragments of various sizes.

A wide range of techniques are known in the art for screening gene products of combinatorial libraries made by point mutations or truncation, and for screening cDNA libraries for gene products having a certain property. Such techniques will be generally adaptable for rapid screening of the gene libraries generated by the combinatorial mutagenesis of EFEMP1 homologs. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Each of the illustrative assays described below are amenable to high through-put analysis as necessary to screen large numbers of degenerate EFEMP1 sequences created by combinatorial mutagenesis techniques. Combinatorial mutagenesis has a potential to generate very large libraries of mutant proteins, e.g., in the order of $10^{26}$ molecules. Combinatorial libraries of this size may be technically challenging to screen even with high throughput screening assays. To overcome this problem, a new technique has been developed recently, recursive ensemble mutagenesis (REM), which allows one to avoid the very high proportion of non-functional proteins in a random library and simply enhances the frequency of functional proteins, thus decreasing the complexity required to achieve a useful sampling of sequence space. REM is an algorithm which enhances the frequency of functional mutants in a library when an appropriate selection or screening method is employed (Arkin and Yourvan, 1992, PNAS USA 89:7811–7815; Yourvan et al., 1992, Parallel Problem Solving from Nature, 2., In Maenner and Manderick, eds., Elsevir Publishing Co., Amsterdam, pp. 401–410; Delgrave et al., 1993, Protein Engineering 6(3):327–331).

The invention also provides for reduction of the EFEMP1 proteins to generate mimetics, e.g., peptide or non-peptide agents, such as small molecules, which are able to disrupt binding of an EFEMP1 polypeptide of the present invention with a molecule, e.g. target peptide. Thus, such mutagenic techniques as described above are also useful to map the determinants of the EFEMP1 proteins which participate in protein-protein interactions involved in, for example, binding of the subject EFEMP1 polypeptide to a target peptide. To illustrate, the critical residues of a subject EFEMP1 polypeptide which are involved in molecular recognition of its receptor can be determined and used to generate EFEMP1 derived peptidomimetics or small molecules which competitively inhibit binding of the authentic EFEMP1 protein with that moiety. By employing, for example, scanning mutagenesis to map the amino acid residues of the subject EFEMP1 proteins which are involved in binding other proteins, peptidomimetic compounds can be generated which mimic those residues of the EFEMP1 protein which facilitate the interaction. Such mimetics may then be used to interfere with the normal function of an EFEMP1 protein. For instance, non-hydrolyzable peptide analogs of such residues can be generated using benzodiazepine (e.g., see Freidinger et al. in Peptides: Chemistry and Biology, G. R. Marshall ed., ESCOM Publisher: Leiden, Netherlands, 1988), azepine (e.g., see Huffman et al. in Peptides: Chemistry and Biology, G. R. Marshall ed., ESCOM Publisher: Leiden, Netherlands, 1988), substituted gamma lactam rings (Garvey et al. in Peptides: Chemistry and Biology, G. R. Marshall ed., ESCOM Publisher: Leiden, Netherlands, 1988), keto-methylene pseudopeptides (Ewenson et al. (1986) J Med Chem 29:295; and Ewenson et al. in Peptides: Structure and Function (Proceedings of the 9th American Peptide Symposium) Pierce Chemical Co. Rockland, Ill., 1985), b-turn dipeptide cores (Nagai et al. (1985) Tetrahedron Lett 26:647; and Sato et al. (1986) J Chem Soc Perkin Trans 1:1231), and b-aminoalcohols (Gordon et al. (1985) Biochem Biophys Res Commun126:419; and Dann et al. (1986) Biochem Biophys Res Commun 134:71).

4.5. Anti-EFEMP1 Antibodies and Uses Therefor

Another aspect of the invention pertains to an antibody specifically reactive with a mammalian EFEMP1 protein, e.g., a wild-type or mutated EFEMP1 protein. For example, by using immunogens derived from an EFEMP1 protein, e.g., based on the cDNA sequences, anti-protein/anti-peptide antisera or monoclonal antibodies can be made by standard protocols (See, for example, Antibodies: A Laboratory Manual ed. by Harlow and Lane (Cold Spring Harbor Press: 1988)). A mammal, such as a mouse, a hamster or rabbit can be immunized with an immunogenic form of the peptide (e.g., a mammalian EFEMP1 polypeptide or an antigenic fragment which is capable of eliciting an antibody response, or a fusion protein as described above). Techniques for conferring immunogenicity on a protein or peptide include conjugation to carriers or other techniques well known in the art. An immunogenic portion of an EFEMP1 protein can be administered in the presence of adjuvant. The progress of immunization can be monitored by detection of antibody titers in plasma or serum. Standard ELISA or other immunoassays can be used with the immunogen as antigen to assess the levels of antibodies. In a preferred embodiment, the subject antibodies are immunospecific for antigenic determinants of an EFEMP1 protein of a mammal, e.g., antigenic determinants of a protein set forth in SEQ ID No: 1 or closely related homologs (e.g.; at least 90% homologous, and more preferably at least 94% homologous).

Following immunization of an animal with an antigenic preparation of an EFEMP1 polypeptide, anti-EFEMP1 antisera can be obtained and, if desired, polyclonal anti-EFEMP1 antibodies isolated from the serum. To produce monoclonal antibodies, antibody-producing cells (lymphocytes) can be harvested from an immunized animal and fused by standard somatic cell fusion procedures with immortalizing cells such as myeloma cells to yield hybridoma cells. Such techniques are well known in the art, and include, for example, the hybridoma technique originally developed by Kohler and Milstein ((1975) *Nature*, 256: 495–497), the human B cell hybridoma technique (Kozbar et al., (1983) *Immunology Today*, 4: 72), and the EBV-hybridoma technique to produce human monoclonal antibodies (Cole et al., (1985) Monoclonal Antibodies and Cancer Therapy, Alan R. Liss, Inc. pp. 77–96). Hybridoma cells can be screened immunochemically for production of antibodies specifically reactive with a mammalian EFEMP1 polypeptide of the present invention and monoclonal antibodies isolated from a culture comprising such hybridoma cells. In one embodiment anti-human EFEMP1 antibodies specifically react with the protein encoded by a nucleic acid having a sequence shown in FIG. 5.

The term antibody as used herein is intended to include fragments thereof which are also specifically reactive with one of the subject mammalian EFEMP1 polypeptides. Antibodies can be fragmented using conventional techniques and the fragments screened for utility in the same manner as described above for whole antibodies. For example, $F(ab)_2$ fragments can be generated by treating antibody with pepsin. The resulting $F(ab)_2$ fragment can be treated to reduce disulfide bridges to produce Fab fragments. The antibody of the present invention is further intended to include bispecific, single-chain, and chimeric and humanized molecules having affinity for an EFEMP1 protein conferred by at least one CDR region of the antibody. In preferred embodiments, the antibody further comprises a label attached thereto and able to be detected, (e.g., the label can be a radioisotope, fluorescent compound, enzyme or enzyme co-factor).

Anti-EFEMP1 antibodies can be used, e.g., to monitor EFEMP1 protein levels in an individual for determining, e.g., whether a subject has a disease or condition associated with an aberrant EFEMP1 protein level, or allowing determination of the efficacy of a given treatment regimen for an individual afflicted with such a disorder. The level of EFEMP1 polypeptides may be measured from cells in bodily fluid, such as in blood samples.

Another application of anti-EFEMP1 antibodies of the present invention is in the immunological screening of cDNA libraries constructed in expression vectors such as λgt11, λgt18–23, λZAP, and λORF8. Messenger libraries of this type, having coding sequences inserted in the correct reading frame and orientation, can produce fusion proteins. For instance, λgt11 will produce fusion proteins whose amino termini consist of β-galactosidase amino acid sequences and whose carboxy termini consist of a foreign polypeptide. Antigenic epitopes of an EFEMP1 protein, e.g., other orthologs of a particular EFEMP1 protein or other paralogs from the same species, can then be detected with antibodies, as, for example, reacting nitrocellulose filters lifted from infected plates with anti-EFEMP1 antibodies. Positive phage detected by this assay can then be isolated from the infected plate. Thus, the presence of EFEMP1 homologs can be detected and cloned from other animals, as can alternate isoforms (including splice variants) from humans.

4.6 Predictive Medicine 4.6.1. MD Causative Mutations

The invention is based, at least in part, on the identification of mutations that cause Macular Degeneration (MD). Because the particular MD mutations may be in linkage disequilibrium with other alleles, the detection of such other alleles can also indicate a predisposition to developing MD in a subject.

4.6.2. Detection of Alleles

Many methods are available for detecting specific alleles at human polymorphic loci. The preferred method for detecting a specific polymorphic allele may depend, in part, upon the molecular nature of the polymorphism. For example, detection of specific alleles may be nucleic acid techniques based on hybridization, size, or sequence, such as restriction fragment length polymorphism (RFLP), nucleic acid sequencing, and allele specific oligonucleotide (ASO) hybridization. In one embodiment, the methods comprise detecting in a sample of DNA obtained from a subject the existence of an allele associated with MD. For example, a nucleic acid composition comprising a nucleic acid probe including a region of nucleotide sequence which is capable of hybridizing to a sense or antisense sequence to an allele associated with MD can be used as follows: the nucleic acid in a sample is rendered accessible for hybridization, the probe is contacted with the nucleic acid of the sample, and the hybridization of the probe to the sample nucleic acid is detected. Such technique can be used to detect alterations or allelic variants at either the genomic or mRNA level as well as to determine mRNA transcript levels, when appropriate.

A preferred detection method is ASO hybridization using probes overlapping an allele associated with MD and has about 5, 10, 20, 25, or 30 nucleotides around the mutation or polymorphic region. In a preferred embodiment of the invention, several probes capable of hybridizing specifically to other allelic variants involved in MD are attached to a solid phase support, e.g., a "chip" (which can hold up to about 250,000 oligonucleotides). Oligonucleotides can be bound to a solid support by a variety of processes, including lithography. Mutation detection analysis using these chips comprising oligonucleotides, also termed "DNA probe arrays" is described e.g., in Cronin et al., *Human Mutation* 7:244, 1996. In one embodiment, a chip comprises all the allelic variants of at least one polymorphic region of a gene. The solid phase support is then contacted with a test nucleic acid and hybridization to the specific probes is detected. Accordingly, the identity of numerous allelic variants of one or more genes can be identified in a simple hybridization experiment.

These techniques may also comprise the step of amplifying the nucleic acid before analysis. Amplification techniques are known to those of skill in the art and include, but are not limited to cloning, polymerase chain reaction (PCR), polymerase chain reaction of specific alleles (ASA), ligase chain reaction (LCR), nested polymerase chain reaction, self sustained sequence replication (Guatelli, J. C. et al., *Proc. Natl. Acad. Sci. USA* 87:1874–78, 1990), transcriptional amplification system (Kwoh, D. Y. et al., *Proc. Natl. Acad. Sci. USA* 86:1173–77, 1989), and Q-Beta Replicase (Lizardi, P. M. et al., *Bio/Technology* 6:1197, 1988).

Amplification products may be assayed in a variety of ways, including size analysis, restriction digestion followed by size analysis, detecting specific tagged oligonucleotide primers in the reaction products, ASO hybridization, allele specific 5' exonuclease detection, sequencing, hybridization, and the like.

PCR based detection means can include multiplex amplification of a plurality of markers simultaneously. For example, it is well known in the art to select PCR primers to generate PCR products that do not overlap in size and can be analyzed simultaneously. Alternatively, it is possible to amplify different markers with primers that have detectable labels that are different and thus can each be differentially detected. Of course, hybridization based detection means allow the differential detection of multiple PCR products in a sample. Other techniques are known in the art to allow multiplex analyses of a plurality of markers.

In a merely illustrative embodiment, the method includes the steps of (i) collecting a sample of cells from a patient, (ii) isolating nucleic acid (e.g., genomic, mRNA or both) from the cells of the sample, (iii) contacting the nucleic acid sample with one or more primers which specifically hybridize to an allele associated with MD, under conditions such that hybridization and amplification of the desired marker occurs, and (iv) detecting the amplification product. These detection schemes are especially useful for the detection of nucleic acid molecules if such molecules are present in very low numbers.

An allele associated with MD can also be identified by alterations in restriction enzyme cleavage patterns through RFLP analysis. For example, sample and control DNA is isolated, amplified (optionally), digested with one or more restriction endonucleases, and fragment length sizes are determined by gel electrophoresis through size fractionization.

In yet another embodiment, any of a variety of sequencing reactions known in the art can be used to directly sequence a polymorphic site having at least one allele associated with MD. Exemplary sequencing reactions include those based on techniques developed by Maxim and Gilbert (*Proc. Natl. Acad. Sci. USA* 74:560, 1977) or Sanger (Sanger et al., *Proc. Nat. Acad. Sci. USA* 74:5463, 1977). It is also contemplated that any of a variety of automated sequencing procedures may be utilized when performing the subject assays (*Biotechniques* 19:448, 1995), including sequencing by mass spectrometry (see, for example PCT publication WO 94/16101; Cohen et al., *Adv. Chromatogr.* 36:127–62,1996; and Griffin et al., *Appl. Biochem. Biotechnol.* 38:147–59, 1993). It will be evident to one skilled in the art that, for certain embodiments, the occurrence of only one, two or three of the nucleic acid bases need be determined in the sequencing reaction. For instance, A-track or the like, e.g., where only one nucleic acid is detected, can be carried out.

In a further embodiment, protection from cleavage agents (such as a nuclease, hydroxylamine or osmium tetroxide and with piperidine) can be used to detect mismatched bases in RNA/RNA or RNA/DNA or DNA/DNA heteroduplexes (Myers et al., *Science* 230:1242, 1985). In general, the art technique of "mismatch cleavage" starts by providing heteroduplexes formed by hybridizing (labelled) RNA or DNA containing the wild-type allele with the sample. The double-stranded duplexes are treated with an agent which cleaves single-stranded regions of the duplex such as which will exist due to base pair mismatches between the control and sample strands. For instance, RNA/DNA duplexes can be treated with RNase and DNA/DNA hybrids treated with S1 nuclease to enzymatically digest the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. (See, for example, Cotton et al., *Proc. Natl. Acad. Sci. USA* 85:4397, 1988; Saleeba et al., *Methods Enzymol.* 217:286–95, 1992) In a preferred embodiment, the control DNA or RNA can have a detectable label.

In still another embodiment, the mismatch cleavage reaction employs one or more proteins that recognize mismatched base pairs in double-stranded DNA (so called "DNA mismatch repair" enzymes). For example, the mutY enzyme of *E. coli* cleaves A at G/A mismatches and the thymidine DNA glycosylase from HeLa cells cleaves T at G/T mismatches (Hsu et al., *Carcinogenesis* 15:1657–62, 1994). According to an exemplary embodiment, an appropriate probe is hybridized to a cDNA or other DNA product from a test cell(s). The duplex is treated with a DNA mismatch repair enzyme, and the cleavage products, if any, can be detected from electrophoresis protocols or the like. (See, for example, U.S. Pat. No. 5,459,039.)

In other embodiments, alterations in electrophoretic mobility will be used to identify an allele associated with MD. For example, single strand conformation polymorphism (SSCP) may be used to detect differences in electrophoretic mobility between mutant and wild type nucleic acids (Orita et al., *Proc. Natl. Acad. Sci. USA* 86:2766, 1989, see also Cotton, *Mutat. Res.* 285:125–44, 1993; and Hayashi, *Genet. Anal. Tech. Appl.* 9:73–79, 1992. Single-stranded DNA fragments of sample and control are denatured and allowed to renature. The secondary structure of single-stranded nucleic acids varies according to sequence, the resulting alteration in electrophoretic mobility enables the detection of even a single base change. The DNA fragments may be labeled or detected with labeled probes, such as primers with a detectable label. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al., *Trends Genet.* 7:5, 1991).

In yet another embodiment, the movement of an allele associated with MD in polyacrylamide gels containing a gradient of denaturant is assayed using denaturing gradient gel electrophoresis (DGGE) (Myers et al., *Nature* 313:495, 1985). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing agent gradient to identify differences in the mobility of control and sample DNA (Rosenbaum and Reissner, *Biophys. Chem.* 265:12753, 1987).

Examples of other techniques for detecting alleles associated with MD include, but are not limited to, selective oligonucleotide hybridization, selective amplification, or selective primer extension. For example, oligonucleotide primers may be prepared in which the known mutation or nucleotide difference (e.g., in allelic variants) is placed centrally and then hybridized to target DNA under conditions which permit hybridization only if a perfect match is found (Saiki et al., *Nature* 324:163, 1986); Saiki et al., *Proc. Natl. Acad. Sci. USA* 86:6230, 1989). Such ASO hybridization techniques may be used to test one mutation or polymorphic region per reaction when oligonucleotides are hybridized to PCR amplified target DNA or a number of different mutations or polymorphic regions when the oligonucleotides are attached to the hybridizing membrane and hybridized with labelled target DNA.

Alternatively, allele specific amplification technology which depends on selective PCR amplification may be used in conjunction with the instant invention. Oligonucleotides used as primers for specific amplification may carry the mutation or polymorphic region of interest in the center of the molecule (so that amplification depends on differential hybridization) (Gibbs et al., *Nucleic Acids Res.* 17:2437–2448, 1989) or at the extreme 3' end of one primer where, under appropriate conditions, mismatch can prevent, or reduce polymerase extension (Prossner, *Tibtech* 11:238, 1993. In addition it may be desirable to introduce a novel restriction site in the region of the mutation to create cleavage-based detection (Gasparini et al., *Mol. Cell Probes* 6:1, 1992). It is anticipated that in certain embodiments amplification may also be performed using Taq ligase for amplification (Barany, *Proc. Natl. Acad. Sci USA* 88:189, 1991). In such cases, ligation will occur only if there is a perfect match at the 3' end of the 5' sequence making it possible to detect the presence of a known mutation at a specific site by looking for the presence or absence of amplification.

In another embodiment, identification of the allelic variant is carried out using an oligonucleotide ligation assay (OLA), as described, e.g., in U.S. Pat. No. 4,998,617 and in Landegren et al., *Science* 241:1077–80, 1988. The OLA protocol uses two oligonucleotides which are designed to be capable of hybridizing to abutting sequences of a single strand of a target. One of the oligonucleotides is linked to a separation marker, e.g,. biotinylated, and the other has a detectable label. If the precise complementary sequence is found in a target molecule, the oligonucleotides will hybridize such that their termini abut, and create a ligation substrate. Ligation then permits the labeled oligonucleotide to be recovered using avidin, or another biotin ligand. Nickerson, D. A. et al. have described a nucleic acid detection assay that combines attributes of PCR and OLA (Nickerson et al., *Proc. Natl. Acad. Sci. USA* 87:8923–27, 1990. In this method, PCR is used to achieve the exponential amplification of target DNA, which is then detected using OLA.

Several techniques based on this OLA method have been developed and can be used to detect alleles associated with MD. For example, U.S. Pat. No. 5,593,826 discloses an OLA using an oligonucleotide having 3'-amino group and a 5'-phosphorylated oligonucleotide to form a conjugate having a phosphoramidate linkage. In another variation of OLA described in Tobe et al., *Nucleic Acids Res.* 24:3728, 1996, OLA combined with PCR permits typing of two alleles in a single microtiter well. By marking each of the allele-specific primers with a unique hapten, i.e. digoxigenin and fluorescein, each OLA reaction can be detected by using hapten specific antibodies that are labeled with different enzyme reporters, alkaline phosphatase or horseradish peroxidase. This system permits the detection of the two alleles using a high throughput format that leads to the production of two different colors.

Several methods have been developed to facilitate analysis of single nucleotide polymorphisms. In one embodiment, the single base polymorphism can be detected by using a specialized exonuclease-resistant nucleotide, as disclosed, e.g., in U.S. Pat. No. 4,656,127 (Mundy et al.). According to the method, a primer complementary to the allelic sequence immediately 3' to the polymorphic site is permitted to hybridize to a target molecule obtained from a particular animal or human. If the polymorphic site on the target molecule contains a nucleotide that is complementary to the particular exonuclease-resistant nucleotide derivative present, then that derivative will be incorporated onto the end of the hybridized primer. Such incorporation renders the primer resistant to exonuclease, and thereby permits its detection. Since the identity of the exonuclease-resistant derivative of the sample is known, a finding that the primer has become resistant to exonucleases reveals that the nucleotide present in the polymorphic site of the target molecule was complementary to that of the nucleotide derivative used in the reaction. This method has the advantage that it does not require the determination of large amounts of extraneous sequence data.

In another embodiment of the invention, a solution-based method is used for determining the identity of the nucleotide of a polymorphic site. French Patent 2,650,840; PCT Appln. No. WO91/02087. As in the Mundy method of U.S. Pat. No. 4,656,127, a primer is employed that is complementary to allelic sequences immediately 3' to a polymorphic site. The method determines the identity of the nucleotide of that site using labeled dideoxynucleotide derivatives, which, if complementary to the nucleotide of the polymorphic site will become incorporated onto the terminus of the primer.

An alternative method, known as Genetic Bit Analysis or GBA™ is described by Goelet et al. in PCT Appln. No. 92/15712. The method of Goelet et al. uses mixtures of labeled terminators and a primer that is complementary to the sequence 3' to a polymorphic site. The labeled terminator that is incorporated is thus determined by, and complementary to, the nucleotide present in the polymorphic site of the target molecule being evaluated. In contrast to the method of Cohen et al., French Patent 2,650,840 and PCT Appln. No. WO91/02087, the method of Goelet et al. is preferably a heterogeneous phase assay, in which the primer or the target molecule is immobilized to a solid phase.

Recently, several primer-guided nucleotide incorporation procedures for assaying polymorphic sites in DNA have been described (Komher et al., *Nucleic Acids Res.* 17:7779–84, 1989; Sokolov, *Nucleic Acids Res.* 18:3671, 1990; Syvanen et al., *Genomics* 8:684–92, 1990; Kuppuswamy et al., *Proc. Natl. Acad. Sci. USA* 88:1143–47, 1991; Prezant et al., *Hum. Mutat.* 1:159–64, 1992; Ugozzoli et al., *GATA* 9:107–12, 1992; Nyren et al., *Anal. Biochem.* 208:171–75, 1993). These methods differ from GBA™ in that they all rely on the incorporation of labeled deoxynucleotides to discriminate between bases at a polymorphic site. In such a format, since the signal is proportional to the number of deoxynucleotides incorporated, polymorphisms that occur in runs of the same nucleotide can result in signals that are proportional to the length of the run (Syvanen, et al., *Amer. J. Hum. Genet.* 52:46–59, 1993).

For mutations that produce premature termination of protein translation, the protein truncation test (PTT) offers an efficient diagnostic approach (Roest. et. al., *Hum. Mol. Genet.* 2:1719–21, 1993; van der Luijt et. al., *Genomics* 20:1–4, 1994). For PTT, RNA is initially isolated from available tissue and reverse-transcribed, and the segment of interest is amplified by PCR. The products of reverse transcription PCR are then used as a template for nested PCR amplification with a primer that contains an RNA polymerase promoter and a sequence for initiating eukaryotic translation. After amplification of the region of interest, the unique motifs incorporated into the primer permit sequential in vitro transcription and translation of the PCR products. Upon sodium dodecyl sulfate-polyacrylamide gel electrophoresis of translation products, the appearance of truncated polypeptides signals the presence of a mutation that causes premature termination of translation. In a variation of this technique, DNA (as opposed to RNA) is used as a PCR template when the target region of interest is derived from a single exon.

In still another method known as Dynamic Allele Specific Hybridization (DASH), a target sequence is amplified by PCR in which one primer is biotinylated. The biotinylated product strand is bound to a streptavidin or avidin coated microtiter plate well, and the non-biotinylated strand is rinsed away with alkali. An oligonucleotide probe, specific for one allele, is hybridized to the target at low temperature. This forms a duplex DNA region that interacts with a double strand-specific intercalating dye. Upon excitation, the dye emits fluorescence proportional to the amount of double stranded DNA (probe-target duplex) present. The sample is then steadily heated while fluorescence is continually monitored. A rapid fall in fluorescence indicates the denaturing (or "melting") temperature of the probe-target duplex. When performed under appropriate buffer and dye conditions, a single-base mismatch between the probe and the target results in a dramatic lowering of melting temperature (Tm) that can be easily detected (Howell, W. M. et al., (1999) *Nature Biotechnology* 17:)87–88.

Any cell type or tissue may be utilized in the diagnostics described herein. In a preferred embodiment the DNA sample is obtained from a bodily fluid obtained by known techniques. Alternatively, nucleic acid tests can be performed on dry samples (e.g. hair or skin).

Diagnostic procedures may also be performed in situ directly upon tissue sections (fixed and/or frozen) of patient tissue obtained from biopsies or resections, such that no nucleic acid purification is necessary. Nucleic acid reagents may be used as probes and/or primers for such in situ procedures (see, for example, Nuovo, PCR in situ Hybridization: Protocols and Applications (Raven Press, NY, 1992)).

In addition to methods which focus primarily on the detection of one nucleic acid sequence, profiles may also be assessed in such detection schemes. Fingerprint profiles may be generated, for example, by utilizing a differential display procedure, Northern analysis and/or RT-PCR.

Another embodiment of the invention is directed to kits. This kit may contain one or more oligonucleotides, including 5' and 3' oligonucleotides that hybridize 5' and 3'to a polymorphic site having as allele associated with MD or detection oligonucleotides that hybridize directly to an allele associate with MD. The kit may also contain one or more oligonucleotides capable of hybridizing near or at other alleles that are in linkage disequilibrium with an MD causing allele (mutation). PCR amplification oligonucleotides should hybridize between 25 and 2500 base pairs apart, preferably between about 100 and about 500 bases apart, in order to produce a PCR product of convenient size for subsequent analysis.

For use in a kit, oligonucleotides may be any of a variety of natural and/or synthetic compositions such as synthetic oligonucleotides, restriction fragments, cDNAs, synthetic peptide nucleic acids (PNAs), and the like. The assay kit and method may also employ oligonucleotides having detectable labels to allow ease of identification in the assays. Examples of labels which may be employed include radio-labels, enzymes, fluorescent compounds, streptavidin, avidin, biotin, magnetic moieties, metal binding moieties, antigen or antibody moieties, and the like. Oligonucleotides useful in kits as well as other aspects of the present invention are selected from,the group consisting of any oligonucleotides that overlap or are contained in SEQ. ID. Nos. 46–74. Particularly preferred primers can be selected from any of SEQ ID NOs 2–43 One of skill in the art can readily determine additional useful oligonucleotide sequences based on the sequences provided herein.

The kit may, optionally, also include DNA sampling means; DNA purification reagents such as Nucleon™ kits, lysis buffers, proteinase solutions and the like; PCR reagents, such as 10×reaction buffers, thermostable polymerase, dNTPs, and the like; and DNA detection means such as appropriate restriction enzymes, allele specific oligonucleotides, degenerate oligonucleotide primers for nested PCR.

4.6.3. Pharmacogenomics

Knowledge of the particular MD associated mutations, alone or in conjunction with information on other genetic defects contributing to MD (the genetic profile of MD) allows a customization of the therapy to the individual's genetic profile, the goal of "pharmacogenomics". Thus, comparison of a subject's particular genetic profile to the genetic profile of MD, permits the selection or design of drugs that are expected to be safe and efficacious for a particular patient or patient population (i.e., a group of patients having the same genetic alteration).

The ability to target populations expected to show the highest clinical benefit, based on genetic profile, can enable: 1) the repositioning of marketed drugs with disappointing market results; 2) the rescue of drug candidates whose clinical development has been discontinued as a result of safety or efficacy limitations, which are patient subgroup-specific; and 3) an accelerated and less costly development for drug candidates and more optimal drug labeling (e.g. since measuring the effect of various doses of an agent on an MD causative mutation is useful for optimizing effective dose).

Cells of a subject may also be obtained before and after administration of a candidate MD therapeutic to detect the level of expression of genes other than EFEMP1, to verify that the therapeutic does not increase or decrease the expression of genes which could be deleterious. This can be done, e.g., by using the method of transcriptional profiling. Thus, mRNA from cells exposed in vivo to a therapeutic and mRNA from the same type of cells that were not exposed to the therapeutic could be reverse transcribed and hybridized to a chip containing DNA from numerous genes, to thereby compare the expression of genes in cells treated and not treated with the therapeutic.

4.7. EFEMP1 Bassed Therapeutics 4.7.1 EFEMP1 Therapeutics

Agents that modulate an EFEMP1 bioactivity should prove useful in treating or preventing a number of EFEMP1 are useful in treating or preventing the development of diseases such as macular degeneration. Such EFEMP1 therapeutics can comprise nucleic acids (e.g. genes, fragments thereof, antisense molecule, proteins (e.g. glycosylated or unglycosylated protein, polypeptide or protein) or other organic or inorganic molecules (e.g. small molecules) that interfere with or compensate for the biochemical events that are causative of MD. The following describes in vitro and in vivo assays for identifying and/or testing candidate therapeutics.

4.7.2. Cell Based and Cell Free Assays for Identifying Therapeutics

In many drug screening programs which test libraries of compounds and natural extracts, high throughput assays are desirable in order to maximize the number of compounds surveyed in a given period of time. Assays which are performed in cell-free systems, such as may be derived with purified or semi-purified proteins, are often preferred as "primary" screens in that they can be generated to permit rapid development and relatively easy detection of an alteration in a molecular target which is mediated by a test compound. Moreover, the effects of cellular toxicity and/or bioavailability of the test compound can be generally ignored in the in vitro system, the assay instead being focused primarily on the effect of the drug on the molecular target as may be manifest in an alteration of binding affinity with upstream or downstream elements.

Accordingly, in an exemplary screening assay of the present invention, the compound of interest is contacted with a protein which may function upstream (including both activators (enhancers) and repressors of its activity) or to proteins and/or nucleic acids (e.g. promoter) which may function downstream of the EFEMP1 polypeptide, whether they are positively or negatively regulated by it. To the mixture of the compound and the upstream or downstream element is then added a composition containing an EFEMP1 polypeptide. Detection and quantification of complexes of EFEMP1 with it's upstream or downstream elements provide a means for determining a compound's efficacy at antagonizing (inhibiting) or agonizing ( potentiating) complex formation between an EFEMP1 protein and an EFEMP1 binding element (e.g. protein or nucleic acid). The efficacy of the compound can be assessed by generating dose response curves from data obtained using various concentrations of the test compound. Moreover, a control assay can also be performed to provide a baseline for comparison. In the control assay, isolated and purified EFEMP1 polypeptide is added to a composition containing the EFEMP1 binding element, and the formation of a complex is quantitated in the absence of the test compound.

Complex formation between the EFEMP1 polypeptide and a binding element may be detected by a variety of techniques. Modulation of the formation of complexes can be quantitated using, for example, detectably labeled proteins such as radiolabeled, fluorescently labeled, or enzymatically labeled EFEMP1 polypeptides, by immunoassay, or by chromatographic detection.

Typically, it will be desirable to immobilize either EFEMP1 protein or its binding protein to facilitate separation of complexes from uncomplexed forms of one or both of the proteins, as well as to accommodate automation of the assay. Binding of EFEMP1 to an upstream or downstream element, in the presence or absence of a candidate agent, can be accomplished in any vessel suitable for containing the reactants. Examples include microtitre plates, test tubes, and micro-centrifuge tubes. In one embodiment, a fusion protein can be provided which adds a domain that allows the protein to be bound to a matrix. For example, glutathione-S-transferase/EFEMP1 (GST/EFEMP1) fusion proteins can be adsorbed onto glutathione sepharose beads (Sigma Chemical, St. Louis, Mo.) or glutathione derivatized microtitre plates, which are then combined with the cell lysates, e.g. an $^{35}$S-labeled, and the test compound, and the mixture incubated under conditions conducive to complex formation, e.g. at physiological conditions for salt and pH, though slightly more stringent conditions may be desired. Following incubation, the beads are washed to remove any unbound label, and the matrix immobilized and radiolabel determined directly (e.g. beads placed in scintillant), or in the supernatant after the complexes are subsequently dissociated. Alternatively, the complexes can be dissociated from the matrix, separated by SDS-PAGE, and the level of EFEMP1-binding protein found in the bead fraction quantitated from the gel using standard electrophoretic techniques.

Other techniques for immobilizing proteins on matrices are also available for use in the subject assay. For instance, an EFEMP1 protein or its cognate binding protein can be immobilized utilizing conjugation of biotin and streptavidin. For instance, biotinylated molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with EFEMP1 or with a protein encoded by a gene that is up- or down-regulated by EFEMP1 can be derivatized to the wells of the plate, and protein trapped in the wells by antibody conjugation. As above, preparations of a binding protein and a test compound are incubated in the protein presenting wells of the plate, and the amount of complex trapped in the well can be quantitated. Exemplary methods for detecting such complexes, in addition to those described above for the GST-immobilized complexes, include immunodetection of complexes using antibodies reactive with the protein binding element, or which are reactive with the EFEMP1 protein; as well as enzyme-linked assays which rely on detecting an enzymatic activity associated with the binding element, either intrinsic or extrinsic activity. In the instance of the latter, the enzyme can be chemically conjugated or provided as a fusion protein with the binding partner. To illustrate, the binding partner can be chemically cross-linked or genetically fused with horseradish peroxidase, and the amount of polypeptide trapped in the complex can be assessed with a chromogenic substrate of the enzyme, e.g. 3,3'-diamino-benzadine terahydrochloride or 4-chloro-l-napthol. Likewise, a fusion protein comprising the polypeptide and glutathione-S-transferase can be provided, and complex formation quantitated by detecting the GST activity using 1-chloro-2,4-dinitrobenzene (Habig et al. (1974) *J Biol Chem* 249:7130).

For processes which rely on immunodetection for quantitating one of the proteins trapped in the complex, antibodies against the protein can be used. Alternatively, the protein to be detected in the complex can be "epitope tagged" in the form of a fusion protein which includes, in addition to the EFEMP1 sequence, a second polypeptide for which antibodies are readily available (e.g. from commercial sources). For instance, the GST fusion proteins described above can also be used for quantification of binding using antibodies against the GST moiety. Other useful epitope tags include myc-epitopes (e.g., see Ellison et al. (1991) J Biol Chem 266:21150–21157) which includes a 10-residue sequence from c-myc, as well as the pFLAG system (International Biotechnologies, Inc.) or the pEZZ-protein A system (Pharamacia, NJ). Transcription factor-DNA binding assays are described in U.S. Pat. No. 5,563,036, which is owned by Tularik and is specifically incorporated by reference herein.

Further, an in vitro assays can be used to detect compounds which can be used for treatment of diseases, such as MD, which are caused or contributed to by defective or deficient EFEMP1 genes or proteins. For example, cells can be engineered to express an EFEMP1 gene (wildtype or mutant) in operative linkage with a reporter gene construct, such as luciferase or chloramphenicol acetyl transferase, or other reporter gene known in the art. Cells can then be contacted with test compounds and the rate or level of EFEMP1 expression can be assayed to identify agonists or antagonists.

Also, a DNA footprinting assay can be used to detect compounds which alter the binding of an EFEMP 1 protein to nucleic acids (see for example, Zhong et al. 1994 *Mol. Cell Biol.* 14:7276). Further, EFEMP1 may be translationally or post-translationally modified by processes such as mRNA editing or protein truncation. Assays to specifically monitor these processes can be performed according to protocols, which are well-known in the art.

In addition to cell-free assays, such as described above, the EFEMP1 proteins provided by the present invention also facilitates the generation of cell-based assays for identifying small molecule agonists/antagonists and the like. For example, cells can be caused to overexpress a recombinant EFEMP1 protein in the presence and absence of a test agent of interest, with the assay scoring for modulation in EFEMP1 responses by the target cell mediated by the test agent. As with the cell-free assays, agents which produce a statistically significant change in EFEMP1 -dependent responses (either inhibition or potentiation) can be identified.

Exemplary cell lines may include retinal pigment epithelial cell lines. Further, the transgenic animals discussed herein may be used to generate cell lines, containing one or more cell types involved in MD, that can be used as cell culture models for this disorder. While primary cultures may be utilized, the generation of continuous cell lines is preferred. For examples of techniques which may be used to derive a continuous cell line from the transgenic animals, see Small et al., 1985, Mol. Cell Biol. 5:642–648.

For example, the effect of a test compound on a variety of end points could be tested. Similarly, epithelial cells can be treated with test compounds or transfected with genetically engineered EFEMP1 genes. Monitoring the influence of compounds on cells may be applied not only in basic drug screening, but also in clinical trials. In such clinical trials, the expression of a panel of genes may be used as a "read out" of a particular drug's therapeutic effect.

In yet another aspect of the invention, the subject EFEMP1 polypeptides can be used in a "two hybrid" assay (see, for example, U.S. Pat. No. 5,283,317; Zervos et al. (1993) Cell 72:223–232; Madura et al. (1993) J Biol Chem 268:12046–12054; Bartel et al. (1993) Biotechniques 14:920–924; Iwabuchi et al. (1993) Oncogene 8:1693–1696; and Brent WO94/10300), for isolating coding sequences for other cellular proteins which bind to or interact with an EFEMP1(e.g., EFEMP1 binding proteins" or "EFEMP1 bp").

Briefly, the two hybrid assay relies on reconstituting in vivo a functional transcriptional activator protein from two separate fusion proteins. In particular, the method makes use of chimeric genes which express hybrid proteins. To illustrate, a first hybrid gene comprises the coding sequence for a DNA-binding domain of a transcriptional activator fused in frame to the coding sequence for an EFEMP1 polypeptide. The second hybrid protein encodes a transcriptional activation domain fused in frame to a sample gene from a cDNA library. If the bait and sample hybrid proteins are able to interact, e.g., form an EFEMP1 dependent complex, they bring into close proximity the two domains of the transcriptional activator. This proximity is sufficient to cause transcription of a reporter gene which is operably linked to a transcriptional regulatory site responsive to the transcriptional activator, and expression of the reporter gene can be detected and used to score for the interaction of the EFEMP1 and sample proteins.

4.7.3 Transgenic Animals for Identifying Therapeutics

Transgenic animals can also be made to identify therapeutics that modulate an EFEMP1 bioactivity, to confirm the safety and efficacy of a candidate therapeutic or to study drusen formation. Transgenic animals of the invention can include non-human animals containing a mutated EFEMP1 gene under the control of an appropriate homologous or heterologous promoter.

Methods for obtaining transgenic non-human animals are well known in the art. In preferred embodiments, the expression of the mutation is restricted to specific subsets of cells, tissues or developmental stages utilizing, for example, cis-acting sequences that control expression in the desired pattern. In the present invention, such mosaic expression can be essential for many forms of lineage analysis and can additionally provide a means to assess the effects of, for example, expression level which might grossly alter development in small patches of tissue within an otherwise normal embryo. Toward this end, tissue-specific regulatory sequences and conditional regulatory sequences can be used to control expression of the mutation in certain spatial patterns. Moreover, temporal patterns of expression can be provided by, for example, conditional recombination systems or prokaryotic transcriptional regulatory sequences. Genetic techniques, which allow for the expression of the mutation can be regulated via site-specific genetic manipulation in vivo, are known to those skilled in the art.

The transgenic animals of the present invention all include within a plurality of their cells a mutant EFEMP1 transgene of the present invention, which transgene alters the phenotype of the "host cell". In an illustrative embodiment, either the cre/loxP recombinase system of bacteriophage P1 (Lakso et al. (1992) PNAS 89:6232–6236; Orban et al. (1992) PNAS 89:6861–6865) or the FLP recombinase system of Saccharomyces cerevisiae (O'Gorman et al. (1991) Science 251:1351–1355; PCT publication WO 92/15694) can be used to generate in vivo site-specific genetic recombination systems. Cre recombinase catalyzes the site-specific recombination of an intervening target sequence located between loxP sequences. loxP sequences are 34 base pair nucleotide repeat sequences to which the Cre recombinase binds and are required for Cre recombinase mediated genetic recombination. The orientation of loxP sequences determines whether the intervening target sequence is excised or inverted when Cre recombinase is present (Abremski et al. (1984) J. Biol. Chem. 259:1509–1514); catalyzing the excision of the target sequence when the loxP sequences are oriented as direct repeats and catalyzes inversion of the target sequence when loxP sequences are oriented as inverted repeats.

Accordingly, genetic recombination of the target sequence is dependent on expression of the Cre recombinase. Expression of the recombinase can be regulated by promoter elements which are subject to regulatory control, e.g., tissue-specific, developmental stage-specific, inducible or repressible by externally added agents. This regulated control will result in genetic recombination of the target sequence only in cells where recombinase expression is mediated by the promoter element. Thus, the activation of expression of a mutation containing transgene can be regulated via control of recombinase expression.

Use of the cre/loxP recombinase system to regulate expression of a mutation containing transgene requires the construction of a transgenic animal containing transgenes encoding both the Cre recombinase and the subject protein. Animals containing both the Cre recombinase and the mutation transgene can be provided through the construction of "double" transgenic animals. A convenient method for providing such animals is to mate two transgenic animals each containing a transgene.

Similar conditional transgenes can be provided using prokaryotic promoter sequences which require prokaryotic proteins to be simultaneous expressed in order to facilitate expression of the transgene. Exemplary promoters and the corresponding trans-activating prokaryotic proteins are given in U.S. Pat. No. 4,833,080.

Moreover, expression of the conditional transgenes can be induced by gene therapy-like methods wherein a gene encoding the transactivating protein, e.g. a recombinase or a prokaryotic protein, is delivered to the tissue and caused to be expressed, such as in a cell-type specific manner. By this method, the transgene could remain silent into adulthood until "turned on" by the introduction of the transactivator.

In an exemplary embodiment, the "transgenic non-human animals" of the invention are produced by introducing transgenes into the germline of the non-human animal. Embryonal target cells at various developmental stages can be used to introduce transgenes. Different methods are used depending on the stage of development of the embryonal target cell. The specific line(s) of any animal used to practice this invention are selected for general good health, good embryo yields, good pronuclear visibility in the embryo, and good reproductive fitness. In addition, the haplotype is a significant factor. For example, when transgenic mice are to be produced, strains such as C57BL/6 or FVB lines are often used (Jackson Laboratory, Bar Harbor, Me.). Preferred strains are those with $H-2^b$, $H-2^d$ or H-2q haplotypes such as C57BL/6 or DBA/1. The line(s) used to practice this invention may themselves be transgenics, and/or may be knockouts (i.e., obtained from animals which have one or more genes partially or completely suppressed). In one embodiment, the transgene construct is introduced into a single stage embryo. The zygote is the best target for microinjection. In the mouse, the male pronucleus reaches the size of approximately 20 micrometers in diameter which allows reproducible injection of 1–2 pl of DNA solution. The use of zygotes as a target for gene transfer has a major advantage in that in most cases the injected DNA will be incorporated into the host gene before the first cleavage (Brinster et al. (1985) *PNAS* 82:4438–4442). As a consequence, all cells of the transgenic animal will carry the incorporated transgene. This will in general also be reflected in the efficient transmission of the transgene to offspring of the founder since 50% of the germ cells will harbor the transgene.

Normally, fertilized embryos are incubated in suitable media until the pronuclei appear. At about this time, the nucleotide sequence comprising the transgene is introduced into the female or male pronucleus as described below. In some species such as mice, the male pronucleus is preferred. It is most preferred that the exogenous genetic material be added to the male DNA complement of the zygote prior to its being processed by the ovum nucleus or the zygote female pronucleus. It is thought that the ovum nucleus or female pronucleus release molecules which affect the male DNA complement, perhaps by replacing the protamines of the male DNA with histones, thereby facilitating the combination of the female and male DNA complements to form the diploid zygote.

Thus, it is preferred that the exogenous genetic material be added to the male complement of DNA or any other complement of DNA prior to its being affected by the female pronucleus. For example, the exogenous genetic material is added to the early male pronucleus, as soon as possible after the formation of the male pronucleus, which is when the male and female pronuclei are well separated and both are located close to the cell membrane. Alternatively, the exogenous genetic material could be added to the nucleus of the sperm after it has been induced to undergo decondensation. Sperm containing the exogenous genetic material can then be added to the ovum or the decondensed sperm could be added to the ovum with the transgene constructs being added as soon as possible thereafter.

Introduction of the transgene nucleotide sequence into the embryo may be accomplished by any means known in the art such as, for example, microinjection, electroporation, or lipofection. Following introduction of the transgene nucleotide sequence into the embryo, the embryo may be incubated in vitro for varying amounts of time, or reimplanted into the surrogate host, or both. In vitro incubation to maturity is within the scope of this invention. One common method in to incubate the embryos in vitro for about 1–7 days, depending on the species, and then reimplant them into the surrogate host.

For the purposes of this invention a zygote is essentially the formation of a diploid cell which is capable of developing into a complete organism. Generally, the zygote will be comprised of an egg containing a nucleus formed, either naturally or artificially, by the fusion of two haploid nuclei from a gamete or gametes. Thus, the gamete nuclei must be ones which are naturally compatible, i.e., ones which result in a viable zygote capable of undergoing differentiation and developing into a functioning organism. Generally, a euploid zygote is preferred. If an aneuploid zygote is obtained, then the number of chromosomes should not vary by more than one with respect to the euploid number of the organism from which either gamete originated.

In addition to similar biological considerations, physical ones also govern the amount (e.g., volume) of exogenous genetic material which can be added to the nucleus of the zygote or to the genetic material which forms a part of the zygote nucleus. If no genetic material is removed, then the amount of exogenous genetic material which can be added is limited by the amount which will be absorbed without being physically disruptive. Generally, the volume of exogenous genetic material inserted will not exceed about 10 picoliters. The physical effects of addition must not be so great as to physically destroy the viability of the zygote. The biological limit of the number and variety of DNA sequences will vary depending upon the particular zygote and functions of the exogenous genetic material and will be readily apparent to one skilled in the art, because the genetic material, including the exogenous genetic material, of the resulting zygote must be biologically capable of initiating and maintaining the differentiation and development of the zygote into a functional organism.

The number of copies of the transgene constructs which are added to the zygote is dependent upon the total amount of exogenous genetic material added and will be the amount which enables the genetic transformation to occur. Theoretically only one copy is required; however, generally, numerous copies are utilized, for example, 1,000–20,000 copies of the transgene construct, in order to insure that one copy is functional. As regards the present invention, there will often be an advantage to having more than one functioning copy of each of the inserted exogenous DNA sequences to enhance the phenotypic expression of the exogenous DNA sequences.

Any technique which allows for the addition of the exogenous genetic material into nucleic genetic material can be utilized so long as it is not destructive to the cell, nuclear membrane or other existing cellular or genetic structures. The exogenous genetic material is preferentially inserted into the nucleic genetic material by microinjection. Microinjection of cells and cellular structures is known and is used in the art.

Reimplantation is accomplished using standard methods. Usually, the surrogate host is anesthetized, and the embryos are inserted into the oviduct. The number of embryos implanted into a particular host will vary by species, but will usually be comparable to the number of off spring the species naturally produces.

Transgenic offspring of the surrogate host may be screened for the presence and/or expression of the transgene by any suitable method. Screening is often accomplished by Southern blot or Northern blot analysis, using a probe that is complementary to at least a portion of the transgene. Western blot analysis using an antibody against the protein encoded by the transgene may be employed as an alternative or additional method for screening for the presence of the transgene product. Typically, DNA is prepared from tail tissue and analyzed by Southern analysis or PCR for the transgene. Alternatively, the tissues or cells believed to express the transgene at the highest levels are tested for the presence and expression of the transgene using Southern analysis or PCR, although any tissues or cell types may be used for this analysis.

Alternative or additional methods for evaluating the presence of the transgene include, without limitation, suitable biochemical assays such as enzyme and/or immunological assays, histological stains for particular marker or enzyme activities, flow cytometric analysis, and the like. Analysis of the blood may also be useful to detect the presence of the transgene product in the blood, as well as to evaluate the effect of the transgene on the levels of various types of blood cells and other blood constituents.

Progeny of the transgenic animals may be obtained by mating the transgenic animal with a suitable partner, or by in vitro fertilization of eggs and/or sperm obtained from the transgenic animal. Where mating with a partner is to be performed, the partner may or may not be transgenic and/or a knockout; where it is transgenic, it may contain the same or a different transgene, or both. Alternatively, the partner may be a parental line. Where in vitro fertilization is used, the fertilized embryo may be implanted into a surrogate host or incubated in vitro, or both. Using either method, the progeny may be evaluated for the presence of the transgene using methods described above, or other appropriate methods.

The transgenic animals produced in accordance with the present invention will include exogenous genetic material. Further, in such embodiments the sequence will be attached to a transcriptional control element, e.g., a promoter, which preferably allows the expression of the transgene product in a specific type of cell.

Retroviral infection can also be used to introduce the transgene into a non-human animal. The developing non-human embryo can be cultured in vitro to the blastocyst stage. During this time, the blastomeres can be targets for retroviral infection (Jaenich, R. (1976) *PNAS* 73:1260–1264). Efficient infection of the blastomeres is obtained by enzymatic treatment to remove the zona pellucida (*Manipulating the Mouse Embryo,* Hogan eds. (Cold Spring Harbor Laboratory Press, Cold Spring Harbor, 1986). The viral vector system used to introduce the transgene is typically a replication-defective retrovirus carrying the transgene (Jahner et al. (1985) *PNAS* 82:6927–6931; Van der Putten et al. (1985) *PNAS* 82:6148–6152). Transfection is easily and efficiently obtained by culturing the blastomeres on a monolayer of virus-producing cells (Van der Putten, supra; Stewart et al. (1987) *EMBO J.* 6:383–388). Alternatively, infection can be performed at a later stage. Virus or virus-producing cells can be injected into the blastocoele (Jahner et al. (1982) *Nature* 298:623–628). Most of the founders will be mosaic for the transgene since incorporation occurs only in a subset of the cells which formed the transgenic non-human animal. Further, the founder may contain various retroviral insertions of the transgene at different positions in the genome which generally will segregate in the offspring. In addition, it is also possible to introduce transgenes into the germ line by intrauterine retroviral infection of the midgestation embryo (Jahner et al. (1982) supra).

A third type of target cell for transgene introduction is the embryonal stem cell (ES). ES cells are obtained from pre-implantation embryos cultured in vitro and fused with embryos (Evans et al. (1981) *Nature* 292:154–156; Bradley et al. (1984) *Nature* 309:255–258; Gossler et al. (1986) *PNAS* 83: 9065–9069; and Robertson et al. (1986) *Nature* 322:445–448). Transgenes can be efficiently introduced into the ES cells by DNA transfection or by retrovirus-mediated transduction. Such transformed ES cells can thereafter be combined with blastocysts from a non-human animal. The ES cells thereafter colonize the embryo and contribute to the germ line of the resulting chimeric animal. For review see Jaenisch, R. (1988) *Science* 240:1468–1474.

4.8 Methods of Treatment 4.8.1. Effective Dose

Toxicity and therapeutic efficacy of such compounds identified as described above can be determined by standard pharmaceutical procedures in cell cultures or experimental animals, e.g., for determining The $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects may be used, care should be taken to design a delivery system that targets such compounds to the site of affected tissues in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

4.8.2. Formulation and Use

Pharmaceutical compositions for use in accordance with the present invention may be formulated in a conventional manner using one or more physiologically acceptable carriers or excipients. Thus, the compounds and their physiologically acceptable salts and solvates may be formulated for administration by, for example, injection, inhalation or insufflation (either through the mouth or the nose) or oral, buccal, parenteral or rectal administration.

For such therapy, the compounds of the invention can be formulated for a variety of loads of administration, including systemic and topical or localized administration. Techniques and formulations generally may be found in Remmington's Pharmaceutical Sciences, Meade Publishing Co., Easton, Pa. For parenteral administration, injection is preferred, including intramuscular, intravenous, intraperitoneal, and subcutaneous. For injection, the compounds of the invention can be formulated in liquid solutions, preferably in physiologically compatible buffers such as Hank's solution or Ringer's solution. In addition, the compounds may be formulated in solid form and redissolved or suspended immediately prior to use. Lyophilized forms are also included.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., ationd oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound. For buccal administration the compositions may take the form of tablets or lozenges formulated in conventional manner. For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt. Other suitable delivery systems include microspheres which offer the possibility of local noninvasive delivery of drugs over an extended period of time. This technology utilizes microspheres of precapillary size which can be injected via a coronary catheter into any selected part of the e.g. heart or other organs without causing inflammation or ischemia. The administered therapeutic is slowly released from these microspheres and taken up by surrounding tissue cells (e.g. endothelial cells).

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration bile salts and fusidic acid derivatives. In addition, detergents may be used to facilitate permeation. Transmucosal administration may be through nasal sprays or using suppositories. For topical administration, the oligomers of the invention are formulated into ointments, salves, gels, or creams as generally known in the art. A wash solution can be used locally to treat an injury or inflammation to accelerate healing.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

The present invention is further illustrated by the following examples which should not be construed as limiting in any way. The contents of all cited references (including literature references, issued patents, published patent applications as cited throughout this application) are hereby expressly incorporated by reference.

The practice of the present invention will employ, unless otherwise indicated, conventional techniques that are within the skill of the art. Such techniques are explained fully in the literature. See, for example, Molecular Cloning A Laboratory Manual, (2nd ed., Sambrook, Fritsch and Maniatis, eds., Cold Spring Harbor Laboratory Press: 1989); DNA Cloning, Volumes I and II (D. N. Glover ed., 1985); Oligonucleotide Synthesis (M. J. Gait ed., 1984)

EXAMPLE 1

Methods and Materials

DNA isolation. A total of 1163 individuals were studied: 166 individuals affected with either ML or DHRD, 26 unaffected spouses of the ML or DHRD families, 494 AMD patients, and 477 control patients. Of the 494 AMD patients, 318 were ascertained in Iowa, 87 elsewhere in the US, 25 in Australia, and 64 in Switzerland. The control samples were obtained from unrelated individuals who were not known to have macular degeneration. The purpose of these samples was to allow an estimation of the general population frequency of any sequence changes observed in the ML/DHRD and AMD groups. Of the control individuals, 104 were ascertained in Iowa, 100 in Australia, 187 in Switzerland, and 86 elsewhere in the US. DNA was extracted from venous blood using a previously described protocol[70]. YAC, BAC, and plasmid DNA was isolated using a previously described protocol[71].

Marker typing. Short Tandem Repeat Polymorphisms (STRPs) were analyzed with PCR amplification and gel electrophoresis as previously described[71]. Six of these STRPs as well as four intragenic EFEMP1 polymorphisms have not been previously reported (see Table 1). Following electrophoresis, the gels were stained with silver nitrate. STS content analysis was performed as previously described[71] and used it to deduce the minimum tiling path of the 2p Malattia Leventinese interval.

YAC and BAC identification and subcloning. YACs were initially identified from the critical region by searching a database at the Whitehead Institute/MIT Genome Center with STSs known to lie in the interval. Additional YACS and BACs were then identified with PCR-based screening of pooled libraries (Research Genetics) with various STSs from the interval. BAC DNA was subcloned as previously described[71].

Sequencing of plasmids and PCR products. PCR was performed for sequencing in a 30 $\mu$l reaction and the products were purified with a Concert Rapid PCR purification kit (Gibco-BRL). 500 ng of plasmid DNA or 3.0 $\mu$l of PCR product was used as template for a sequencing reaction as previously described[71].

Gene characterization. The genomic organization of EFEMP1 was determined with long range and vectorette PCR using the Expand™ Long Template PCR system (Boehringer Mannheim) and a vectorette cassette (Genosys). The PCR products were sized on 1–2% agarose gels with a 100 bp ladder (Gibco/BRL). These PCR products were sequenced and the result compared to published cDNA and exon-intron junction sequence[62,72] to confirm exon-intron borders. This new intronic sequence was used to design primers for SSCP and DNA sequencing of the coding regions using the Primer 3 program (http://www-genome.wi.mit.edu/genome_Software/other/primer3.html).

RNA isolation, blot analysis and RT-PCR A mouse poly (A) mRNA Northern blot was prepared with RNA from freshly dissected adult tissues. This blot was hybridized using a previously described protocol[73] with a 920 bp gel purified insert of the murine EFEMP1 cDNA plasmid (I.M.A.G.E. Consortium Clone ID 1480170, Research Genetics) corresponding to the 3' region of the gene. Human donor eyes were obtained from the Iowa Lions Eye Bank (Iowa City, Iowa) within 4 hours of death. Six-mm trephine punches of RPE were removed and total RNA was isolated using the RNeasy kit (Qiagen). cDNA was synhesized from this RNA with random primers and the cDNA was used in PCR analyses. After 20–35 cycles of PCR, these reaction mixtures were analyzed with agarose gel electrophoresis.

Mutation detection and confirmation. Mutation screening was performed using single strand polymorphism (SSCP) analysis and direct sequencing of PCR products as previously described.[71] The primer sequences used for this screening are given in Table I.

Results and Discussion

Previously, 5 families with the ML phenotype with a total of 56 affected members were investigated. To narrow the genetic interval containing the ML/DHRD gene 28 additional families (75 patients) affected with either ML or DHRD were ascertained from the United States and Switzerland. These families were genotyped with 19 STRP markers in the disease interval but did not observe any recombination events that would narrow the disease interval more than that reported by Gregory, et al.[48] (FIG. 2). However, haplotypic analysis of 23 Swiss families that were likely (for geographic reasons) to share a common ancestor did reveal a narrower interval: between D2S2352 and D2S378 (FIG. 2). Five Australian families were later studied, including one with a clearly affected member who was recombinant telomeric to 293JI2CA, which further narrowed the interval to the segment between 293J12CA and D2S378 (FIG. 2). Markers from this interval were then used to screen libraries of yeast and bacterial artificial chromosomes, and contigs were assembled (FIG. 2) for verification of the genetic map as well as for evaluation of candidate genes and expressed sequence tags (ESTs). In an attempt to identify additional informative polymorphisms, twelve ESTs were screened and six STSs for polymorphisms in a single amplimer in ML, DHRD and AMD patients. In addition, six genes were screened (EFEMP1, beta-fodrin, ubiquitin, WI-6613, WI-22280, and WI-1332) for coding sequence mutations. Only one novel sequence variation was identified during this phase of the project: a single base pair change in the 3' UTR of WI-6613 that was present in all Swiss families but absent from American ML families.

EFEMP1, beta-fodrin, and WI-6613 were then screened more comprehensively for mutations, since they were each present in retinal cDNA libraries and mapped within the narrowest genetic interval. The genomic structures and intronic sequences of these genes were then determined and their coding regions evaluated for mutations by both SSCP analysis and direct DNA sequencing. Beta-fodrin and WI-6613 were each approximately 70% screened without detecting any amino-acid-altering sequence variations when a potential disease-causing variation in EFEMP1 was detected. This C to T transition (Arg345Trp—FIG. 3) was initially observed in 5 families with ML (2 from the US, 2 from Switzerland, and 1 from Australia). The potential involvement of this variation in ML, DHRD, and AMD was then assessed by SSCP screening of all 162 affected patients in the 37 families available at that time, as well as 477 control individuals and 494 unrelated patients affected with AMD. Of the 162 patients initially thought to be affected with ML or DHRD, 161 were found to harbor an SSCP shift in exon 10 of EFEMP1. None of the AMD or control individuals exhibited this shift. Sequence analysis of one patient exhibiting an SSCP shift from each of the 37 families revealed all to harbor the Arg345Trp mutation. The retinal photographs of the two "affected" members of the single family that was discordant for the Arg345Trp change was then reexamined and it was discovered that the individual with the mutation had the characteristic ML phenotype (and the shared Swiss haplotype) while the individual lacking the mutation had a phenotype more typical of common AMD (and failed to share alleles with the Swiss haplotype). Of the 161 ML/DHRD patients harboring the Arg345Trp mutation, 160 carried it in the heterozygous state. One individual was homozygous for this change (FIG. 3) and had a retinal phenotype that was neither more nor less severe than heterozygotes of similar age.

STS content analysis from additional BACs allowed a revision of the marker order such that all 25 Swiss families shared a four marker haplotype that included the Arg345Trp variant. This "final Swiss interval" (FIG. 2) completely excluded beta-fodrin and WI-6613, leaving EFEMP1 as the sole occupant of the critical interval among the group of 12 ESTs and six genes originally considered as candidates.

The entire EFEMP1 coding sequence was then screened by SSCP in 494 AMD patients and 477 control individuals. Three additional EFEMP1 coding sequence variations were detected (Thr181 Thr, ACG-ACA; Ile220Phe, ATC-TTC; and Ser456Ser, TCA-TCG), each present in a single control individual. The entire coding sequence of EFEMP1 was then sequenced in both directions in four individuals: 2 probands with ML (one from Switzerland and one from the United States), one proband with DHRD (from Australia), and a general population control. No additional coding sequence variations were detected.

To investigate the possibility that the original DHRD family harbored a different mutation in the EFEMP1 gene, samples from two nuclear families (one from Northern Ireland and one from England) with genealogical evidence for a relationship with Doyne's original family were studied.[60] Affected individuals from both of these families were found to harbor the Arg345Trp variation.

In an attempt to identify haplotypic recombinants within EFEMP1, a 7.5 kb of intronic sequence was screened for polymorphisms with SSCP. Four intragenic two-allele polymorphisms were identified (see methods) and all 39 families were found to carry the most common allele of each in phase with the Arg345Trp variant.

Although retinal expression of EFEMP1 can be inferred from its presence in retinal cDNA libraries, FIG. 4a, a northern blot of RNA from tissues from adult mice, revealed EFEMP1 to be abundantly expressed in the eye and the lung, and moderately expressed in the brain, heart, spleen, and kidney. An RT-PCR on RNA extracted from isolated retinal pigment epithelial (RPE) cells, a preparation of RPE and choroid, and isolated neurosensory retina (all obtained from human donors) revealed EFEMP1 to be expressed in all of these tissues (FIG. 4b).

The absence of de novo Arg345Trp mutations in the 39 families studied, and the complete sharing of alleles of four intragenic EFEMP1 polymorphisms among these families suggest that the Arg345Trp mutation occurred only once, in a common ancestor of every affected patient in this study. Despite the extensive patient resources available, we were unable to demonstrate that the ancestrally shared interval is entirely contained within the EFEMP1 gene and thus the possibility of a disease-causing mutation in an adjacent gene can not be completely excluded. However, the striking linkage disequilibrium between the disease phenotype and the Arg345Trp variant (absent from over 1900 alleles of non-ML/DHRD individuals) and the high degree of conservation of the EFEMP1 gene (Arg345Trp is the only non-conservative amino acid changing variant observed in the 1163 individuals in this study and alters a codon that is conserved among human, mouse and rat) provide strong evidence that Arg345Trp is disease-causing. Moreover, EFEMP1 is a plausible candidate gene. It is expressed in the tissues closest to the site of drusen formation (RPE and retina) and encodes a protein that is homologous to a family of extracellular matrix glycoproteins known as fibulins[61]. EFEMP1 was originally isolated as a cDNA sequence (then known as S1-5) that was relatively over-expressed in human fibroblasts obtained from a patient with Werner syndrome, a genetic disease characterized by accelerated aging[62]. Finally, the Arg345Trp mutation alters the last EGF domain of the EFEMP1 gene product. It is similar to a number of fibrillin mutations that cause Marfan syndrome[63,64].

TABLE 1

Primer sequences
EFEMP1 gene assay

| | | FORWARD | REVERSE |
|---|---|---|---|
| EXON 3 | | 5' GTTTTGTTACTTTCCCCGCA 3' (SEQ ID NO:2) | 5' ACTGGCAGGGGTGTGTAAAG 3' (SEQ ID NO:3) |
| EXON 4 | | 5' CCAATTAACTGTCTCCTGGC 3' (SEQ ID NO:4) | 5' AAGGCAATGATCACATGGAAG 3' (SEQ ID NO:5) |
| EXON 5A | | 5' CATGTTTGATTTTTCCCTCTTAGAA 3' (SEQ ID NO:6) | 5' ATGCTGCTGGCAGCTACAACC 3' (SEQ ID NO:7) |
| EXON 5B | | 5' AACCTCAGGGGCAACCAC 3' (SEQ ID NO:8) | 5' TTCAATGGTTAGGAAAAGAAGTTATTC 3' (SEQ ID NO:9) |
| EXON 6 | | 5' TGACAATTCTTTCTGTGTTGCAT 3' (SEQ ID NO:10) | 5' CTCAAGACAGGACCGTGCTC 3' (SEQ ID NO:11) |
| EXON 7 | | 5' TTCTCTTTGTGTGTGTGCCTG 3' (SEQ ID NO:12) | 5' TGGGGTTTCCTTTTGTGAAG 3' (SEQ ID NO:13) |
| EXON 8 | | 5' CAAAAGAGTAAGGATATGTTTAAAGTC 3' (SEQ ID NO:14) | 5' GGACTTTATTCCATACTATCTGGG 3' (SEQ ID NO:15) |
| EXON 9 | | 5' TGGTGCACAAACTTTTCAACTC 3' (SEQ ID NO:16) | 5' TCCTCTTGTCTCTTCCTGGC 3' (SEQ ID NO:17) |
| EXON 10 | | 5' CTTGCAAACAGAATCTGCCA 3' (SEQ ID NO:18) | 5' TCCTCACTTTCAAAAGTTCTGATTT 3' (SEQ ID NO:19) |
| EXON 11A | | 5' ACCAAGCCAAACTGCTGAAT 3' (SEQ ID NO:20) | 5' AAAAGTATTGATGGTGTTGGCA 3' (SEQ ID NO:21) |
| EXON 11B | | 5' TGCCATCAGACATCTTCCAG 3' (SEQ ID NO:22) | 5' AATGTTTGCTTTCCTTCCACA 3' (SEQ ID NO:23) |
| EXON 12 | | 5' GCATAGAAACTCCAATCCAAGAA 3' (SEQ ID NO:24) | 5' TGCCTGTGGTTGACTCTTAGAA 3' (SEQ ID NO:25) |
| Novel Repeats | | | |
| 293J12CA | | 5' GGAACAAGCAGGACCTTTCA 3' (SEQ ID NO:26) | 5' TGTTATATCCTATTTGAGCT 3' (SEQ ID NO:27) |
| 322A4AAAT | | 5' ATCCTAGCAAAACATAAGAGT 3' (SEQ ID NO:28) | 5' CTTACATTCCTGTGGACTTGA 3' (SEQ ID NO:29) |
| 133O18CA | | 5' CGGGGATCTTTTTCATGATG 3' (SEQ ID NO:30) | 5' GGGGCAAGGCAAGAGTAAG 3' (SEQ ID NO:31) |
| 133O18AAAT | | 5' CTGCAGTGAGCTGCGATTAT 3' (SEQ ID NO:32) | 5' TTTTGCTTTGGGAATTAGCAG 3' (SEQ ID NO:33) |
| 340O18CA | | 5' GGAGGTTGCAGTGAGCTG 3' (SEQ ID NO:34) | 5' TTGAATTGTCGTGAATCTTGTT 3' (SEQ ID NO:35) |

TABLE 1-continued

Primer sequences
EFEMP1 gene assay

| | FORWARD | REVERSE |
|---|---|---|
| 202J12GGAA | 5' TACCACTGCACTGAAGCCTG 3'<br>(SEQ ID NO:36) | 5' AAATCTTCTGCAAAAACAAAAGTG 3'<br>(SEQ ID NO:37) |
| Intragenic<br>Polymorphisms | | |
| Intron 4 | 5' CCAATTAACTGTCTCCTGGC 3'<br>(SEQ ID NO:38) | 5' TTTGTGCACCACTACTTTGGA 3'<br>(SEQ ID NO:39) |
| Intron 8 | 5' AAATGTGCCCAAGTCACACA 3'<br>(SEQ ID NO:40) | 5' TTTGAAACTGGACCCAAGG 3'<br>(SEQ ID NO:41) |
| Intron 9 | 5' AGCATAAGCTCAATATGGGAGT 3'<br>(SEQ ID NO:42) | 5' TGGCAGTGTTACCAAGAGGA 3'<br>(SEQ ID NO:43) |
| Intron 11 | 5' CAACACCATCAATACTTTTCGG 3'<br>(SEQ ID NO:44) | 5' AAGGCAATGATCACATGGAAG 3'<br>(SEQ ID NO:45) |

REFERENCES

1) Best F. Uber eine hereditare maculaaffektion: Bietrage zur vererbungslehre. *Z Augenheilkd.* (1905); Vol. 13: pp. 199–212.
2) Sorsby A, Joll Mason M E, Gardener N. A fundus dystrophy with unusual features. *Br J. Opthalmol.* (1949); Vol. 33: pp. 67–97.
3) Stargardt K. Ueber familiare, progressive degeneration in der makulagegend des auges. *Albrecht Von Graefes Arch Klin Exp Opthalmol.* (1909); Vol. 71, pp. 534–550.
4) Ferrell R E, Mintz-Hittner H., Antoszyk J H. Linkage of atypical vitelliform macular dystrophy (VDM-1) to the soluble glutamate pyruvate transaminase (GPT1) locus. *Am J. Hum Genet.* (1983); Vol. 35; pp 78–84.
5) Jacobson D M, Thompson H S, Bartley J A. X-linked progressive cone dystrophy. *Ophthalmology,* (1989); Vol. 96; pp. 885–895.
6) Small K W, Weber J L, Roses A, et al. North Carolina macular dystrophy is assigned to chromosome 6. *Genomics* (1992) Vol. 13; pp. 681–685.
7) Stone E M, Nichols B E, Streb L M, Kimura A E, Sheffield V C. Genetic linkage of vitelliform macular degeneration (Best's disease) to chromosome 11q13. *Nature Genet.* (1992); Vol. 1: pp. 246–250.
8) Forsman K, Graff C, Nordstrom S, et al. The gene for Best's macular dystrophy is located in 11q13 in a Swedish family. *Clin Genet.* (1992); Vol. 42: pp. 156–159.
9) Kaplan J S, Gerber S, Lavget-Piet D, et al. A gene for Stargardt's disease (fundus flavimaculatus) maps to the short arm of chromosome 1, *Nature Genet.* (1993) Vol. 5: pp. 308–311.
10) Stone E M, Nichols B E, Kimura A E, et al. Clinical features of a Stargardt-like dominant progressive macular dystrophy with genetic linkage to chromosome 6q. *Arch Opthalmol.* (1994); Vol. 112: pp. 763–772.
11) Zhang K, Bither P P, Park R, et al. A dominant Stargardt's macular dystrophy locus maps to chromosome 13q34. *Arch Opthalmol.* (1994); Vol. 112: pp. 759–764.
12) Evans K, Fryer A, Ingelhearn C, et al. Genetic linkage of cone-rod retinal dystropy to chromosome 19q and evidence for segregation distortion. *Nature Genet.* (1994); Vol. 6: pp. 210–213.
13) Kremer H, Pinckers A, vandenHelm B, et al. Localization of the gene for dominant cystoid macular dystrophy on chromosome 7p. *Hum Mol Genet,* (1994); Vol. 3: pp. 299–302.
14) Kelsell R E, Godley B F, Evans K, et al. Localization of the gene for progressive bifocal chorioretinal atrophy (PBCRA) to chromosome 6q. *Hum Mol Genet.* (1995); Vol 4: pp. 1653–1656.
15) Nathans J, Davenport C M, Maumenee I H, et al. Molecular genetics of human blue cone monochromacy. *Science.* (1989); Vol 245: pp. 831–838.
16) Wells J, Wroblewski J., Keen J. Mutations in the human retinal degeneration slow (RDS) gene can cause either retinitis pigmentosa or macular dystrophy. *Nature Genet.* (1993); Vol. 3: pp. 213–218.
17) Nichols B E, Sheffield V C, Vandenburgh K. Butterfly-shaped pigment dystrophy of the fovea is caused by a point mutation in codon 167 of the RDS gene. *Nature Genet.* (1993a); Vol. 3: pp. 202–207.
18) Weber B H F, Vogt G, Pruett R C, Stohr H, Felbor U. Mutations in the tissue inhibitor of metalloproteinases-3 (TIMP3) in patients with Sorsby's fundus dystrophy. *Nature Genet.* (1994): Vol. 8: pp. 352–355.
19) Leibowitz H., Krueger D E, Maunder L R, et al. The Framingham Eye Study Monograph; an ophthalmological and epidemiological study of cataract, macular degeneration, diabetic retinopathy, macular degeneration and visual acuity in a general population of 2,631 adults, (1973–75) *Survey of Opthalmol.* (1980); Vol. 24: (Suppl.): pp. 335–610.
20) Hutchinson J, Tay W. Symmetrical central choroidoretinal disease occurring in senile persons. *R. London Opthalmol Hosp. Rep.* (1875) Vol. 8: pp. 231–244.
21) Doyne R W. Peculiar condition of choroiditis occurring in several members of the same family. Trans. Opthal. Soc. U.K (1899); Vol.19: p. 71.
22) Collins T. A pathological report upon a case of Doyne's chorioditis ("honeycomb" or "family choroiditis"). *Ophthalmoscope* (1913); Vol. 11: pp. 537–538.
23) Vogt A. Die Opthalmoskopie im rotfreien Licht. *Graefe Saemisch Handb. d. Ges. Augenheilkd,* 3d ed. Berlin, Springer, (1925); Vol. 3: pp. 1–118.
24) Klainguti, R. Die tapeto-retinale Degeneration im Kanton Tessin (Schweiz. Opthal. Ges. 25/26-6-1932, Biel.); ref: *Z. Augenheilkd,* 82–83, 1932; *Klin. Monattsbl. Augenheilkd.* (1932); Vol. 107: pp. 361–372.
25) Waardenburg P. J. On macula-degeneration. *Opthalmologica.* (1948); Vol. 115: pp. 115–116.
26) Forni S, Babel J. Etude clinique et histologique de la *malattia leventinse.* Affection apparetnant au groupe des degenerescences hyalines du pele posterieur. *Opthalmologica.* (1962); Vol. 143: pp. 313–322.
27) Piguet B, Haimovici R, Bird A C. Dominantly inherited drusen represent more than one disorder: a historical review. *Eye* (1995); Vol. 9: pp. 34–41.

28) Streicher T, Kremery K. Das fluoreszenzangiographische Bild der heredit_ren Drusen. *Klin. Monatsbl. Augenheilkd.* (1976); Vol. 169: pp. 22–30.
29) Dusek J, Streicher T, Schmidt K. Heredit_re Drusen der Bruchschen Membran I. Klinische und lichtmikroskopische Beobachtungen. *Klin. Monatsbl. Augenheilkd.* (1982); Vol. 181: pp. 27–31.
30) Gass J D M. Diseases causing choroidal exudative and hemorrahagic localized (disciform) detachment of the retina and pigment epithelium. *Stereoscopic Atlas of Macular Diseases,* C. V. Mosby Co., St. Louis. (1987); Vol. 3: pp. 96–97.
31) Scarpatetti A., Forni S., Neimeyer G. Die Netzhautfunktion bei Malattia leventinese (dominant drusen). *Klinische Monatsblatter fur Augenheilkunde.* (1978); Vol. 4: pp. 590–7.
32) Buffone G J, Darlington G J. Isolation of DNA from biological specimens without extraction with phenol. *Clin. Chem.* (1985); Vol. 31: pp.164–165.
33) Sheffield, V. C., Weber, J. L., Buetow, K. L., et al., A Collection of tri and tetranucleotide repeat markers used to generate high quality, high resolution human genome-wide linkage maps, *Human Molecular Genetics,* in press.
34) Bassam B J, Caetano-Anolles G., Gresshoff P M. Fast and sensitive silver staining of DNA in polyacrylamide gels. *Anal Biochem.* (1991); Vol. 196: pp. 80–83.
35) Nichols B E, Bascom R., Litt M., et al. Refining the locus for Best's vitelliform macular dystrophy and mutation analysis of the candidate gene ROM1. *Am J. Hum. Genet.* (1994); Vol. 54: pp. 95–103.
36) Cottingham Jr. R W, Idury R M, Schaffer A A. Faster sequential genetic linkage computations. *Am J. Hum Genet.* (1993); Vol 53: pp. 252–263.
37) Schaffer A A, Gupta S K, Shriram K, Cottingham Jr. R W. Avoiding recomputation in genetic linkage analysis. *Hum Hered.* (1994); Vol. 44: pp. 225–237.
38) Lathrop G M, Lalouel J M. Easy calculations of lod scores and genetic risks on small computers. *Am. J. Hum. Genet.* (1984); Vol. 36: pp. 460–465.
39) Donis-Keller H, Green P., Helms C. et al. A Genetic linkage map of the human genome. *Cell.* (1987); Vol. 51: pp. 319–337.
40) Conneally P. M., Edwards J. H., Kidd K K, et al. Report of the committee on methods of linkage analysis and reporting. *Cytogenet. Cell Genet.* (1985); Vol. 40: pp. 356–359.
41) Gass J D M. Drusen and disciform macular detachment and degeneration. Arch Opthalmol. (1973); Vol. 90: pp. 206–217.
42) Hyman L G, Lilienfeld A M, Ferris F L, Fine S L. Senile macular degeneration: A case-control study. *Am J. Epidemiol.* (1983); Vol. 118: pp. 213–227.
43) Heiba I M, Elston R C, Klein B E K, Klein R. Sibling correlations and segregation analysis of age-related maculopathy: the Beaver Dam Eye Study. *Genet. Epidemiol.* (1994); Vol. 11: pp. 51–67.
44) Hu R J, Watanabe M, Bennett V. Characterization of human brain cDNA encoding the general insoform of B-spectrin. *J. Biolog. Chem.* (1992); Vol. 267: pp. 18715–18722.
45) Chang J G, Scarpa A, Eddy R L, et al. Cloning of a portion of the chromosomal gene and cDNA for human B-fordin, the nonerythroid form of B-spectrin. *Genomics,* (1993); Vol. 17: pp. 287–293.
46) Travis G, Sutcliffe J, Bok D. The retinal digeneration slow (rds) gene product is a photoreceptor disc membrane-associated glycoprotein. *Neuron* (1991); Vol. 6: pp. 61–70.
47) Bascom R A, Schappert K, McInnes R R. Cloning of the human and murine ROM 1 genes: genomic organization and sequence conservation. *Hum Molec Genet.* (1993); Vol. 2: pp. 385–391
48) Heon, E. et al., Linkage of autosomal-dominant radial drusen (malattia leventinese) to chromosome 2p16–21 *Arch. Ophthalmol.* 114: 193–198 (1996).
49) Gregory, C. Y. et al., The gene responsible for autosomal dominant Doyne's honeycomb retinal dystrophy (DHRD) maps to chromosome 2pl6 *Hum. Mol. Genet.* 5: 1055–1059 (1996).
50) Edwards, A. O. et al. Malattia leventinese: refinement of the genetic locus and phenotypic variability in autosomal dominant macular drusen. Am. J Ophthalmol. 126, 417–424 (1998).
51) Silvestri, G., Johnston, P. B. & Hughes, A. E. Is genetic predisposition an important risk factor in age-related macular degeneration? Eye 8, 564–568 (1994).
52) Meyers, S. M. A twin study on age-related macular degeneration Trans, Am. Ophthalmol. Soc. 92, 775–843 (1994).
53) Heiba, I. M., et al., Sibling correlations and segregation analysis of age-related maculopathy: the Beaver Dam Eye Study Genet. Epidemiol. 11, 51–67 (1994).
54) Bressler, N. M., Bressler, S.13. & Fine, S.L. Age-related macular degeneration *Surv. Ophthalmol.* 32,375–413 (1988).
55) Evans J. & Wormald, R. Is the incidence of registrable age-related macular degeneration increasing? Br. J. Ophthalmol. 80, 9–14 (1996).
56) Klein, R. et al. Prevalence of age-related maculopathy. The Beaver Dam Eye Study. Ophthalmol 99, 933–943 (1992).
57) Vingerling, J. R. et al. The prevalence of age-related maculopathy in the Rotterdam Study. Ophthalmol. 102, 205–210 (1995).
58) Sarks, J. P., Sarks, S. H. & Killingsworth, M. C. Evolution of soft drusen in age-related macular degeneration. Eye 8, 269–283 (1994).
59) Bird, A. C. et al., An international classification and grading system for age-related maculopathy and age-related macular degeneration. The International ARM Epidemiological Study Group. Surv. Ophthalmol. 39, 367–374 (1995).
60) Jay, M. et al., Doyne revisited. Eye 10, 469–472 (1996).
61) Tran, H., Mattei, M., Godyna, S. & Argraves, W. S. Humanfibulin-ID: molecular cloning, expression and similarity with S I-5 protein, a new member of the fibulin gene family. Matrix Mot 15, 479–493 (1997).
62) Lecka-Czemik, B., Lurnpkin, C. K. J. & Goldstein, S. An overexpressed gene transcript in senescent and quiescent human fibroblasts encoding a novel protein in the epidermal growth factor-like repeat family stimulates DNA synthesis. Mol Cell Biol 15, 120–128 (1995).
63) Dietz, H. C. et al. Marfan syndrome caused by a recurrent de novo missense mutation in the fibrillin gene Nature 352, 37–339 1991.
64) Dietz, H. C. et al. Clustering of fibrillin (FBNL) missense mutations in Marfan syndrome patients at cysteine residues in EGF-like domains. Hum. Mutat. 1, 366–374 (1992).
65) Wells, J. et al. Mutations in the human retinal degeneration slow (RDS) gene can cause either retinitis pigmentosa or macular dystrophy Nature Genet. 3, 213–218 (1993).
66) Weber, B. H. F., Vogt, G., Pruett, R. C., Stohr, H. & Felbor, U. Mutations in the tissue inhibitor of metalloproteinases-3 (timp3) in patients with sorsbys fundus dystrophy Nat. Genet, 8,352–356 (1994).
67) Allikmets, R. et al. A photoreceptor cell-specific ATP-binding transporter gene (ABCR) is mutated in recessive Stargardt macular dystrophy. Nat Genet. 15, 236–246 (1997).
68) Petrukhin, K. et al. Identification of the gene responsible for Best macular dystrophy. Nat. Genet. 19, 241–247 (1998).
69) Marquardt, A. et al. Mutations in a novel gene, VMD2, encoding a protein of unknown properties cause juvenile-onset vitelliform macular dystrophy (Best's disease). Hum. Mol. Genet, 7,1517–1525 (1998).
70) Buffone, G. J. & Darlington, G. J. Isolation of DNA from biological specimens without extraction with phenol Clin. Chem. 31, 164–165 (1985).
71) Nishimura, D. Y. et al. The forkhead transcription factor gene FKHL7 is responsible for glaucoma phenotypes which map to 6p25. Nature Genet. 19, 140–147 (1998).
72) Ikegawa, S., Toda, T., Okui, K. & Nakamura, Y. Structure and chromosomal assignment of the human S1-5 gene (FBNL) that is highly homologous to fibrillin. Genomics 35, 590592(1996).
73) Fingert, J. H. et al. Characterization and comparison of the human and the mouse GLC1A glaucoma genes. Genome Res. 8, 377–384 (1998).

What is claimed is:

1. An isolated nucleic acid encoding a polypeptide comprising an amino acid sequence identical to SEQ ID NO:1, except for an arginine to tryptophan substitution at position 345.

2. The nucleic acid of claim 1, further comprising a transcriptional regulatory sequence operably linked to the nucleic acid encoding the polypeptide.

3. The nucleic acid of claim 2, wherein the transcriptional regulatory sequence is an enhancer, a promoter or an initiator element.

4. An expression vector, which replicates in a prokaryotic cell or a eukaryotic cell, comprising the nucleic acid of claim 1.

5. A host cell transfected with the expression vector of claim 4 and expressing said polypeptide.

6. A method of producing a recombinant polypeptide comprising an amino acid sequence identical to SEQ ID NO:1, except for an arginine to tryptophan substitution at position 345, comprising culturing a cell of claim 5 in a cell culture medium, under conditions whereby the recombinant polypeptide is produced, and isolating the polypeptide from said cell culture.

7. An in vitro recombinant transfection system, comprising (i) a gene construct including the nucleic acid of claim 1 operably linked to a transcriptional regulatory sequence for causing expression of the polypeptide in an eukaryotic cell, and (ii) a gene delivery composition for delivering said gene construct to an eukaryotic cell and causing the eukaryotic cell to be transfected with said gene construct.

8. The recombinant transfection system of claim 7, wherein the gene delivery composition is selected from the group consisting of a recombinant viral particle, a liposome, and a polycationic nucleic acid binding agent.

9. The recombinant transfection system of claim 7, wherein the transcriptional regulatory sequence is a conditional transcriptional regulatory sequence.

* * * * *